(12) United States Patent
Miniaci et al.

(10) Patent No.: US 11,478,358 B2
(45) Date of Patent: Oct. 25, 2022

(54) HUMERAL AND GLENOID ARTICULAR SURFACE IMPLANT SYSTEMS AND METHODS

(71) Applicant: Arthrosurface Incorporated, Franklin, MA (US)

(72) Inventors: Anthony Miniaci, Bentleyville, OH (US); Steven W. Ek, Bolton, MA (US); Wiliam B. Murphy, Brockton, MA (US); Timothy H. Brightman, Franklin, MA (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 107 days.

(21) Appl. No.: 16/817,440

(22) Filed: Mar. 12, 2020

(65) Prior Publication Data

US 2020/0289275 A1  Sep. 17, 2020

Related U.S. Application Data

(60) Provisional application No. 62/817,497, filed on Mar. 12, 2019.

(51) Int. Cl.
*A61F 2/40* (2006.01)
*A61F 2/30* (2006.01)

(52) U.S. Cl.
CPC .......... *A61F 2/4014* (2013.01); *A61F 2/4081* (2013.01); *A61F 2002/30331* (2013.01);
(Continued)

(58) Field of Classification Search
CPC .... A61F 2/4003; A61F 2/4014; A61F 2/3603; A61F 2002/3605; A61F 2002/3615;
(Continued)

(56) References Cited

U.S. PATENT DOCUMENTS 103,645 A    5/1870   Muscroft
992,819 A    5/1911   Springer
(Continued)

FOREIGN PATENT DOCUMENTS

AU    2001262308       12/2001
AU    2001259327 B2     2/2005
(Continued)

OTHER PUBLICATIONS

Extended Search Report dated Nov. 26, 2018, issued in European Patent Application No. 16769660.8, 7 pages.
(Continued)

*Primary Examiner* — Megan Y Wolf
(74) *Attorney, Agent, or Firm* — Grossman, Tucker, Perreault & Pfleger, PLLC

(57) ABSTRACT

One embodiment of the present disclosure provides a humeral implant. The humeral implant includes a tray including a body defining a bone facing recess and a liner recess, said bone facing recess including a ring surface and a convex surface, wherein the ring surface has a profile substantially corresponding to a profile of an outer ring of bone in an excision site of a patient; and wherein said convex surface has a profile substantially corresponding to a profile of a concave socket formed in the excision site. The humeral implant also includes a liner including a body defining a load bearing surface and a tray interface surface, said tray interface surface being configured to be at least partially received in said liner recess of said tray such that said implant is coupled to said tray.

14 Claims, 52 Drawing Sheets

(52) U.S. Cl.
CPC ............... A61F 2002/4007 (2013.01); A61F 2002/4044 (2013.01); A61F 2002/4085 (2013.01); A61F 2220/0033 (2013.01)

(58) Field of Classification Search
CPC ...... A61F 2002/4007; A61F 2002/4022; A61F 2002/4085; A61F 2002/4018; A61F 2002/4037
See application file for complete search history.

(56) References Cited

U.S. PATENT DOCUMENTS

| | | |
|---|---|---|
| 1,451,610 A | 4/1923 | Gestas |
| 2,267,925 A | 12/1941 | Johnston |
| 2,379,984 A | 7/1943 | Nereaux |
| 2,381,102 A | 10/1943 | Boyd |
| 2,570,465 A | 10/1951 | Lundholm |
| 2,919,692 A | 1/1960 | Ackermann |
| 3,176,395 A | 4/1965 | Warner et al. |
| 3,351,115 A | 11/1967 | Boehlow |
| 3,664,345 A | 5/1972 | Dabbs |
| 3,715,763 A | 2/1973 | Link |
| 3,840,905 A | 10/1974 | Deane |
| 3,852,830 A | 12/1974 | Marmor |
| 3,910,281 A | 10/1975 | Kletschka et al. |
| 3,976,079 A | 8/1976 | Samuels et al. |
| 4,016,651 A | 4/1977 | Kawahara et al. |
| 4,016,874 A | 4/1977 | Maffei et al. |
| 4,034,418 A | 7/1977 | Jackson et al. |
| D245,259 S | 8/1977 | Shen |
| 4,044,464 A | 8/1977 | Schiess et al. |
| 4,158,894 A | 6/1979 | Worrell |
| 4,304,011 A | 12/1981 | Whelan, III |
| 4,309,778 A | 1/1982 | Buechel et al. |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,567,885 A | 2/1986 | Androphy |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,703,761 A | 11/1987 | Rathbone et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,741,330 A | 5/1988 | Hayhurst |
| 4,743,262 A | 5/1988 | Tronzo |
| 4,778,473 A | 10/1988 | Matthews et al. |
| 4,781,182 A | 11/1988 | Purnell et al. |
| 4,787,383 A | 11/1988 | Kenna |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,919,671 A | 4/1990 | Karpf |
| 4,920,958 A | 5/1990 | Walt et al. |
| 4,927,421 A | 5/1990 | Goble et al. |
| 4,936,853 A | 6/1990 | Fabian et al. |
| 4,938,778 A | 7/1990 | Ohyabu et al. |
| 4,940,467 A | 7/1990 | Tronzo |
| 4,945,904 A | 8/1990 | Bolton et al. |
| 4,955,916 A | 9/1990 | Carignan et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,030,219 A | 7/1991 | Matsen, III et al. |
| 5,053,049 A | 10/1991 | Campbell |
| 5,078,731 A | 1/1992 | Hayhurst |
| 5,092,895 A | 3/1992 | Albrektsson et al. |
| 5,100,405 A | 3/1992 | McLaren |
| 5,122,144 A | 6/1992 | Bert et al. |
| 5,127,413 A | 7/1992 | Ebert |
| 5,127,920 A | 7/1992 | MacArthur |
| 5,147,386 A | 9/1992 | Carignan et al. |
| 5,152,797 A | 10/1992 | Luckman et al. |
| 5,154,720 A | 10/1992 | Trott et al. |
| 5,180,384 A | 1/1993 | Mikhail |
| 5,192,291 A | 3/1993 | Pannek, Jr. |
| 5,194,066 A | 3/1993 | Van Zile |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,254,119 A | 10/1993 | Schreiber |
| 5,255,838 A | 10/1993 | Gladdish, Jr. et al. |
| 5,263,498 A | 11/1993 | Caspari et al. |
| 5,263,987 A | 11/1993 | Shah |
| 5,269,784 A | 12/1993 | Mast |
| 5,282,863 A | 2/1994 | Burton |
| 5,290,313 A | 3/1994 | Heldreth |
| 5,306,278 A | 4/1994 | Dahl et al. |
| 5,306,290 A | 4/1994 | Martins et al. |
| 5,306,301 A | 4/1994 | Graf et al. |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,326,366 A | 7/1994 | Pascarella et al. |
| 5,336,224 A | 8/1994 | Selman |
| 5,336,266 A | 8/1994 | Caspari et al. |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,376 A | 3/1995 | Caspari et al. |
| 5,395,401 A | 3/1995 | Bahler |
| 5,409,490 A | 4/1995 | Ethridge |
| 5,409,494 A | 4/1995 | Morgan |
| 5,411,504 A | 5/1995 | Vilas |
| 5,413,608 A | 5/1995 | Keller |
| 5,423,822 A | 6/1995 | Hershberger |
| 5,423,823 A | 6/1995 | Schmieding |
| 5,425,733 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,514,139 A | 5/1996 | Goldstein et al. |
| 5,520,695 A | 5/1996 | Luckman |
| 5,522,900 A | 6/1996 | Hollister |
| 5,522,901 A | 6/1996 | Thomas et al. |
| 5,529,075 A | 6/1996 | Clark |
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,352 A | 12/1996 | Sekel |
| 5,580,353 A | 12/1996 | Mendes et al. |
| 5,591,170 A | 1/1997 | Spievack et al. |

(56) References Cited

U.S. PATENT DOCUMENTS

| | | |
|---|---|---|
| 5,593,448 A | 1/1997 | Dong |
| 5,593,450 A | 1/1997 | Scott et al. |
| 5,595,193 A | 1/1997 | Walus et al. |
| 5,597,273 A | 1/1997 | Hirsch |
| 5,601,550 A | 2/1997 | Esser |
| 5,607,480 A | 3/1997 | Beaty |
| 5,609,639 A | 3/1997 | Walker |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Vitale |
| 5,700,264 A | 12/1997 | Zucherman et al. |
| 5,700,265 A | 12/1997 | Romano |
| 5,702,401 A | 12/1997 | Shaffer |
| 5,702,461 A | 12/1997 | Pappas et al. |
| 5,702,465 A | 12/1997 | Burkinshaw |
| 5,702,467 A | 12/1997 | Gabriel et al. |
| 5,720,753 A | 2/1998 | Sander et al. |
| 5,741,266 A | 4/1998 | Moran et al. |
| 5,765,973 A | 6/1998 | Hirsch et al. |
| 5,769,855 A | 6/1998 | Bertin et al. |
| 5,769,894 A | 6/1998 | Ferragamo |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,782,866 A | 7/1998 | Wenstrom, Jr. |
| 5,800,440 A | 9/1998 | Stead |
| 5,810,851 A | 9/1998 | Yoon |
| 5,816,811 A | 10/1998 | Beaty |
| 5,817,095 A | 10/1998 | Smith |
| 5,824,087 A | 10/1998 | Aspden et al. |
| 5,824,105 A | 10/1998 | Ries et al. |
| 5,827,285 A | 10/1998 | Bramlet |
| RE36,020 E | 12/1998 | Moore et al. |
| 5,871,545 A | 2/1999 | Goodfellow et al. |
| 5,879,396 A | 3/1999 | Walston et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,891,150 A | 4/1999 | Chan |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,921,986 A | 7/1999 | Bonutti |
| 5,928,239 A | 7/1999 | Mirza |
| 5,928,241 A | 7/1999 | Menut et al. |
| 5,928,286 A | 7/1999 | Ashby et al. |
| 5,951,603 A | 9/1999 | O'Neil et al. |
| 5,957,979 A | 9/1999 | Beckman et al. |
| 5,964,752 A | 10/1999 | Stone |
| 5,964,768 A | 10/1999 | Huebner |
| 5,964,805 A | 10/1999 | Stone |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,007,566 A | 12/1999 | Wenstrom, Jr. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,033,410 A | 3/2000 | McLean et al. |
| 6,045,554 A | 4/2000 | Grooms et al. |
| 6,045,564 A | 4/2000 | Walen |
| 6,052,909 A | 4/2000 | Gardner |
| 6,053,945 A | 4/2000 | O'Neil et al. |
| 6,059,831 A | 5/2000 | Braslow |
| 6,063,091 A | 5/2000 | Lombardo et al. |
| 6,069,295 A | 5/2000 | Leitao |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,099,568 A | 8/2000 | Simonian et al. |
| 6,099,571 A | 8/2000 | Knapp |
| 6,102,948 A | 8/2000 | Brosnahan, III |
| 6,102,954 A | 8/2000 | Albrektsson et al. |
| 6,110,207 A | 8/2000 | Eichhorn et al. |
| 6,120,511 A | 9/2000 | Chan |
| 6,120,542 A | 9/2000 | Camino et al. |
| 6,132,433 A | 10/2000 | Whelan |
| 6,139,508 A | 10/2000 | Simpson et al. |
| 6,146,385 A | 11/2000 | Torrie et al. |
| 6,149,654 A | 11/2000 | Lanny |
| 6,152,960 A | 11/2000 | Pappas |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,206,926 B1 | 3/2001 | Pappas |
| 6,207,218 B1 | 3/2001 | Layrolle et al. |
| 6,217,549 B1 | 4/2001 | Selmon et al. |
| 6,217,619 B1 | 4/2001 | Keller |
| 6,228,119 B1 | 5/2001 | Ondrla et al. |
| 6,231,611 B1 | 5/2001 | Mosseri |
| 6,235,060 B1 | 5/2001 | Kubein-Meesenburg et al. |
| 6,245,074 B1 | 6/2001 | Allard et al. |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,310,116 B1 | 10/2001 | Yasuda et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,364,910 B1 | 4/2002 | Shultz et al. |
| 6,375,658 B1 | 4/2002 | Hangody et al. |
| 6,383,188 B2 | 5/2002 | Kuslich |
| 6,402,785 B1 | 6/2002 | Zdeblick et al. |
| 6,415,516 B1 | 7/2002 | Tirado et al. |
| 6,416,518 B1 | 7/2002 | DeMayo |
| 6,443,954 B1 | 9/2002 | Bramlet et al. |
| 6,451,023 B1 | 9/2002 | Salazar et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown |
| 6,517,541 B1 | 2/2003 | Sesic |
| 6,517,542 B1 | 2/2003 | Papay et al. |
| 6,517,578 B2 | 2/2003 | Hein |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,547,823 B2 | 4/2003 | Scarborough et al. |
| 6,551,322 B1 | 4/2003 | Lieberman |
| 6,554,866 B1 | 4/2003 | Aicher et al. |
| 6,558,422 B1 | 5/2003 | Baker et al. |

(56) References Cited

U.S. PATENT DOCUMENTS

| | | |
|---|---|---|
| 6,569,202 B2 | 5/2003 | Whiteside |
| 6,575,980 B1 | 6/2003 | Robie et al. |
| 6,575,982 B1 | 6/2003 | Bonutti |
| 6,585,666 B2 | 7/2003 | Suh et al. |
| 6,589,281 B2 | 7/2003 | Hyde, Jr. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,610,095 B1 | 8/2003 | Pope et al. |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,638,279 B2 | 10/2003 | Bonutti |
| 6,679,916 B1 | 1/2004 | Frankle et al. |
| 6,679,917 B2 | 1/2004 | Ek |
| 6,720,469 B1 | 4/2004 | Curtis et al. |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,881,228 B2 | 4/2005 | Zdeblick et al. |
| 6,884,246 B1 | 4/2005 | Sonnabend et al. |
| 6,884,621 B2 | 4/2005 | Liao et al. |
| 6,893,467 B1 | 5/2005 | Bercovy |
| 6,913,463 B2 | 7/2005 | Blacklock |
| 6,923,813 B2 | 8/2005 | Phillips et al. |
| 6,926,739 B1 | 8/2005 | Oconnor |
| 6,951,538 B2 | 10/2005 | Ritland |
| 6,953,478 B2 | 10/2005 | Bouttens et al. |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,105,027 B2 | 9/2006 | Lipman et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,169,184 B2 | 1/2007 | Dalla Pria |
| 7,192,431 B2 | 3/2007 | Hangody et al. |
| 7,192,432 B2 | 3/2007 | Wetzler et al. |
| 7,204,839 B2 | 4/2007 | Dreyfuss et al. |
| 7,204,854 B2 | 4/2007 | Guederian et al. |
| 7,229,448 B2 | 6/2007 | Goble et al. |
| 7,235,091 B2 | 6/2007 | Thornes |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augustino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,455,683 B2 | 11/2008 | Geissler et al. |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,731,738 B2 | 6/2010 | Jackson et al. |
| 7,738,187 B2 | 6/2010 | Pazidis et al. |
| 7,740,662 B2 | 6/2010 | Barnett et al. |
| 7,758,643 B2 | 7/2010 | Stone et al. |
| 7,776,085 B2 | 8/2010 | Bernero et al. |
| 7,806,872 B2 | 10/2010 | Ponzi |
| 7,815,645 B2 | 10/2010 | Haines |
| 7,815,681 B2 | 10/2010 | Ferguson |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,875,058 B2 | 1/2011 | Holmes, Jr. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,901,431 B2 | 3/2011 | Shumas |
| 7,914,545 B2 | 3/2011 | Ek |
| 7,931,683 B2 | 4/2011 | Weber et al. |
| 7,951,163 B2 | 5/2011 | Ek |
| 7,951,204 B2 | 5/2011 | Chambat et al. |
| 7,955,382 B2 | 6/2011 | Flanagan et al. |
| 7,959,636 B2 | 6/2011 | Schmieding |
| 7,959,650 B2 | 6/2011 | Kaiser et al. |
| 7,959,681 B2 | 6/2011 | Lavi |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 3,012,206 A1 | 9/2011 | Schmieding |
| 3,021,367 A1 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,114,163 B2 | 2/2012 | Berelsman et al. |
| 8,137,406 B2 | 3/2012 | Novak et al. |
| 8,137,407 B2 | 3/2012 | Todd et al. |
| 8,142,502 B2 | 3/2012 | Stone et al. |
| 8,147,514 B2 | 4/2012 | Bonutti |
| 8,147,559 B2 | 4/2012 | Tallarida et al. |
| 8,152,847 B2 | 4/2012 | Strzepa et al. |
| 8,157,867 B2 | 4/2012 | Goble et al. |
| 8,162,947 B2 | 4/2012 | Dreyfuss |
| 8,163,027 B2 | 4/2012 | Rhodes et al. |
| 8,167,951 B2 | 5/2012 | Ammann et al. |
| 8,177,738 B2 | 5/2012 | Schmieding et al. |
| 8,177,841 B2 | 5/2012 | Ek |

(56) References Cited

U.S. PATENT DOCUMENTS

| | | |
|---|---|---|
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shumas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,267,977 B2 | 9/2012 | Roth |
| 8,277,459 B2 | 10/2012 | Sand et al. |
| 8,298,247 B2 | 10/2012 | Sterrett et al. |
| 8,298,284 B2 | 10/2012 | Cassani |
| 8,303,830 B2 | 11/2012 | Tong et al. |
| 8,308,662 B2 | 11/2012 | Lo |
| 8,308,732 B2 | 11/2012 | Millett et al. |
| 8,308,781 B2 | 11/2012 | Wilson et al. |
| 8,317,870 B2 | 11/2012 | Wagner et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,337,563 B2 | 12/2012 | Roche et al. |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,414,908 B2 | 4/2013 | Jin et al. |
| 8,419,794 B2 | 4/2013 | ElAttrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 8,470,047 B2 | 6/2013 | Hazebrouck et al. |
| 8,475,536 B2 | 7/2013 | Tong et al. |
| 8,486,072 B2 | 7/2013 | Haininger |
| 8,496,662 B2 | 7/2013 | Novak et al. |
| 8,506,573 B2 | 8/2013 | Dreyfuss et al. |
| 8,512,376 B2 | 8/2013 | Thornes |
| 8,512,411 B2 | 8/2013 | Sluss et al. |
| 8,523,872 B2 | 9/2013 | Ek |
| 8,535,330 B2 | 9/2013 | Sherman et al. |
| 8,535,703 B2 | 9/2013 | Schmieding et al. |
| 8,540,717 B2 | 9/2013 | Tallarida et al. |
| 8,540,777 B2 | 9/2013 | Ammann et al. |
| 8,540,778 B2 | 9/2013 | Rhodes et al. |
| 8,551,101 B2 | 10/2013 | Kuczynski |
| 8,556,984 B2 | 10/2013 | Calamel |
| 8,579,940 B2 | 11/2013 | Dreyfuss et al. |
| 8,579,944 B2 | 11/2013 | Holloway et al. |
| 8,591,514 B2 | 11/2013 | Sherman |
| 8,591,523 B2 | 11/2013 | Weber |
| 8,591,544 B2 | 11/2013 | Jolly et al. |
| 8,591,578 B2 | 11/2013 | Albertorio et al. |
| 8,591,592 B2 | 11/2013 | Dreyfuss |
| 8,591,594 B2 | 11/2013 | Parisi et al. |
| 8,597,361 B2 | 12/2013 | Sidebotham et al. |
| 8,623,052 B2 | 1/2014 | Dreyfuss et al. |
| 8,628,573 B2 | 1/2014 | Roller et al. |
| 8,652,139 B2 | 2/2014 | Sterrett et al. |
| 8,663,230 B2 | 3/2014 | Miniaci et al. |
| 8,663,250 B2 | 3/2014 | Weber |
| 8,663,251 B2 | 3/2014 | Burkhart et al. |
| 8,663,279 B2 | 3/2014 | Burkhart et al. |
| 8,663,324 B2 | 3/2014 | Schmieding et al. |
| 8,663,333 B2 | 3/2014 | Metcalfe et al. |
| 8,668,738 B2 | 3/2014 | Schmieding et al. |
| 8,690,952 B2 | 4/2014 | Dallmann |
| 8,702,715 B2 | 4/2014 | Ammann et al. |
| 8,702,752 B2 | 4/2014 | Schmieding et al. |
| 8,709,052 B2 | 4/2014 | Ammann et al. |
| 8,709,091 B2 | 4/2014 | Rhodes et al. |
| 8,721,722 B2 | 5/2014 | Shah et al. |
| 8,728,131 B2 | 5/2014 | Di Giacomo et al. |
| 8,734,449 B2 | 5/2014 | Schmied et al. |
| 8,753,375 B2 | 6/2014 | Albertorio |
| 8,758,356 B2 | 6/2014 | Fearon et al. |
| 8,764,797 B2 | 7/2014 | Dreyfuss et al. |
| 8,764,807 B2 | 7/2014 | Michel et al. |
| 8,764,839 B2 | 7/2014 | Rhodes et al. |
| 8,771,279 B2 | 7/2014 | Philippon et al. |
| 8,771,351 B2 | 7/2014 | ElAttrache et al. |
| 8,784,423 B2 | 7/2014 | Kowarsch et al. |
| 8,790,401 B2 | 7/2014 | Schmieding et al. |
| 8,801,755 B2 | 8/2014 | Dreyfuss et al. |
| 8,821,541 B2 | 9/2014 | Dreyfuss et al. |
| 8,834,475 B2 | 9/2014 | Ammann et al. |
| 8,834,521 B2 | 9/2014 | Pinto et al. |
| 8,840,619 B2 | 9/2014 | Zajac et al. |
| 8,840,643 B2 | 9/2014 | Dreyfuss |
| 8,840,676 B2 | 9/2014 | Belew et al. |
| 8,852,190 B2 | 10/2014 | Sherman |
| 8,852,201 B2 | 10/2014 | Schmieding et al. |
| 8,858,560 B2 | 10/2014 | Bradley et al. |
| 8,864,827 B2 | 10/2014 | Ek |
| 8,870,877 B2 | 10/2014 | Koogle, Jr. |
| 8,870,962 B2 | 10/2014 | Roche et al. |
| 8,876,900 B2 | 11/2014 | Guederian et al. |
| 8,882,833 B2 | 11/2014 | Saylor et al. |
| 8,882,845 B2 | 11/2014 | Wirth et al. |
| 8,882,847 B2 | 11/2014 | Burdulis, Jr. et al. |
| 8,888,781 B2 | 11/2014 | Sterrett |
| 8,888,785 B2 | 11/2014 | Ammann et al. |
| 8,888,815 B2 | 11/2014 | Holmes, Jr. |
| 8,888,855 B2 | 11/2014 | Roche et al. |
| 8,906,026 B2 | 12/2014 | Ammann et al. |
| 8,911,457 B2 | 12/2014 | Koogle, Jr. et al. |
| 8,920,497 B2 | 12/2014 | Albertorio et al. |
| 8,920,508 B2 | 12/2014 | Iannotti et al. |
| 8,926,615 B2 | 1/2015 | Ek |
| 8,927,283 B2 | 1/2015 | Komvopoulos et al. |
| 8,939,980 B2 | 1/2015 | Schmieding et al. |
| 8,939,999 B2 | 1/2015 | Sterrett et al. |
| 8,956,369 B2 | 2/2015 | Millett et al. |
| 8,961,538 B2 | 2/2015 | Koogle, Jr. et al. |
| 8,961,575 B2 | 2/2015 | Choinski |
| 8,961,614 B2 | 2/2015 | Ek et al. |
| 8,974,537 B2 | 3/2015 | Dreyfuss |
| 8,986,346 B2 | 3/2015 | Dreyfuss |
| 9,005,245 B2 | 4/2015 | Thornes et al. |
| 9,005,246 B2 | 4/2015 | Burkhart et al. |
| 9,044,343 B2 | 6/2015 | Ek |
| 9,055,955 B2 | 6/2015 | Ek et al. |
| 9,066,716 B2 | 6/2015 | Sikora et al. |
| 9,072,510 B2 | 7/2015 | Thornes et al. |
| 9,072,555 B2 | 7/2015 | Michel |
| 9,078,650 B2 | 7/2015 | Weber |
| 9,078,661 B2 | 7/2015 | Gallo |
| 9,089,363 B2 | 7/2015 | Dooney, Jr. et al. |
| 9,089,433 B2 | 7/2015 | Karnes et al. |
| 9,095,641 B2 | 8/2015 | Albertorio |
| 9,101,366 B2 | 8/2015 | Sterrett et al. |
| 9,101,461 B2 | 8/2015 | Albertorio et al. |
| 9,107,653 B2 | 8/2015 | Sullivan |
| 9,107,676 B2 | 8/2015 | Burkhart et al. |
| 9,113,859 B2 | 8/2015 | Dooney, Jr. et al. |
| 9,113,920 B2 | 8/2015 | Ammann et al. |
| 9,138,223 B2 | 9/2015 | Jolly et al. |
| 9,138,237 B2 | 9/2015 | Meade et al. |

(56) References Cited

U.S. PATENT DOCUMENTS

| | | |
|---|---|---|
| 9,138,241 B2 | 9/2015 | Kuczynski |
| 9,138,246 B2 | 9/2015 | Anderson et al. |
| 9,138,274 B1 | 9/2015 | Biesinger et al. |
| 9,146,576 B2 | 9/2015 | Schmieding et al. |
| 9,168,124 B2 | 10/2015 | Guerra et al. |
| 9,179,907 B2 | 11/2015 | ElAttrache et al. |
| 9,179,950 B2 | 11/2015 | Zajac et al. |
| 9,186,432 B2 | 11/2015 | Mazzocca et al. |
| 9,204,873 B2 | 12/2015 | Tallarida et al. |
| 9,204,874 B2 | 12/2015 | Denove et al. |
| 9,204,960 B2 | 12/2015 | Albertorio et al. |
| 9,211,126 B2 | 12/2015 | Sikora et al. |
| 9,216,017 B2 | 12/2015 | Burkhart |
| 9,216,022 B2 | 12/2015 | Karnes et al. |
| 9,216,090 B2 | 12/2015 | Metcalfe |
| 9,216,091 B2 | 12/2015 | Hardy et al. |
| 9,226,743 B2 | 1/2016 | Dreyfuss et al. |
| 9,226,815 B2 | 1/2016 | Schmieding et al. |
| 9,233,003 B2 | 1/2016 | Roche et al. |
| 9,278,413 B2 | 3/2016 | Sperling |
| 9,283,076 B2 | 3/2016 | Sikora et al. |
| 9,289,221 B2 | 3/2016 | Gelaude et al. |
| 9,295,556 B2 | 3/2016 | Perez, III et al. |
| 9,301,745 B2 | 4/2016 | Dreyfuss |
| 9,301,847 B2 | 4/2016 | Guederian et al. |
| 9,320,512 B2 | 4/2016 | Dooney, Jr. |
| 9,332,979 B2 | 5/2016 | Sullivan et al. |
| 9,333,019 B2 | 5/2016 | Khosla et al. |
| 9,345,471 B2 | 5/2016 | Sullivan |
| 9,351,722 B2 | 5/2016 | Koogle, Jr. et al. |
| 9,351,743 B2 | 5/2016 | Kehres et al. |
| 9,351,745 B2 | 5/2016 | Ek et al. |
| 9,357,989 B2 | 6/2016 | Tallarida et al. |
| 9,358,029 B2 | 6/2016 | Sikora et al. |
| 9,364,214 B2 | 6/2016 | Courage |
| 9,381,022 B2 | 7/2016 | Bradley et al. |
| 9,381,053 B2 | 7/2016 | Parsons et al. |
| 9,393,010 B2 | 7/2016 | Murray et al. |
| 9,402,730 B2 | 8/2016 | Lederman et al. |
| 9,421,007 B2 | 8/2016 | Brady et al. |
| 9,421,008 B2 | 8/2016 | Burkhart et al. |
| 9,421,010 B2 | 8/2016 | Dreyfuss |
| 9,421,086 B2 | 8/2016 | Roller et al. |
| 9,421,105 B2 | 8/2016 | Metcalfe et al. |
| 9,421,106 B2 | 8/2016 | Splieth et al. |
| 9,451,951 B2 | 9/2016 | Sullivan et al. |
| 9,463,011 B2 | 10/2016 | Dreyfuss et al. |
| 9,468,448 B2 | 10/2016 | Sikora et al. |
| 9,485,475 B2 | 11/2016 | Speier et al. |
| 9,486,207 B2 | 11/2016 | Dooney, Jr. et al. |
| 9,486,317 B2 | 11/2016 | Milano et al. |
| 9,492,200 B2 | 11/2016 | Sikora et al. |
| 9,498,232 B2 | 11/2016 | Perez, III |
| 9,498,344 B2 | 11/2016 | Hodorek et al. |
| 9,504,462 B2 | 11/2016 | Dooney, Jr. et al. |
| 9,510,840 B2 | 12/2016 | Sikora et al. |
| 9,510,951 B2 | 12/2016 | Bachmaier |
| 9,521,999 B2 | 12/2016 | Dreyfuss et al. |
| 9,526,493 B2 | 12/2016 | Dreyfuss et al. |
| 9,526,510 B2 | 12/2016 | Sterrett |
| 9,549,701 B2 | 1/2017 | Peterson et al. |
| 9,549,726 B2 | 1/2017 | Dreyfuss et al. |
| 9,603,712 B2 | 3/2017 | Bachmaier |
| 9,610,167 B2 | 4/2017 | Hardy et al. |
| 9,615,821 B2 | 4/2017 | Sullivan |
| 9,622,738 B2 | 4/2017 | Dreyfuss et al. |
| 9,622,739 B2 | 4/2017 | Dreyfuss et al. |
| 9,622,775 B2 | 4/2017 | Jolly et al. |
| 9,622,869 B2 | 4/2017 | Nerot et al. |
| 9,629,725 B2 | 4/2017 | Gargac et al. |
| 9,642,609 B2 | 5/2017 | Holmes, Jr. |
| 9,642,610 B2 | 5/2017 | Albertorio et al. |
| 9,662,126 B2 | 5/2017 | Sikora et al. |
| 9,687,222 B2 | 6/2017 | Dreyfuss et al. |
| 9,687,256 B2 | 6/2017 | Granberry et al. |
| 9,687,338 B2 | 6/2017 | Albertorio et al. |
| 9,693,765 B2 | 7/2017 | Sullivan et al. |
| 9,693,787 B2 | 7/2017 | Ammann et al. |
| 9,706,986 B2 | 7/2017 | ElAttrache et al. |
| 9,707,023 B2 | 7/2017 | Ammann et al. |
| 9,724,138 B2 | 8/2017 | Palmer et al. |
| 9,724,168 B2 | 8/2017 | Yeung |
| 9,737,292 B2 | 8/2017 | Sullivan et al. |
| 9,750,850 B2 | 9/2017 | Fonte et al. |
| 9,763,798 B2 | 9/2017 | Chavarria et al. |
| 9,775,599 B2 | 10/2017 | ElAttrache et al. |
| 9,795,392 B2 | 10/2017 | Zajac |
| 9,801,625 B2 | 10/2017 | Dooney, Jr. et al. |
| 9,801,707 B2 | 10/2017 | Cassani |
| 9,801,726 B2 | 10/2017 | Karnes et al. |
| 9,808,240 B2 | 11/2017 | Parsons et al. |
| 9,814,455 B2 | 11/2017 | Dooney, Jr. et al. |
| 9,814,499 B2 | 11/2017 | Buscaglia et al. |
| 9,833,260 B2 | 12/2017 | Jolly et al. |
| 9,839,438 B2 | 12/2017 | Eash |
| 9,839,462 B2 | 12/2017 | Zajac |
| 9,855,029 B2 | 1/2018 | Sullivan |
| 9,855,036 B2 | 1/2018 | Palmer et al. |
| 9,855,064 B2 | 1/2018 | Albertorio et al. |
| 9,855,132 B2 | 1/2018 | Hoover et al. |
| 9,855,146 B2 | 1/2018 | Schmieding |
| 9,861,357 B2 | 1/2018 | Palmer et al. |
| 9,861,413 B2 | 1/2018 | Palmer et al. |
| 9,861,417 B2 | 1/2018 | Helenbolt et al. |
| 9,861,492 B2 | 1/2018 | Ek |
| 9,867,607 B2 | 1/2018 | Sullivan |
| 9,877,712 B2 | 1/2018 | Provencher et al. |
| 9,877,758 B2 | 1/2018 | Michel |
| 9,888,997 B2 | 2/2018 | Dreyfuss et al. |
| 9,895,177 B2 | 2/2018 | Hientzsch et al. |
| 9,907,655 B2 | 3/2018 | Ingwer et al. |
| 9,907,657 B2 | 3/2018 | Fonte et al. |
| 9,913,640 B2 | 3/2018 | Perez, III |
| 9,918,769 B2 | 3/2018 | Provencher et al. |
| 9,931,115 B2 | 4/2018 | Morgan et al. |
| 9,931,211 B2 | 4/2018 | Ek et al. |
| 9,931,219 B2 | 4/2018 | Sikora et al. |
| 9,956,083 B2 | 5/2018 | Humphrey |
| 9,962,265 B2 | 5/2018 | Ek et al. |
| 9,974,537 B2 | 5/2018 | Coughlin et al. |
| 9,974,550 B2 | 5/2018 | Seitlinger et al. |
| 9,999,416 B2 | 6/2018 | Kelly et al. |
| 10,034,759 B2 | 7/2018 | Deransart et al. |
| 10,045,770 B2 | 8/2018 | Burkhart et al. |
| 10,045,788 B2 | 8/2018 | Sikora et al. |
| 10,052,091 B2 | 8/2018 | Dreyfuss et al. |
| 10,058,322 B2 | 8/2018 | Dooney, Jr. et al. |
| 10,064,983 B2 | 8/2018 | Weber et al. |
| 10,076,321 B2 | 9/2018 | Crane et al. |
| 10,076,322 B1 | 9/2018 | Dreyfuss |
| 10,076,343 B2 | 9/2018 | Ek |
| 10,076,407 B2 | 9/2018 | Albertorio et al. |
| 10,080,557 B1 | 9/2018 | Laviano et al. |
| 10,085,739 B2 | 10/2018 | Dooney, Jr. et al. |
| 10,092,340 B2 | 10/2018 | Choinski et al. |
| 10,111,649 B2 | 10/2018 | Laviano et al. |
| 10,117,657 B2 | 11/2018 | Guederian |
| 10,143,558 B2 | 12/2018 | Frankle |
| 10,159,518 B2 | 12/2018 | Holowecky et al. |
| 10,172,606 B2 | 1/2019 | Sullivan et al. |
| 10,172,607 B2 | 1/2019 | Burkhart |
| 10,172,703 B2 | 1/2019 | Adams et al. |
| 10,172,714 B2 | 1/2019 | Hatzidakis et al. |
| 10,182,917 B2 | 1/2019 | Zajac |
| 10,188,504 B2 | 1/2019 | Cassani |
| 10,194,899 B2 | 2/2019 | Benavitz et al. |
| 10,206,670 B2 | 2/2019 | Thornes |
| 10,206,694 B2 | 2/2019 | Libby et al. |
| 10,213,219 B2 | 2/2019 | Garlock et al. |
| 10,238,484 B2 | 3/2019 | Albertorio et al. |
| 10,245,016 B2 | 4/2019 | Zajac et al. |
| 10,251,655 B2 | 4/2019 | Sterrett |
| 10,251,656 B2 | 4/2019 | Granberry et al. |
| 10,251,686 B2 | 4/2019 | Zajac et al. |

(56) References Cited

U.S. PATENT DOCUMENTS

| | | |
|---|---|---|
| 10,258,320 B2 | 4/2019 | Dreyfuss et al. |
| 10,265,060 B2 | 4/2019 | Dooney, Jr. et al. |
| 10,271,858 B2 | 4/2019 | Guilloux et al. |
| 10,285,801 B2 | 5/2019 | Roller et al. |
| 10,299,841 B2 | 5/2019 | Dunlop et al. |
| 10,307,154 B2 | 6/2019 | Michalik et al. |
| 10,363,024 B2 | 7/2019 | Koogle, Jr. et al. |
| 10,398,426 B2 | 9/2019 | Burkhart et al. |
| 10,398,514 B2 | 9/2019 | Ryan et al. |
| 10,405,904 B2 | 9/2019 | Hientzsch et al. |
| 10,413,341 B2 | 9/2019 | Chaudot et al. |
| 10,420,597 B2 | 9/2019 | Papangelou et al. |
| 10,420,649 B2 | 9/2019 | Overes et al. |
| 10,426,495 B2 | 10/2019 | Bonin, Jr. et al. |
| 10,441,298 B2 | 10/2019 | Eash |
| 10,448,945 B2 | 10/2019 | Bachmaier et al. |
| 10,456,145 B2 | 10/2019 | Laviano et al. |
| 10,478,200 B2 | 11/2019 | Sikora et al. |
| 10,485,670 B2 | 11/2019 | Maale |
| 10,499,932 B2 | 12/2019 | Koogle, Jr. et al. |
| 10,512,543 B2 | 12/2019 | Ingwer et al. |
| 10,537,390 B2 | 1/2020 | Varadarajan et al. |
| 10,548,737 B2 | 2/2020 | Hodorek et al. |
| 10,575,957 B2 | 3/2020 | Ek |
| 10,583,012 B1 | 3/2020 | Longobardi |
| 10,595,886 B2 | 3/2020 | Termanini |
| 10,624,748 B2 | 4/2020 | Ek et al. |
| 10,624,749 B2 | 4/2020 | Ek et al. |
| 10,624,752 B2 | 4/2020 | Sikora et al. |
| 10,624,754 B2 | 4/2020 | Ek et al. |
| 10,631,992 B2 | 4/2020 | Hopkins |
| 10,695,096 B2 | 6/2020 | Sikora et al. |
| 10,709,565 B2 | 7/2020 | Humphrey et al. |
| 10,736,751 B2 | 8/2020 | Hodorek et al. |
| 10,945,743 B2 | 3/2021 | Sikora et al. |
| 10,959,740 B2 | 3/2021 | Sikora et al. |
| 10,966,814 B2 | 4/2021 | Hansen et al. |
| 10,973,645 B2 | 4/2021 | Deransart et al. |
| 10,987,176 B2 | 4/2021 | Poltaretskyi et al. |
| 11,020,128 B2 | 6/2021 | Guilloux et al. |
| 11,033,399 B2 | 6/2021 | Hatzidakis et al. |
| 11,065,125 B2 | 7/2021 | Ball |
| 11,071,596 B2 | 7/2021 | Ryan et al. |
| 11,083,525 B2 | 8/2021 | Varadarajan et al. |
| 11,090,123 B2 | 8/2021 | Yeung |
| 11,103,357 B2 | 8/2021 | Gargac et al. |
| 11,129,724 B2 | 9/2021 | Knox et al. |
| 11,166,733 B2 | 11/2021 | Neichel et al. |
| 11,173,037 B2 | 11/2021 | Deransart et al. |
| 11,197,764 B2 | 12/2021 | Mutchler et al. |
| 11,229,522 B2 | 1/2022 | Nerot et al. |
| 11,234,721 B2 | 2/2022 | Gargac et al. |
| 2001/0010023 A1 | 7/2001 | Schwartz et al. |
| 2001/0012967 A1 | 8/2001 | Mosseri |
| 2001/0016775 A1 | 8/2001 | Scarborough et al. |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0022890 A1 | 2/2002 | Jacobsson et al. |
| 2002/0049444 A1 | 4/2002 | Knox |
| 2002/0055783 A1 | 5/2002 | Tallarida et al. |
| 2002/0082701 A1 | 6/2002 | Zdeblick et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2002/0183760 A1 | 12/2002 | McGovern et al. |
| 2003/0028196 A1 | 2/2003 | Bonutti |
| 2003/0060887 A1 | 3/2003 | Ek |
| 2003/0065332 A1 | 4/2003 | TenHuisen et al. |
| 2003/0065391 A1 | 4/2003 | Re et al. |
| 2003/0083751 A1 | 5/2003 | Tornier |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0171820 A1 | 9/2003 | Wilshaw et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0204267 A1 | 10/2003 | Hazebrouck et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0064190 A1 | 4/2004 | Ball et al. |
| 2004/0082906 A1 | 4/2004 | Tallarida et al. |
| 2004/0083005 A1 | 4/2004 | Jacobsson et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153086 A1 | 8/2004 | Sanford |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0176775 A1 | 9/2004 | Burkus et al. |
| 2004/0186582 A1 | 9/2004 | Yasuda et al. |
| 2004/0193172 A1 | 9/2004 | Ross et al. |
| 2004/0193175 A1 | 9/2004 | Maroney et al. |
| 2004/0193267 A1 | 9/2004 | Jones et al. |
| 2004/0193268 A1 | 9/2004 | Hazebrouck |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0236339 A1 | 11/2004 | Pepper |
| 2004/0254585 A1 | 12/2004 | Whittaker et al. |
| 2004/0260298 A1 | 12/2004 | Kaiser et al. |
| 2004/0260303 A1 | 12/2004 | Carrison |
| 2005/0015092 A1 | 1/2005 | Rathbun et al. |
| 2005/0015153 A1 | 1/2005 | Gobel et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0049716 A1 | 3/2005 | Wagener et al. |
| 2005/0065612 A1 | 3/2005 | Winslow |
| 2005/0071014 A1 | 3/2005 | Barnett et al. |
| 2005/0075642 A1 | 4/2005 | Felt |
| 2005/0085909 A1 | 4/2005 | Eisermann |
| 2005/0090905 A1 | 4/2005 | Hawkins et al. |
| 2005/0107799 A1 | 5/2005 | Graf et al. |
| 2005/0119758 A1 | 6/2005 | Alexander et al. |
| 2005/0143731 A1 | 6/2005 | Justin et al. |
| 2005/0143745 A1 | 6/2005 | Hodorek et al. |
| 2005/0143821 A1 | 6/2005 | Zdeblick et al. |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0165407 A1 | 7/2005 | Diaz |
| 2005/0165487 A1 | 7/2005 | Muhanna et al. |
| 2005/0177171 A1 | 8/2005 | Wetzler et al. |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |

(56) References Cited

U.S. PATENT DOCUMENTS

| | | |
|---|---|---|
| 2005/0234461 A1 | 10/2005 | Burdulis, Jr. et al. |
| 2005/0245932 A1 | 11/2005 | Fanton et al. |
| 2005/0251268 A1 | 11/2005 | Truncale |
| 2005/0273112 A1 | 12/2005 | McNamara |
| 2005/0287187 A1 | 12/2005 | Mansmann |
| 2006/0004461 A1 | 1/2006 | Justin et al. |
| 2006/0009774 A1 | 1/2006 | Goble et al. |
| 2006/0009852 A1 | 1/2006 | Winslow et al. |
| 2006/0020343 A1 | 1/2006 | Ek |
| 2006/0041261 A1 | 2/2006 | Osypka |
| 2006/0052878 A1 | 3/2006 | Schmieding |
| 2006/0058744 A1 | 3/2006 | Tallarida et al. |
| 2006/0058809 A1 | 3/2006 | Zink et al. |
| 2006/0058883 A1 | 3/2006 | Aram et al. |
| 2006/0069394 A1 | 3/2006 | Weiler et al. |
| 2006/0074430 A1 | 4/2006 | Deffenbaugh et al. |
| 2006/0085006 A1 | 4/2006 | Ek |
| 2006/0085077 A1 | 4/2006 | Cook et al. |
| 2006/0105015 A1 | 5/2006 | Perla et al. |
| 2006/0111787 A1 | 5/2006 | Bailie et al. |
| 2006/0121080 A1 | 6/2006 | Lye et al. |
| 2006/0142772 A1 | 6/2006 | Ralph et al. |
| 2006/0149370 A1 | 7/2006 | Schmieding et al. |
| 2006/0154206 A1 | 7/2006 | Petersson et al. |
| 2006/0167560 A1 | 7/2006 | Heck et al. |
| 2006/0184187 A1 | 8/2006 | Surti |
| 2006/0190002 A1 | 8/2006 | Tallarida |
| 2006/0195112 A1 | 8/2006 | Ek |
| 2006/0217728 A1 | 9/2006 | Chervitz et al. |
| 2006/0229726 A1 | 10/2006 | Ek |
| 2006/0271059 A1 | 11/2006 | Reay-Young et al. |
| 2007/0005143 A1 | 1/2007 | Ek |
| 2007/0016208 A1 | 1/2007 | Thornes |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0129808 A1 | 6/2007 | Justin et al. |
| 2007/0134291 A1 | 6/2007 | Ting et al. |
| 2007/0173850 A1 | 7/2007 | Rangaiah et al. |
| 2007/0179531 A1 | 8/2007 | Thornes |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270711 A1 | 11/2007 | Gil et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0299519 A1 | 12/2007 | Schmieding |
| 2007/0299529 A1 | 12/2007 | Rhodes et al. |
| 2008/0004659 A1 | 1/2008 | Burkhart et al. |
| 2008/0015607 A1 | 1/2008 | D'Alessio et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046009 A1 | 2/2008 | Albertorio et al. |
| 2008/0046084 A1 | 2/2008 | Sledge |
| 2008/0071381 A1 | 3/2008 | Buscher et al. |
| 2008/0077182 A1 | 3/2008 | Geissler et al. |
| 2008/0086139 A1 | 4/2008 | Bourke et al. |
| 2008/0086152 A1 | 4/2008 | McKay et al. |
| 2008/0091271 A1 | 4/2008 | Bonitati et al. |
| 2008/0091272 A1 | 4/2008 | Aram et al. |
| 2008/0097618 A1 | 4/2008 | Baker et al. |
| 2008/0103506 A1 | 5/2008 | Volpi et al. |
| 2008/0114463 A1 | 5/2008 | Auger et al. |
| 2008/0138611 A1 | 6/2008 | Yasuzawa et al. |
| 2008/0154271 A1 | 6/2008 | Berberich et al. |
| 2008/0172125 A1 | 7/2008 | Ek |
| 2008/0177200 A1 | 7/2008 | Ikehara et al. |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0200904 A1 | 8/2008 | Cluff et al. |
| 2008/0208201 A1 | 8/2008 | Moindreau et al. |
| 2008/0243262 A1 | 10/2008 | Lee |
| 2008/0243263 A1 | 10/2008 | Lee et al. |
| 2008/0262500 A1 | 10/2008 | Collazo |
| 2008/0262625 A1 | 10/2008 | Spriano et al. |
| 2008/0275451 A1 | 11/2008 | McAllister et al. |
| 2008/0275512 A1 | 11/2008 | Albertirio et al. |
| 2008/0294168 A1 | 11/2008 | Wieland |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0018581 A1 | 1/2009 | Anderson et al. |
| 2009/0035722 A1 | 2/2009 | Balasundaram et al. |
| 2009/0036893 A1 | 2/2009 | Kartalian et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0088753 A1 | 4/2009 | Aram et al. |
| 2009/0088858 A1 | 4/2009 | Zinger et al. |
| 2009/0105772 A1 | 4/2009 | Seebeck et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0192621 A1 | 7/2009 | Winslow et al. |
| 2009/0198288 A1 | 8/2009 | Hoof et al. |
| 2009/0210057 A1 | 8/2009 | Liao et al. |
| 2009/0216268 A1 | 8/2009 | Panter |
| 2009/0216285 A1 | 8/2009 | Ek et al. |
| 2009/0220561 A1 | 9/2009 | Jin et al. |
| 2009/0222012 A1 | 9/2009 | Karnes et al. |
| 2009/0228031 A1 | 9/2009 | Ritter et al. |
| 2009/0228105 A1 | 9/2009 | Son et al. |
| 2009/0234452 A1 | 9/2009 | Steiner et al. |
| 2009/0254094 A1 | 10/2009 | Knapp et al. |
| 2009/0264889 A1 | 10/2009 | Long et al. |
| 2009/0264928 A1 | 10/2009 | Blain |
| 2009/0275950 A1 | 11/2009 | Sterrett et al. |
| 2009/0276052 A1 | 11/2009 | Regala et al. |
| 2009/0283701 A1 | 11/2009 | Ogawa |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0057197 A1 | 3/2010 | Weber et al. |
| 2010/0069958 A1 | 3/2010 | Sullivan et al. |
| 2010/0082035 A1 | 4/2010 | Keefer |
| 2010/0087829 A1 | 4/2010 | Metzger et al. |
| 2010/0092535 A1 | 4/2010 | Cook et al. |
| 2010/0112519 A1 | 5/2010 | Hall et al. |
| 2010/0136289 A1 | 6/2010 | Extrand et al. |
| 2010/0152752 A1 | 6/2010 | Denove et al. |
| 2010/0168505 A1 | 7/2010 | Inman et al. |
| 2010/0168854 A1 | 7/2010 | Luers et al. |
| 2010/0185294 A1 | 7/2010 | Ek |
| 2010/0191342 A1 | 7/2010 | Byrd et al. |
| 2010/0211071 A1 | 8/2010 | Lettmann et al. |
| 2010/0217315 A1 | 8/2010 | Jolly et al. |
| 2010/0227372 A1 | 9/2010 | Bilek et al. |
| 2010/0241236 A1 | 9/2010 | Katrana et al. |
| 2010/0249930 A1 | 9/2010 | Myers |
| 2010/0249935 A1 | 9/2010 | Slivka et al. |
| 2010/0249942 A1 | 9/2010 | Goswami et al. |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268238 A1 | 10/2010 | Sikora et al. |

(56) References Cited

U.S. PATENT DOCUMENTS

| | | |
|---|---|---|
| 2010/0268273 A1 | 10/2010 | Albertorio et al. |
| 2010/0268330 A1 | 10/2010 | Tong et al. |
| 2010/0268346 A1 | 10/2010 | Tong et al. |
| 2010/0268347 A1 | 10/2010 | Tong et al. |
| 2011/0009964 A1 | 1/2011 | Schwartz et al. |
| 2011/0035012 A1 | 2/2011 | Linares |
| 2011/0059312 A1 | 3/2011 | Howling et al. |
| 2011/0066242 A1 | 3/2011 | Lu et al. |
| 2011/0071641 A1 | 3/2011 | Ek et al. |
| 2011/0085968 A1 | 4/2011 | Jin et al. |
| 2011/0087280 A1 | 4/2011 | Albertorio |
| 2011/0093085 A1 | 4/2011 | Morton |
| 2011/0098822 A1 | 4/2011 | Walch et al. |
| 2011/0106271 A1 | 5/2011 | Regala et al. |
| 2011/0118780 A1 | 5/2011 | Holmes, Jr. |
| 2011/0123951 A1 | 5/2011 | Lomicka |
| 2011/0125263 A1 | 5/2011 | Webster et al. |
| 2011/0125277 A1 | 5/2011 | Nygren et al. |
| 2011/0137341 A1 | 6/2011 | Thornes et al. |
| 2011/0152869 A1 | 6/2011 | Ek et al. |
| 2011/0153023 A1 | 6/2011 | Deffenbaugh et al. |
| 2011/0159070 A1 | 6/2011 | Jin et al. |
| 2011/0178557 A1 | 7/2011 | Rush et al. |
| 2011/0190902 A1 | 8/2011 | Tong et al. |
| 2011/0196367 A1 | 8/2011 | Gallo |
| 2011/0213375 A1 | 9/2011 | Sikora et al. |
| 2011/0224729 A1 | 9/2011 | Baker et al. |
| 2011/0236435 A1 | 9/2011 | Biris |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301648 A1 | 12/2011 | Lofthouse et al. |
| 2011/0301716 A1 | 12/2011 | Sirivisoot et al. |
| 2012/0016428 A1 | 1/2012 | White et al. |
| 2012/0022656 A1 | 1/2012 | Lavi |
| 2012/0027837 A1 | 2/2012 | DeMuth et al. |
| 2012/0029647 A1 | 2/2012 | Winslow et al. |
| 2012/0051489 A1 | 3/2012 | Varanasi et al. |
| 2012/0058328 A1 | 3/2012 | Tourvieille et al. |
| 2012/0059418 A1 | 3/2012 | Denham et al. |
| 2012/0065732 A1 | 3/2012 | Roller et al. |
| 2012/0065734 A1 | 3/2012 | Barrett et al. |
| 2012/0071935 A1 | 3/2012 | Keith et al. |
| 2012/0101502 A1 | 4/2012 | Kartalian et al. |
| 2012/0109136 A1 | 5/2012 | Bourque et al. |
| 2012/0109222 A1 | 5/2012 | Goel et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0128666 A1 | 5/2012 | Pébay et al. |
| 2012/0150203 A1 | 6/2012 | Brady et al. |
| 2012/0150225 A1 | 6/2012 | Burkart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0214128 A1 | 8/2012 | Collins et al. |
| 2012/0215310 A1 | 8/2012 | Sharp et al. |
| 2012/0221111 A1 | 8/2012 | Burkhead, Jr. et al. |
| 2012/0253467 A1 | 10/2012 | Frankle |
| 2012/0265298 A1 | 10/2012 | Schmieding et al. |
| 2012/0323338 A1 | 12/2012 | Vanasse |
| 2012/0330322 A1 | 12/2012 | Sand et al. |
| 2012/0330357 A1 | 12/2012 | Thal |
| 2013/0006374 A1 | 1/2013 | Le Couedic et al. |
| 2013/0022943 A1 | 1/2013 | Collins et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Dryfuss et al. |
| 2013/0138150 A1 | 5/2013 | Baker et al. |
| 2013/0150885 A1 | 6/2013 | Dreyfuss |
| 2013/0150975 A1 | 6/2013 | Iannotti et al. |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |
| 2013/0184818 A1 | 7/2013 | Coughlin et al. |
| 2013/0190819 A1 | 7/2013 | Norton |
| 2013/0190885 A1 | 7/2013 | Ammann et al. |
| 2013/0197651 A1 | 8/2013 | McDaniel et al. |
| 2013/0204257 A1 | 8/2013 | Zajac |
| 2013/0204259 A1 | 8/2013 | Zajac |
| 2013/0205936 A1 | 8/2013 | Schmieding et al. |
| 2013/0218176 A1 | 8/2013 | Denove et al. |
| 2013/0218286 A1 | 8/2013 | Stahl Wernersson et al. |
| 2013/0237987 A1 | 9/2013 | Graham |
| 2013/0238099 A1 | 9/2013 | Hardy et al. |
| 2013/0245775 A1 | 9/2013 | Metcalfe |
| 2013/0261750 A1 | 10/2013 | Lappin |
| 2013/0268073 A1 | 10/2013 | Albertorio et al. |
| 2013/0282129 A1 | 10/2013 | Phipps |
| 2013/0289570 A1 | 10/2013 | Chao |
| 2013/0304209 A1 | 11/2013 | Schmieding et al. |
| 2013/0331886 A1 | 12/2013 | Thornes |
| 2013/0338722 A1 | 12/2013 | Yalizis |
| 2013/0338792 A1 | 12/2013 | Schmieding et al. |
| 2013/0344600 A1 | 12/2013 | Jin et al. |
| 2013/0345747 A1 | 12/2013 | Dreyfuss |
| 2013/0345748 A1 | 12/2013 | Dreyfuss |
| 2014/0012267 A1 | 1/2014 | Skiora et al. |
| 2014/0012389 A1 | 1/2014 | Ek |
| 2014/0025173 A1 | 1/2014 | Cardon et al. |
| 2014/0052178 A1 | 2/2014 | Dooney, Jr. |
| 2014/0052179 A1 | 2/2014 | Dreyfuss et al. |
| 2014/0066933 A1 | 3/2014 | Ek et al. |
| 2014/0074164 A1 | 3/2014 | Dreyfuss et al. |
| 2014/0074239 A1 | 3/2014 | Albertorio et al. |
| 2014/0079921 A1 | 3/2014 | De Volder |
| 2014/0081273 A1 | 3/2014 | Sherman |
| 2014/0081399 A1 | 3/2014 | Roller et al. |
| 2014/0088601 A1 | 3/2014 | Kuczynski |
| 2014/0088602 A1 | 3/2014 | Ammann et al. |
| 2014/0114322 A1 | 4/2014 | Perez, III |
| 2014/0114367 A1 | 4/2014 | Jolly et al. |
| 2014/0121700 A1 | 5/2014 | Dreyfuss et al. |
| 2014/0121701 A1 | 5/2014 | Dreyfuss et al. |
| 2014/0128889 A1 | 5/2014 | Sullivan et al. |
| 2014/0128915 A1 | 5/2014 | Dreyfuss et al. |
| 2014/0128921 A1 | 5/2014 | Parsons et al. |
| 2014/0155902 A1 | 6/2014 | Sikora et al. |
| 2014/0188232 A1 | 7/2014 | Metcalfe et al. |
| 2014/0194880 A1 | 7/2014 | Schmieding et al. |
| 2014/0228849 A1 | 8/2014 | Sterrett et al. |
| 2014/0236306 A1 | 8/2014 | Karnes et al. |
| 2014/0243439 A1 | 8/2014 | Papangelou et al. |
| 2014/0243891 A1 | 8/2014 | Schmieding et al. |
| 2014/0243892 A1 | 8/2014 | Choinski |
| 2014/0243976 A1 | 8/2014 | Schmieding et al. |
| 2014/0257297 A1 | 9/2014 | Koogle, Jr. et al. |
| 2014/0257299 A1 | 9/2014 | Berelsman et al. |
| 2014/0257384 A1 | 9/2014 | Dreyfuss et al. |
| 2014/0276841 A1 | 9/2014 | Albertorio et al. |
| 2014/0276990 A1 | 9/2014 | Perez, III |
| 2014/0277020 A1 | 9/2014 | Koogle et al. |
| 2014/0277121 A1 | 9/2014 | Pilgeram et al. |
| 2014/0277134 A1 | 9/2014 | ElAttrache et al. |
| 2014/0277181 A1 | 9/2014 | Garlock |
| 2014/0277186 A1 | 9/2014 | Granberry et al. |
| 2014/0277214 A1 | 9/2014 | Helenbolt et al. |
| 2014/0277448 A1 | 9/2014 | Guerra et al. |
| 2014/0288657 A1 | 9/2014 | Lederman et al. |
| 2014/0309689 A1 | 10/2014 | Sikora et al. |
| 2014/0324167 A1 | 10/2014 | Schmieding et al. |
| 2014/0335145 A1 | 11/2014 | Jin et al. |
| 2014/0350688 A1 | 11/2014 | Michel et al. |
| 2015/0073424 A1 | 3/2015 | Couture et al. |

(56) References Cited

U.S. PATENT DOCUMENTS

| | | |
|---|---|---|
| 2015/0134066 A1 | 5/2015 | Bachmaier |
| 2015/0142052 A1 | 5/2015 | Koogle, Jr. et al. |
| 2015/0157462 A1 | 6/2015 | Ek et al. |
| 2015/0164648 A1 | 6/2015 | Lizak et al. |
| 2015/0201951 A1 | 7/2015 | Bradley et al. |
| 2015/0216541 A1 | 8/2015 | Schmieding et al. |
| 2015/0245831 A1 | 9/2015 | Sullivan |
| 2015/0250472 A1 | 9/2015 | Ek et al. |
| 2015/0250475 A1 | 9/2015 | Ek |
| 2015/0250594 A1 | 9/2015 | Ek |
| 2015/0250602 A1 | 9/2015 | Sikora et al. |
| 2015/0265328 A1 | 9/2015 | Viola |
| 2015/0313586 A1 | 11/2015 | Burkhart et al. |
| 2016/0022374 A1 | 1/2016 | Haider et al. |
| 2016/0030035 A1 | 2/2016 | Zajac et al. |
| 2016/0051268 A1 | 2/2016 | Seitlinger et al. |
| 2016/0051367 A1 | 2/2016 | Gervasi et al. |
| 2016/0106444 A1 | 4/2016 | Ek |
| 2016/0151060 A1 | 6/2016 | Albertorio et al. |
| 2016/0151119 A1 | 6/2016 | Michel et al. |
| 2016/0287243 A1 | 10/2016 | Benedict et al. |
| 2016/0287266 A1 | 10/2016 | Sikora et al. |
| 2016/0310132 A1 | 10/2016 | Meislin et al. |
| 2016/0331404 A1 | 11/2016 | Jolly et al. |
| 2016/0354197 A1 | 12/2016 | Roller et al. |
| 2017/0056180 A1 | 3/2017 | Schmieding |
| 2017/0100251 A1 | 4/2017 | Ek et al. |
| 2017/0119528 A1 | 5/2017 | Ek et al. |
| 2017/0128085 A1 | 5/2017 | Sikora et al. |
| 2017/0209196 A1 | 7/2017 | Zajac et al. |
| 2017/0215935 A1 | 8/2017 | Taft |
| 2017/0239696 A1 | 8/2017 | Weber |
| 2017/0252147 A1 | 9/2017 | Albertorio et al. |
| 2017/0252521 A1 | 9/2017 | Guerra et al. |
| 2017/0281200 A1 | 10/2017 | Sikora et al. |
| 2017/0296328 A1 | 10/2017 | Albertorio et al. |
| 2017/0311983 A1 | 11/2017 | Sikora et al. |
| 2017/0333020 A1 | 11/2017 | Laviano et al. |
| 2018/0055507 A1 | 3/2018 | Bachmaier et al. |
| 2018/0085104 A1 | 3/2018 | Schmieding et al. |
| 2018/0085109 A1 | 3/2018 | Petry et al. |
| 2018/0103963 A1 | 4/2018 | Bradley et al. |
| 2018/0116682 A1 | 5/2018 | Albertorio et al. |
| 2018/0132869 A1 | 5/2018 | Sikora et al. |
| 2018/0154041 A1 | 6/2018 | Altschuler et al. |
| 2018/0161169 A1 | 6/2018 | Cardon et al. |
| 2018/0344447 A1 | 12/2018 | Albertorio et al. |
| 2019/0021719 A1 | 1/2019 | Dooney et al. |
| 2019/0029836 A1 | 1/2019 | Ek |
| 2019/0038426 A1 | 2/2019 | Ek |
| 2019/0059910 A1 | 2/2019 | Adams et al. |
| 2019/0105160 A1 | 4/2019 | Ek et al. |
| 2019/0105165 A1 | 4/2019 | Sikora et al. |
| 2019/0105166 A1 | 4/2019 | Ek et al. |
| 2019/0201185 A1 | 7/2019 | Albertorio et al. |
| 2019/0239902 A1 | 8/2019 | Sikora et al. |
| 2019/0350578 A1 | 11/2019 | Petry et al. |
| 2020/0046383 A1 | 2/2020 | Ek |
| 2020/0155174 A1 | 5/2020 | Sikora et al. |
| 2020/0275960 A1 | 9/2020 | Ek et al. |
| 2020/0323544 A1 | 10/2020 | Sikora et al. |
| 2021/0022877 A1 | 1/2021 | Ek |
| 2021/0030549 A1 | 2/2021 | Ek et al. |
| 2021/0030550 A1 | 2/2021 | Ek et al. |
| 2021/0038395 A1 | 2/2021 | Ek et al. |
| 2021/0038398 A1 | 2/2021 | Sikora et al. |

FOREIGN PATENT DOCUMENTS

| | | | |
|---|---|---|---|
| AU | 2002248198 B2 | 5/2007 | |
| AU | 2005202099 B2 | 6/2007 | |
| AU | 2002357284 B2 | 8/2007 | |
| AU | 2006202337 B2 | 5/2008 | |
| AU | 2003262428 | 8/2009 | |
| AU | 2007216648 B2 | 11/2009 | |
| AU | 2004216106 B2 | 6/2010 | |
| AU | 2008207536 B2 | 3/2011 | |
| CA | 2759027 | 10/2010 | |
| CA | 2470194 C | 2/2011 | |
| DE | 2933174 | 4/1980 | |
| DE | 3516743 | 11/1986 | |
| DE | 3840466 | 6/1990 | |
| DE | 19505083 | 11/1995 | |
| DE | 102004053606 | 5/2006 | |
| DE | 112013003358 | 3/2015 | |
| EP | 0240004 | 10/1987 | |
| EP | 0241240 | 10/1987 | |
| EP | 0290736 | 11/1988 | |
| EP | 0350780 | 1/1990 | |
| EP | 0485678 | 5/1992 | |
| EP | 0327387 | 9/1992 | |
| EP | 0505634 | 9/1992 | |
| EP | 0736292 | 10/1996 | |
| EP | 0903125 | 3/1999 | |
| EP | 0903127 | 3/1999 | |
| EP | 0993812 | 4/2000 | |
| EP | 0661023 | 8/2001 | |
| EP | 1374782 | 1/2004 | |
| EP | 1426013 | 9/2004 | |
| EP | 1870060 | 12/2007 | |
| EP | 1927328 | 6/2008 | |
| EP | 1278460 | 4/2009 | |
| EP | 2062541 | 5/2009 | |
| EP | 2455002 | 5/2012 | |
| EP | 2314257 | 2/2013 | |
| EP | 2572650 | 3/2013 | |
| EP | 2574313 A1 * | 4/2013 | ........... A61F 2/4003 |
| EP | 2689750 A1 | 1/2014 | |
| EP | 2595534 | 6/2014 | |
| EP | 2804565 | 10/2014 | |
| EP | 2481368 | 12/2014 | |
| EP | 2901971 A1 | 8/2015 | |
| EP | 2986232 | 2/2016 | |
| EP | 2 400 930 | 12/2017 | |
| EP | 2986232 | 11/2018 | |
| FR | 2242068 | 3/1975 | |
| FR | 2642301 | 3/1990 | |
| FR | 2676917 | 12/1992 | |
| FR | 2693650 | 1/1994 | |
| FR | 2718014 | 10/1995 | |
| FR | 2733904 | 11/1996 | |
| FR | 2739151 | 3/1997 | |
| GB | 2281577 | 3/1995 | |
| GB | 2372707 | 9/2002 | |
| JP | 61502029 | 9/1986 | |
| JP | 63300758 | 12/1988 | |
| JP | 3504932 | 10/1991 | |
| JP | H03-092328 | 11/1992 | |
| JP | 518511 | 3/1993 | |
| JP | 06339490 | 12/1994 | |
| JP | 11244315 | 9/1999 | |
| JP | 2964035 | 10/1999 | |
| JP | 2001525210 | 12/2001 | |
| JP | 2002291779 | 10/2002 | |
| JP | 2003534096 | 11/2003 | |
| WO | 198803781 | 6/1988 | |
| WO | 8909578 | 10/1989 | |
| WO | 9409730 | 5/1994 | |
| WO | 9427507 | 12/1994 | |
| WO | 9624304 | 8/1996 | |
| WO | 1997022306 | 6/1997 | |
| WO | 199725006 | 7/1997 | |
| WO | 9920192 | 4/1999 | |
| WO | 0013597 | 3/2000 | |
| WO | 0105336 | 1/2001 | |
| WO | 0166021 | 9/2001 | |
| WO | 0166022 | 9/2001 | |
| WO | 0182677 | 11/2001 | |
| WO | 0191648 | 12/2001 | |
| WO | 0191672 | 12/2001 | |
| WO | 0217821 | 3/2002 | |
| WO | 02086180 | 10/2002 | |
| WO | 03047470 | 6/2003 | |
| WO | 03051210 | 6/2003 | |

(56) References Cited

FOREIGN PATENT DOCUMENTS

| | | |
|---|---|---|
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2004100839 | 11/2004 |
| WO | 2005051231 | 6/2005 |
| WO | 2006004885 | 1/2006 |
| WO | 2006074321 | 7/2006 |
| WO | 2006091686 | 8/2006 |
| WO | 2010135156 | 11/2010 |
| WO | 2012003548 | 1/2012 |
| WO | 2012021857 | 2/2012 |
| WO | 2012058349 | 5/2012 |
| WO | 2013064569 A1 | 5/2013 |
| WO | 2013152102 | 10/2013 |
| WO | 2014008126 | 1/2014 |
| WO | 2014172347 | 10/2014 |
| WO | 2016154393 | 9/2016 |
| WO | 2019028344 | 2/2019 |
| WO | 2019079104 A2 | 4/2019 |
| WO | 2020092335 | 5/2020 |

OTHER PUBLICATIONS

Office Action dated Dec. 21, 2018, issued in U.S. Appl. No. 15/388,808, 7 pages.
Notice of Allowance dated Jan. 22, 2019, issued in U.S. Appl. No. 15/296,772, 7 pages.
Office Action dated Mar. 1, 2019, issued in U.S. Appl. No. 15/388,808, 9 pages.
Office Action dated Apr. 2, 2019, issued in U.S. Appl. No. 13/723,902, 19 pages.
Office Action dated Apr. 10, 2019, issued in U.S. Appl. No. 15/865,734, 8 pages.
Office Action dated May 9, 2019, issued in U.S. Appl. No. 15/943,949, 8 pages.
Office Action dated May 15, 2019, issued in U.S. Appl. No. 14/640,667, 16 pages.
Office Action dated May 15, 2019, issued in U.S. Appl. No. 15/973,981, 6 pages.
Office Action dated Jun. 4, 2019, issued in U.S. Appl. No. 14/133,943, 13 pages.
Notice of Allowance dated Jun. 11, 2019, issued in Canadian Patent Application No. 2,759,027, 1 page.
Examination Report dated Jul. 2, 2019, issued in Brazilian Patent Application No. PI1014961-9, 2 pages.
Notice of Allowance dated Jul. 15, 2019, issued in U.S. Appl. No. 15/606,643, 5 pages.
Notice of Allowance dated Sep. 10, 2019, issued in U.S. Appl. No. 15/388,808, 8 pages.
Office Action dated Sep. 11, 2019, issued in U.S. Appl. No. 15/351,530, 15 pages.
VILEX—Restoring Mobility, Cannulated Implants for Forefoot Joints, QSD 8.12-11 Rev D, 2010, 4 pages.
Tornier Implants Chirurgicaux—Aequalis Reversed Shoulder Prosethesis, K132285, Dec. 5, 2013, 8 pages.
Tornier, Aequalis Reversed II Shoulder, Nov. 2014, 3 pages.
Johnson & Johnson Medical Devices Companies—Global PA Shoulder System, https://www.depuysynthes.com/hcp/shoulder/products/qs/DELTAXTEND-Reverse-Shoulder-System, Nov. 2014, 7 pages.
Zimmer Biomet—Joint Replacement Orthopaedic Devices_Hip_Knee_Shoulder, http://www.biomet.com/orthopedics/getfile.cfm?id=2905&rt=inline, Nov. 2014, 3 pages.
Notice of allowance dated Oct. 28, 2019, issued in U.S. Appl. No. 15/865,734, 7 pages.
Office Action dated Nov. 19, 2019, issued in U.S. Appl. No. 13/723,902, 16 pages.
Notice of allowance dated Dec. 12, 2019, issued in U.S. Appl. No. 15/388,808, 8 pages.
Notice of allowance dated Dec. 16, 2019, issued in U.S. Appl. No. 15/973,981, 8 pages.
Notice of allowance dated Dec. 17, 2019, issued in U.S. Appl. No. 15/943,949, 7 pages.
Notice of allowance dated Dec. 18, 2019, issued in U.S. Appl. No. 14/133,943, 5 pages.
Office Action dated Dec. 30, 3019, issued in U.S. Appl. No. 15/943,956, 16 pages.
Office Action dated Jan. 16, 2020, issued in U.S. Appl. No. 14/640,667, 10 pages.
International Search Report and Written Opinion dated Jan. 16, 2020, issued in PCT International Patent Application No. PCT/US2019/058517, 9 pages.
Office Action dated Dec. 16, 2019, issued in European Patent Application No. 05 763 817.3, 5 pages.
Preliminary Report on Patentability dated Feb. 13, 2020, issued in PCT Patent Application No. PCT/US2018/045157, 5 pages.
Notice of Allowance dated Feb. 24, 2020, issued in U.S. Appl. No. 15/351,530, 8 pages.
Office Action dated Mar. 16, 2020, issued in U.S. Appl. No. 15/079,342, 16 pages.
International Search Report and Written Opinion dated Apr. 8, 2020, issued in PCT Patent Application No. PCT/US2020/014980, 9 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance dated Sep. 26, 2003 in U.S. Appl. No. 10/162,533.
USPTO Notice of Allowance dated May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance dated Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patent application No. 2005202099.
AU Examiners report dated Jan. 12, 2007 issued in corresponding Australian patent application No. 2006202337.
AU Examiners report dated Feb. 21, 2007 issued in corresponding Australian patent application No. 2005202099.
AU Examiners report dated May 23, 2007 issued in corresponding Australian patent application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).

(56) References Cited

OTHER PUBLICATIONS

EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
U.S. Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28, 2014, issued in U.S. Appl. No. 13/752,858, 8 pages.
U.S. Office Action dated Jun. 4, 2014, issued in U.S. Appl. No. 12/762,920, 10 pages.
Notice of Allowance dated Jun. 19, 2014, issued in U.S. Appl. No. 13/470,678, 5 pages.
Intent to Grant dated Jun. 27, 2014, issued in European Patent Application No. 12 002 103.5, 6 pages.
U.S. Office Action dated Jul. 7, 2014, issued in U.S. Appl. No. 12/979,992, 6 pages.
U.S. Office Action dated Jul. 7, 2014, issued in U.S. Appl. No. 12/001,473, 15 pages.
Partial supplementary European search report dated Mar. 25, 2015, issued in EP Patent Application No. 11751521.3, 6 pages.
U.S. Examiner interview summary dated Apr. 8, 2015, issued in U.S. Appl. No. 12/001,473, 4 pages.
U.S. Final Office Action dated Apr. 16, 2015, issued in U.S. Appl. No. 12/762,920, 15 pages.
U.S. Supplemental Notice of Allowance dated Apr. 21, 2015, issued in U.S. Appl. No. 13/436,188, 6 pages.
U.S. Final Office Action dated Apr. 28, 2015, issued in U.S. Appl. No. 13/785,867, 8 pages.
U.S. Office Action dated May 1, 2015, issued in U.S. Appl. No. 14/133,943, 25 pages.
U.S. Final Office Action dated May 22, 2015, issued in U.S. Appl. No. 13/438,095, 7 pages.
U.S. Final Office Action dated Jun. 2, 2015, issued in U.S. Appl. No. 12/001,473, 18 pages.
U.S. Office Action dated Jun. 25, 2015, issued in U.S. Appl. No. 12/711,039, 10 pages.
U.S. Final Office Action dated Jul. 7, 2015, issued in U.S. Appl. No. 12/762,948, 15 pages.
Intent to Grant dated Jul. 8, 2015, issued in European Patent Application No. 08 729 178.7, 7 pages.
Notice of Allowance dated Jul. 31, 2015, issued in U.S. Appl. No. 13/438,095, 8 pages.
Extended Search Report dated Sep. 9, 2015, issued in European Patent Application No. 11751521.3, 13 pages.
U.S. Final Office Action dated Sep. 17, 2015, issued in U.S. Appl. No. 14/035,061, 10 pages.
International Preliminary Report on Patentability dated Oct. 29, 2015, issued in PCT Patent Application No. PCT/US/2014/034157, 5 pages.
European Examination Report dated Oct. 28, 2015, issued in European Patent Application No. 05 763 817.3, 4 pages.
U.S. Notice of Allowance dated Oct. 30, 2015, issued in U.S. Appl. No. 12/762,920, 8 pages.
Partial Supplementary European Search Report dated Nov. 5, 2015, issued in European Patent Application No. 12860168.9, 6 pages.
U.S. Office Action dated Nov. 17, 2015, issued in U.S. Appl. No. 13/930,737, 9 pages.
U.S. Office Action dated Nov. 25, 2015, issued in U.S. Appl. No. 13/723,902, 13 pages.
U.S. Office Action dated Nov. 25, 2015, issued in U.S. Appl. No. 13/863,917, 12 pages.
European Examination Report dated Dec. 7, 2015, issued in European Patent Application No. 10 765 332.1, 4 pages.
U.S. Office Action dated Dec. 8, 2015, issued in U.S. Appl. No. 13/796,675, 16 pages.
European Decision to Grant dated Dec. 17, 2015, issued in European Patent Application No. 08729178.7, 2 pages.
European Examination Report dated Jul. 22, 2015, issued in European Patent Application No. 09 002 088.4, 4 pages.
U.S. Office Action dated Jan. 21, 2016, issued in U.S. Appl. No. 12/762,948, 14 pages.

(56) References Cited

OTHER PUBLICATIONS

U.S. Final Office Action dated Jan. 21, 2016, issued in U.S. Appl. No. 14/133,943, 27 pages.
U.S. Notice of Allowance dated Feb. 8, 2016, issued in U.S. Appl. No. 13/785,867, 8 pages.
U.S. Notice of Allowance dated Feb. 12, 2016, issued in U.S. Appl. No. 12/001,473, 14 pages.
Canadian Office Action dated Feb. 15, 2016, issued in Canadian Patent Application No. 2,407,440, 3 pages.
U.S. Notice of Allowability dated Feb. 17, 2016, issued in U.S. Appl. No. 13/785,867, 4 pages.
U.S. Notice of Allowance dated Feb. 17, 2016, issued in U.S. Appl. No. 12/979,992, 5 pages.
U.S. Final Office Action dated Feb. 25, 2016, issued in U.S. Appl. No. 12/711,039, 7 pages.
European Extended Search Report dated Feb. 29, 2016, issued in European Patent Application No. 12860168.9, 11 pages.
Canadian Examiner Requisition dated Mar. 10, 2016, issued in Canadian Patent Application No. 2,759,027, 3 pages.
European Examination Report dated Mar. 21, 2016, issued in European Patent Application No. 10 746 863.9, 3 pages.
U.S. Office Action dated Mar. 22, 2016, issued in U.S. Appl. No. 14/640,602, 8 pages.
U.S. Office Action dated Jun. 2, 2016, issued in U.S. Appl. No. 14/035,061, 9 pages.
U.S. Notice of Allowance dated Jun. 7, 2016, issued in U.S. Appl. No. 13/930,737, 5 pages.
International Search Report and Written Opinion dated Jun. 10, 2016, issued in PCT Patent Application No. PCT/US2016/023930, 13 pages.
U.S. Notice of Allowance dated Jun. 29, 2016, issued in U.S. Appl. No. 13/863,917, 9 pages.
U.S. Final Office Action dated Jul. 6, 2016, issued in U.S. Appl. No. 13/723,902, 15 pages.
Official Communication dated Jun. 21, 2016, issued in European Patent Application No. 11 751 521.3, 3 pages.
Final Office Action dated Jul. 19, 2016, issued in U.S. Appl. No. 13/796,675, 17 pages.
Official Communication dated Aug. 23, 2016, issued in European Patent Application No. 10 765 332.1, 4 pages.
Office Action dated Sep. 8, 2016, issued in U.S. Appl. No. 14/640,529, 15 pages.
Office Action dated Sep. 20, 2016, issued in U.S. Appl. No. 14/133,943, 24 pages.
Final Office Action dated Sep. 30, 2016, issued in U.S. Appl. No. 14/640,602, 5 pages.
Office Action dated Oct. 10, 2016, issued in European Patent Application No. 10 746 863.9, 4 pages.
Extended Search Report dated Nov. 16, 2016, issued in European Patent Application No. 14785702.3, 7 pages.
Office Action dated Nov. 22, 2016, issued in U.S. Appl. No. 14/640,774, 10 pages.
Office Action dated Nov. 24, 2016, issued in European Patent Application No. 12 860 168.9, 4 pages.
Office Action dated Dec. 1, 2016, issued in European Patent Application No. 05 763 817.3, 3 pages.
Notice of Allowance dated Jan. 27, 2017, issued in U.S. Appl. No. 12/762,948, 5 pages.
Office Action dated Jan. 27, 2017, issued in U.S. Appl. No. 14/035,061, 9 pages.
Office Action dated Feb. 7, 2017, issued in U.S. Appl. No. 13/723,902, 16 pages.
Office Action dated Feb. 22, 2017, issued in U.S. Appl. No. 13/796,675, 19 pages.
Final Office Action dated Mar. 28, 2017, issued in U.S. Appl. No. 14/133,943, 29 pages.
Canadian Office Action dated Jan. 9, 2017, issued in Canadian Patent Application No. 2,759,027, 3 pages.
Canadian Office Action dated Mar. 22, 2017, issued in Canadian Patent Application No. 2,407,440, 7 pages.
U.S. Notice of Allowance dated Apr. 14, 2017, issued in U.S. Appl. No. 14/640,602, 7 pages.
U.S. Office Action dated Apr. 28, 2017, issued in U.S. Appl. No. 15/153,113, 11 pages.
U.S. Final Office Action dated May 9, 2017, issued in U.S. Appl. No. 14/640,529, 15 pages.
U.S. Final Office Action dated Jun. 15, 2017, issued in U.S. Appl. No. 14/640,774, 10 pages.
Notice of Allowance dated Aug. 7, 2017, issued in U.S. Appl. No. 14/640,602, 8 pages.
Office Action dated Aug. 25, 2017, issued in U.S. Appl. No. 14/728,216, 10 pages.
Final Office Action dated Aug. 25, 2017, issued in U.S. Appl. No. 14/035,061, 10 pages.
Final Office Action dated Sep. 22, 2017, issued in U.S. Appl. No. 13/723,902, 21 pages.
Preliminary Report on Patentability dated Oct. 5, 2017, issued in PCT Patent Application No. PCT/US2016/023930, 11 pages.
Intent to Grant dated Oct. 6, 2017, issued in European Patent Application No. 11 751 521.3, 7 pages.
Final Office Action dated Oct. 6, 2017, issued in U.S. Appl. No. 13/796,675, 18 pages.
Intent to Grant dated Oct. 6, 2017, issued in European Patent Application No. 12 860 168.9, 7 pages.
Office Action dated Oct. 16, 2017, issued in European Patent Application No. 05 763 817.3, 5 pages.
Office Action dated Oct. 17, 2017, issued in U.S. Appl. No. 14/640,667, 10 pages.
Office Action dated Oct. 16, 2017, issued in Canadian Patent Application No. 2,759,027, 3 pages.
U.S. Notice of Allowance dated Nov. 30, 2017, issued in U.S. Appl. No. 14/640,529, 7 pages.
European Intent to Grant dated Dec. 1, 2017, issued in European Patent Application Serial No. 09 002 088.4, 6 pages.
U.S. Notice of Allowance dated Dec. 8, 2017, issued in U.S. Appl. No. 15/153,113, 5 pages.
U.S. Office Action dated Dec. 12, 2017, issued in U.S. Appl. No. 14/133,943, 28 pages.
Canadian Notice of Allowance dated Dec. 14, 2017, issued in Canadian Patent Application Serial No. 2,407,440, 1 page.
U.S. Notice of Allowance dated Jan. 10, 2018, issued in U.S. Appl. No. 14/640,774, 8 pages.
U.S. Notice of Allowance dated Apr. 16, 2018, issued in U.S. Appl. No. 15/153,170, 10 pages.
Office Action dated May 16, 2018, issued in U.S. Appl. No. 15/388,808, 7 pages.
U.S. Notice of Allowance dated May 16, 2018, issued in U.S. Appl. No. 14/728,216, 5 pages.
Office Action dated May 31, 2018, issued in U.S. Appl. No. 13/723,902, 15 pages.
Office Action dated Jun. 19, 2018, issued in U.S. Appl. No. 15/296,772, 8 pages.
Office Action dated Jun. 29, 2018, issued in U.S. Appl. No. 14/640,667, 11 pages.
Office Action dated Sep. 5, 2018, issued in U.S. Appl. No. 15/606,643, 6 pages.
Office Action dated Sep. 13, 2018, issued in U.S. Appl. No. 14/133,943, 28 pages.
International Search Report and Written Opinion dated Oct. 23, 2018, issued in PCT Patent Application No. PCT/US18/45157, 11 pages.
Office Action dated Nov. 9, 2018, issued in Canadian Patent Application No. 2,759,027, 4 pages.
Notice of Allowance dated Dec. 3, 2020, issued in U.S. Appl. No. 16/101,620, 10 pages.
Office Action dated Feb. 12, 2021, issued in U.S. Appl. No. 16/430,947, 8 pages.
International Search Report and Written Opinion dated May 22, 2020, issued in PCT Patent Application No. PCT/U2020/022464, 12 pages.
European Office Action dated Apr. 16, 2013 issued in European Patent Application No. 12 002 103.5, 5 pages.

(56) References Cited

OTHER PUBLICATIONS

U.S. Applicant Initiated Interview Summary dated May 15, 2013 issued in U.S. Appl. No. 12/762,920, 3 pages.
European Office Action dated May 15, 2013 issued in European Patent Application No. 05 763 817.3, 4 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
Decision to Grant dated Sep. 19, 2013 issued in European Patent Application No. 07862736.1, 1 page.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Nov. 29, 2013 issued in U.S. Appl. No. 12/762,920, 9 pages.
U.S. Final Office Action dated Dec. 5, 2013 issued in U.S. Appl. No. 13/470,678, 8 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014, issued in U.S. Appl. No. 12/711,039, 17 pages.
European Examination Report dated Mar. 20, 2014, issued in European Patent Application No. 12 002 103.5, 3 pages.
U.S. Office Action dated Mar. 21, 2014, issued in U.S. Appl. No. 12/942,923, 6 pages.
U.S. Notice of Allowance dated Apr. 1, 2014, issued in U.S. Appl. No. 13/470,678, 7 pages.
Australian Examination Report dated Apr. 3, 2014, issued in Australian Patent Application No. 2010217907, 3 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.
U.S. Office Action dated Sep. 18, 2014, issued in U.S. Appl. No. 13/785,867, 8 pages.
U.S. Notice of Allowance dated Oct. 6, 2014, issued in U.S. Appl. No. 12/942,923, 5 pages.
U.S. Office Action issued in U.S. Appl. No. 13/438,095, dated Nov. 4, 2014, 11 pages.
International Search Report and Written Opinion issued in PCT Patent Application Serial No. PCT/US14/34157, dated Nov. 4, 2014, 12 pages.
European Extended Search Report issued in European Patent Application Serial No. 10765332.1, dated Nov. 10, 2014, 6 pages.
U.S. Office Action issued in U.S. Appl. No. 12/711,039, dated Nov. 10, 2014, 10 pages.
European Extended Search Report issued in European Patent Application Serial No. 10746863.9, dated Nov. 13, 2014, 5 pages.
European Decision to Grant issued in European Patent Application Serial No. 12002103.5, dated Nov. 20, 2014, 1 page.
European Office Action issued in European Patent Application No. 08 729 178.7, dated Nov. 25, 2014, 4 pages.
U.S. Notice of Allowance issued in U.S. Appl. No. 13/037,929, dated Dec. 11, 2014, 5 pages.
International Preliminary Report on Patentability dated Jan. 15, 2015, issued in PCT Patent Application No. PCT/US2013/048569, 9 pages.
Notice of Allowance dated Jan. 21, 2015, issued in U.S. Appl. No. 13/752,858, 7 pages.
Notice of Allowability dated Feb. 19, 2015, issued in U.S. Appl. No. 13/037,929, 2 pages.
U.S. Office Action dated Feb. 19, 2015, issued in U.S. Appl. No. 14/035,061, 6 pages.
Notice of Allowance dated Feb. 25, 2015, issued in U.S. Appl. No. 13/436,188, 8 pages.
Canadian Office Action dated Feb. 27, 2015 issued in Canadian Patent Application Serial No. 2,407,440, 7 pages.
Office Action dated Mar. 3, 2015, issued in U.S. Appl. No. 12/979,992, 11 pages.
Sullivan, "HALLUX RIGIDUS: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.

(56) References Cited

OTHER PUBLICATIONS

Notice of Allowance dated Feb. 20, 2009 issued in related U.S. Appl. No. 10/618,887.
Notice of Reasons for Rejection issued in related Japanese Patent Application No. 2003-394702 dated Jul. 21, 2009.
Notice of Reasons for Rejection issued in related Japanese Patent Application No. 20-541615 dated May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.

(56) References Cited

OTHER PUBLICATIONS

Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
Habermeyer, Peter, Atos News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Themen, (16 pages).
Gray, Henry, Anatomy of the Human Body, 1918, 6d. The Foot 1. The Tarsus, II. Osteology, cover page and 10 pgs, www.Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vilex, (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).
M. Siguier, MD et al, "Preliminary Results of Partial Surface Replacement of the Femoral Head in Osteonecrosis", The Journal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knee Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral head", An Experimental Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Bale, MD, Reto J., et al, "Osteochondral Lesions of the Talus: Computer=assisted Retrograde Drilling Feasibility and Accuracy in Initial Experiences[1]", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug. 2001):pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, a service of the National Library of Medicine and the National Institutes of Health, Foot Ankle Int.Aug. 1999; 20(8):474-80.
Ueblacker, M.D., Peter, et al, "Retrograde Cartilage Transplantation of the Proximal and Distal Tibia", Arthroscopy: The Journal of Arthroscopic and Related Surgery, vol. 20, No. 1 (Jan. 2004): pp. 73-78.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.

(56) References Cited

OTHER PUBLICATIONS

USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice Of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthroplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Jäger, et al., "Partial hemi-resurfacing of the hip joint—a new approach to treat local osteochondral defects?" Biomed Tech 2006; 51:371-376 (2006).
Office Action dated Sep. 2, 2020, issued in U.S. Appl. No. 14/640,667, 12 pages.
Office Action dated Sep. 23, 2020, issued in U.S. Appl. No. 15/943,956, 13 pages.
International Search Report and Written Opinion dated Oct. 2, 2020, issued in PCT International Patent Application No. PCT/US2020/037492, 12 pages.

(56) References Cited

OTHER PUBLICATIONS

Office Action dated Oct. 15, 2020, issued in European Patent Application No. 05763817.2, 3 pages.
Office Action dated Nov. 3, 2020, issued in U.S. Appl. No. 16/134,291, 7 pages.
Notice of Allowance dated Nov. 3, 2020, issued in U.S. Appl. No. 15/079,342, 7 pages.
Office Action dated Nov. 25, 2020, issued in U.S. Appl. No. 16/054,224, 12 pages.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowability dated Oct. 9, 2012, issued in U.S. Appl. No. 12/713,135, 5 pages.
Notice of Allowability dated Oct. 11, 2012, issued in U.S. Appl. No. 11/169,326 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31, 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
Extended European Search report dated Dec. 10, 2012 issued in European Patent Application No. 07844549.1, 5 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
U.S. Office Action dated Feb. 25, 2013 issued in U.S. Appl. No. 12/762,920, 8 pages.
Canadian Office Action dated Dec. 13, 2012 issued in Canadian Patent Application No. 2,407,440, 6 pages.
International Search Report and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. No. 12/762,948, 10 pages.
Canadian Office Action dated Jul. 28, 2021, received in Canadian Patent Application No. 3,064,646, 3 pages.
Canadian Office Action dated Dec. 29, 2021, received in Canadian Patent Application No. 3,064,646, 3 pages.
European Office Action dated Jan. 14, 2022, received in European Patent Application No. 16 769 660.8, 6 pages.
Examination Report under Section 18(3) dated May 13, 2022, received in European Patent Application No. GB2112996.0, 2 pages.

* cited by examiner

FIG. 13A
FIG. 13B
FIG. 13C
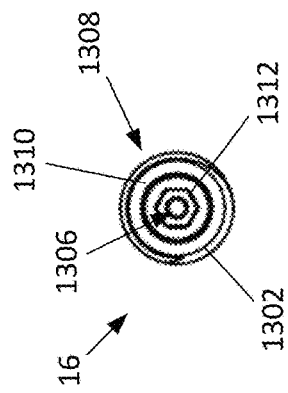
FIG. 13D
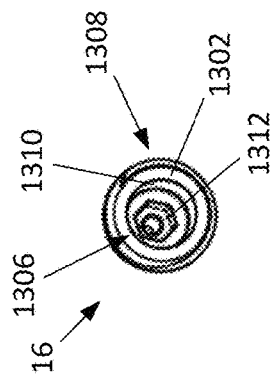
FIG. 13E
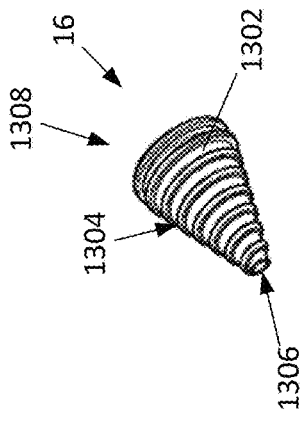
FIG. 13F

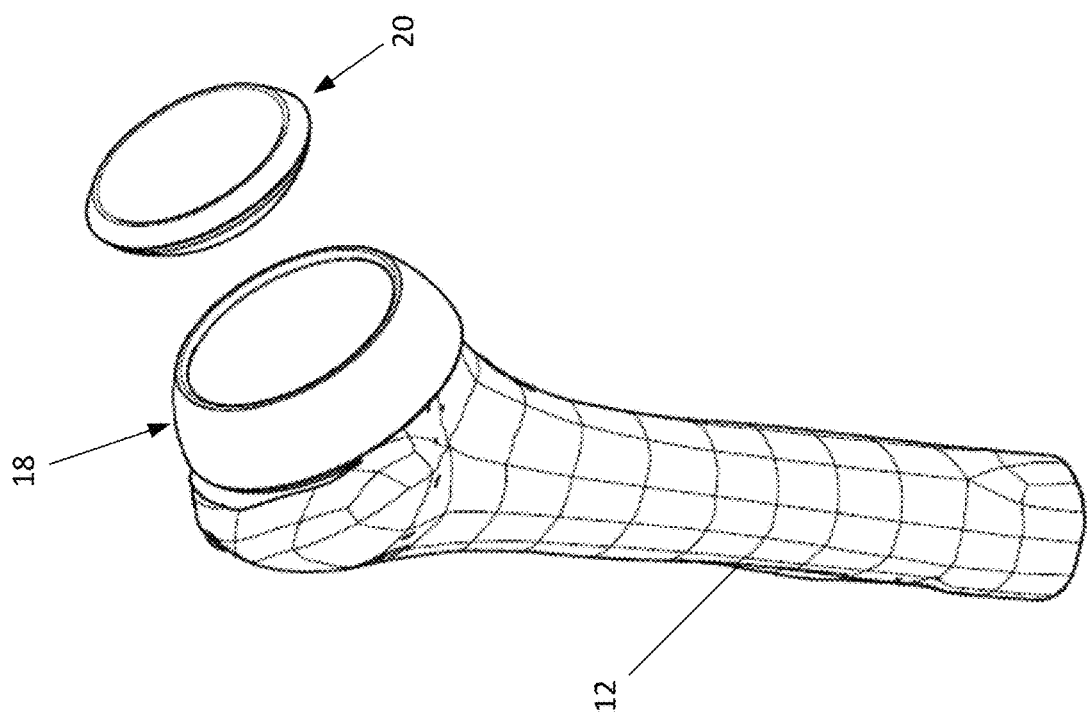

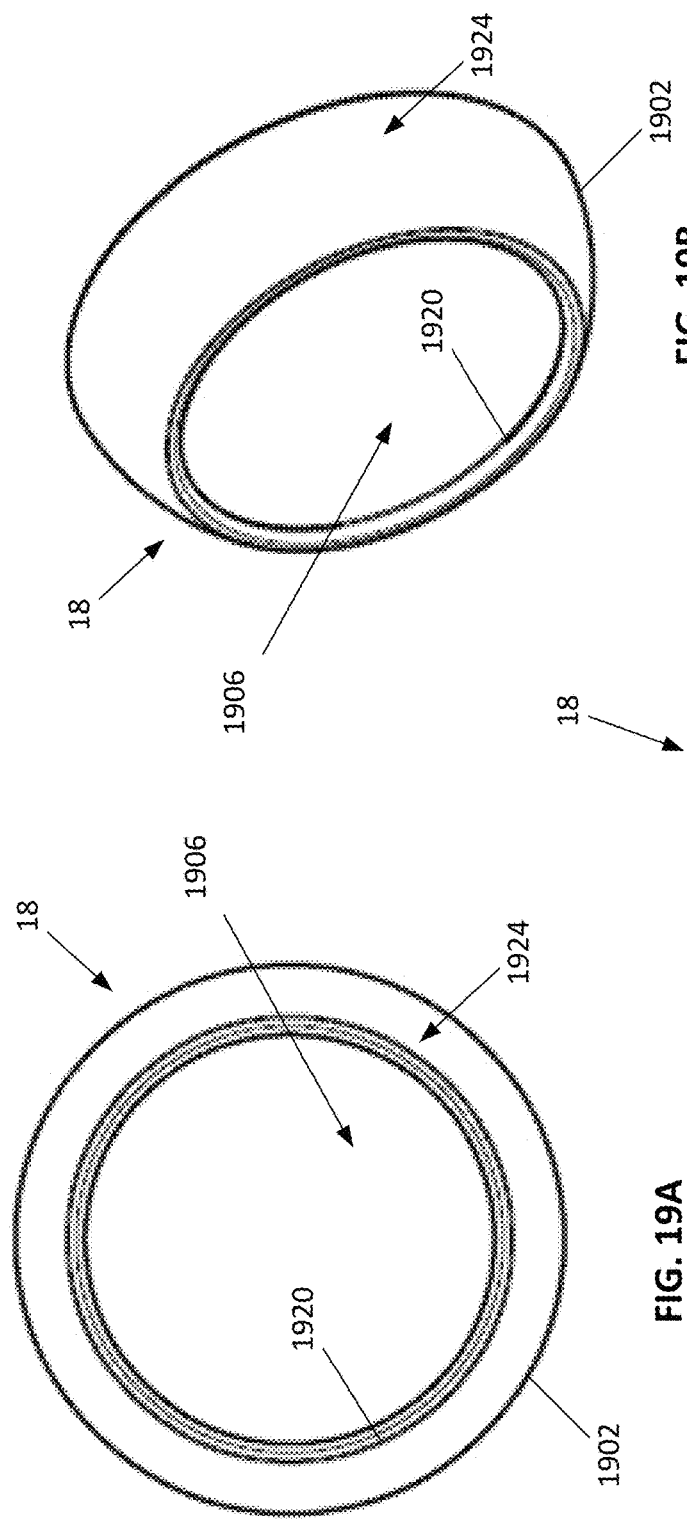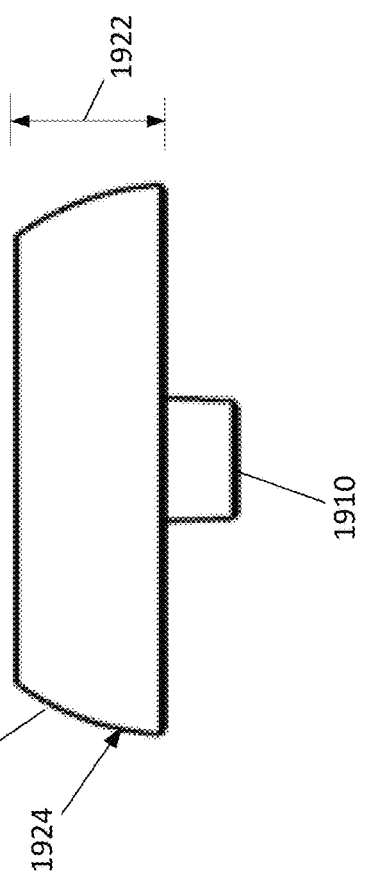
FIG. 19B
FIG. 19C
FIG. 19A

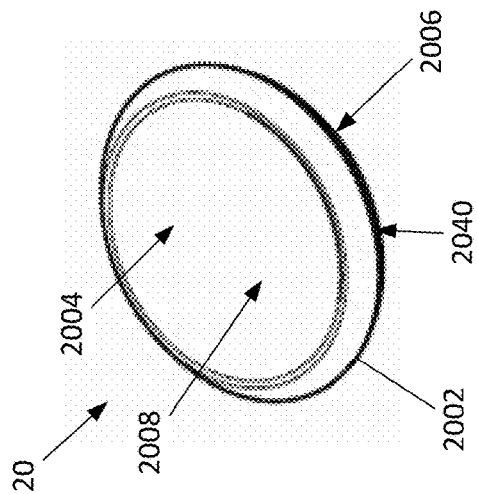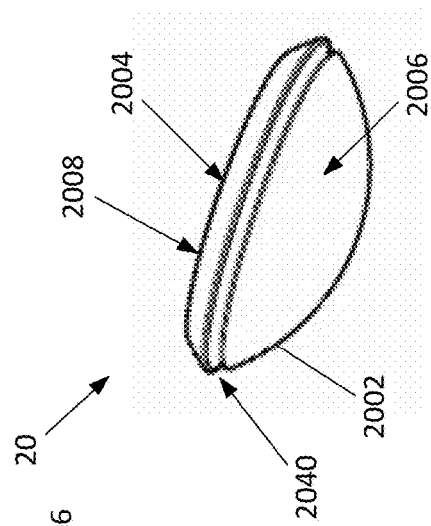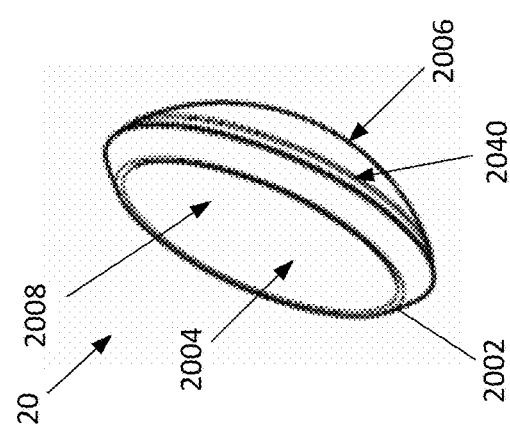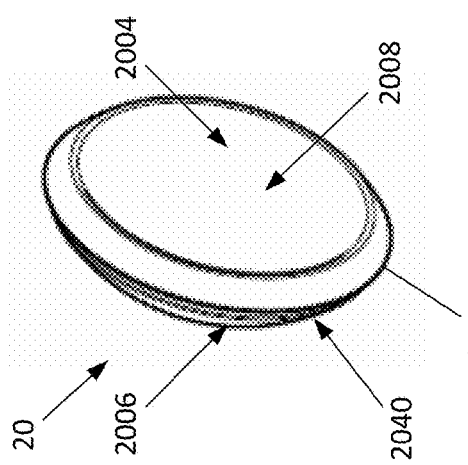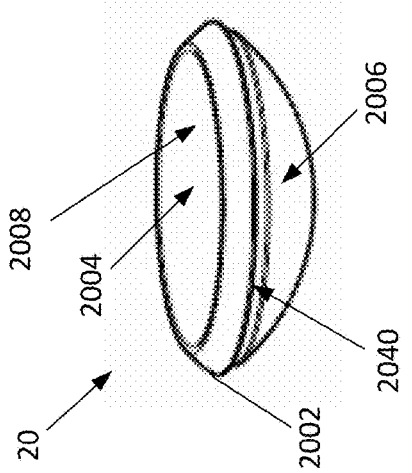

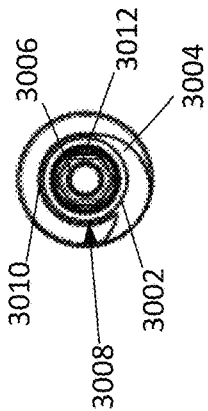
FIG. 30A
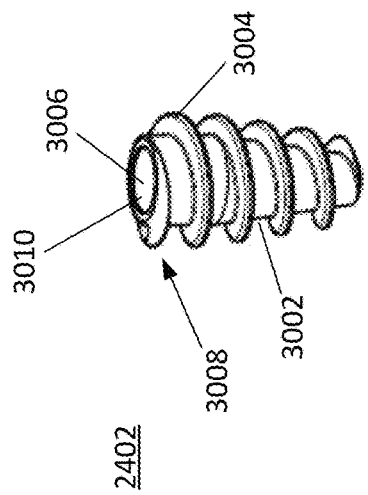
FIG. 30D
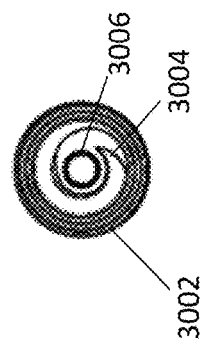
FIG. 30B
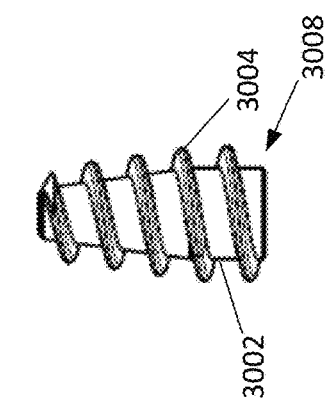
FIG. 30C
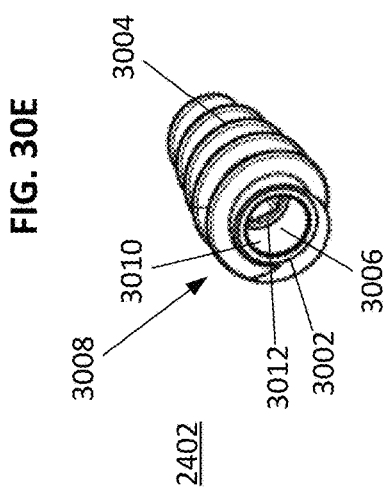
FIG. 30E
FIG. 30F

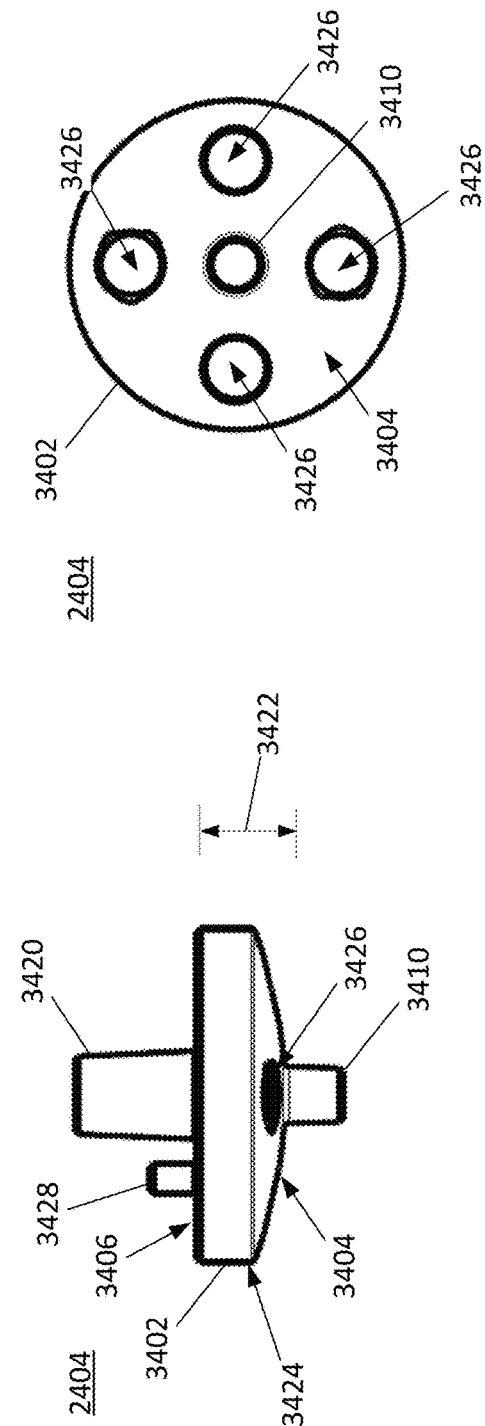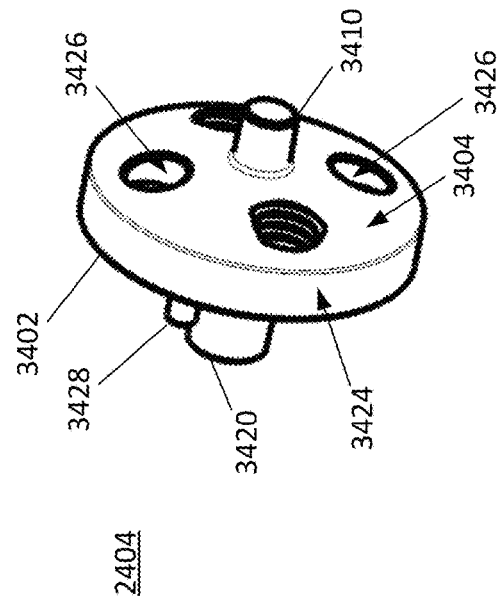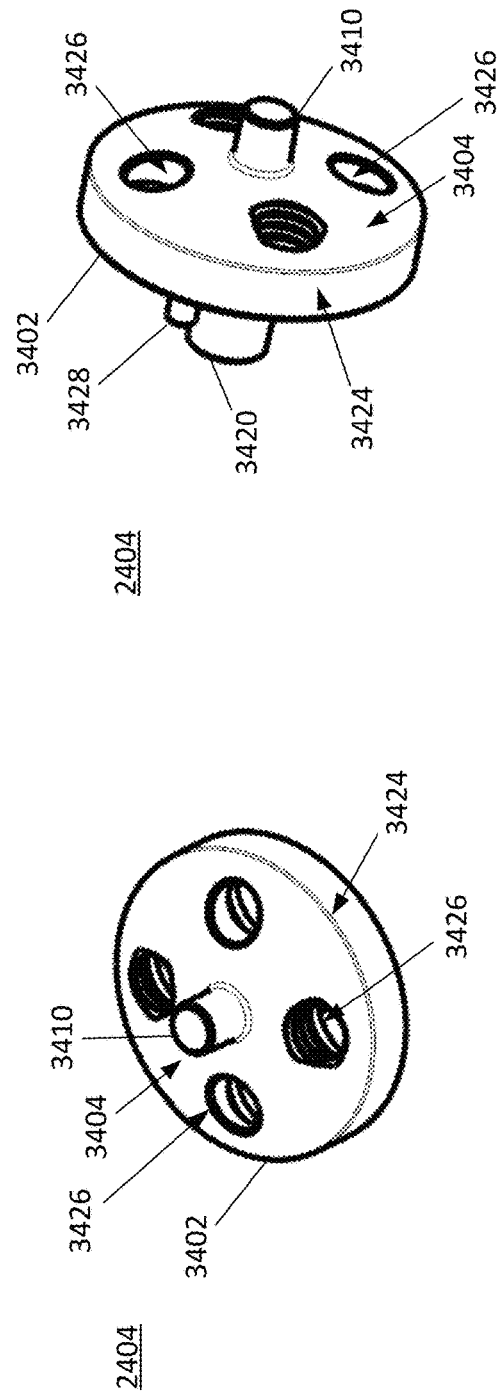

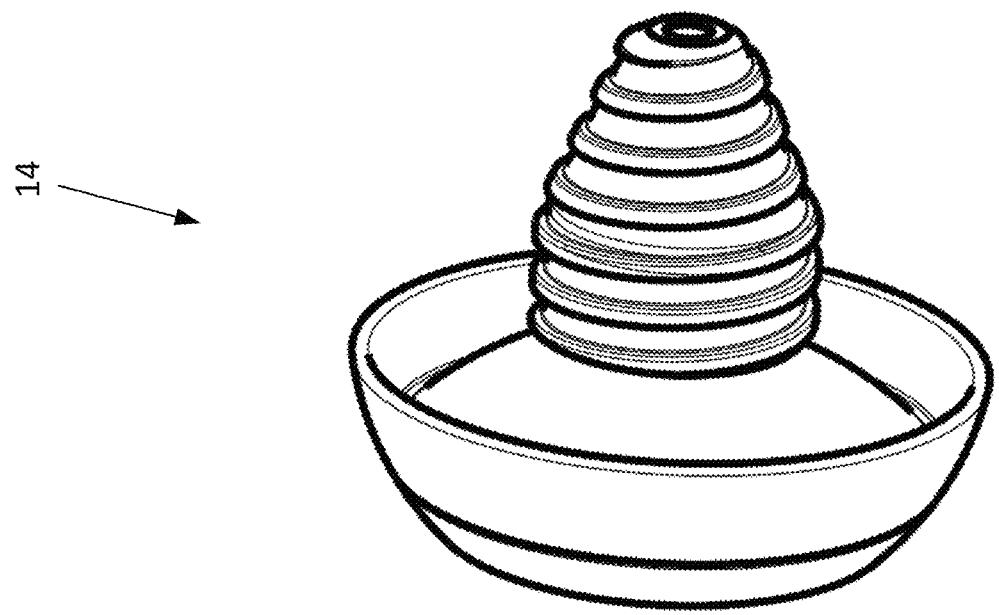
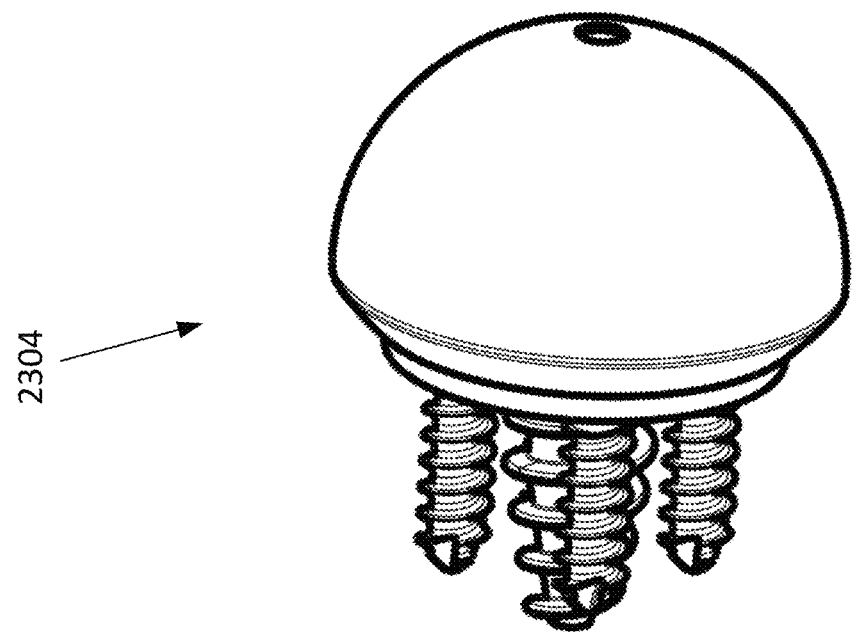
FIG. 47

HUMERAL AND GLENOID ARTICULAR SURFACE IMPLANT SYSTEMS AND METHODS

This application claims the benefit of, and priority to, U.S. Provisional Application Ser. No. 62/817,497, filed Mar. 12, 2019, which is hereby incorporated by reference in its entirety.

FIELD

The present disclosure is related to devices and methods for the repair of defects that occur in articular cartilage on the surface of bones, and particularly to systems and methods for repairing the humeral head and/or glenoid.

BACKGROUND

Articular cartilage, found at the ends of articulating bones in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspect of native hyaline cartilage and tends to be less durable.

In some cases, it may be necessary or desirable to repair the damaged articular cartilage using one or more implants. While implants may be successfully used, the implant should be designed to maximize the patient's comfort, minimize damage to surrounding areas, minimize potential further injury, maximize the functional life of the implant, and be easy to install.

BRIEF DESCRIPTION OF THE DRAWINGS

Features and advantages of the present invention are set forth by description of embodiments consistent with the present invention, which description should be considered in conjunction with the accompanying drawings wherein:

FIGS. 13A-F generally illustrate various views of one example of the anchor consistent with the present disclosure;

FIG. 18 generally illustrates one example of a tray secured to the anchor and a liner consistent with the present disclosure;

FIGS. 19A-E generally illustrate various views of one example of the tray consistent with the present disclosure;

FIGS. 20A-H generally illustrate various views of one example of the liner consistent with the present disclosure;

FIGS. 30A-F generally illustrate various views of one example of the anchor consistent with the present disclosure;

FIGS. 34A-G generally illustrate various views of one example of the baseplate consistent with the present disclosure;

FIGS. 43-49 generally illustrate various examples of the first implant system and the second implant system.

DETAILED DESCRIPTION

Figure 1:
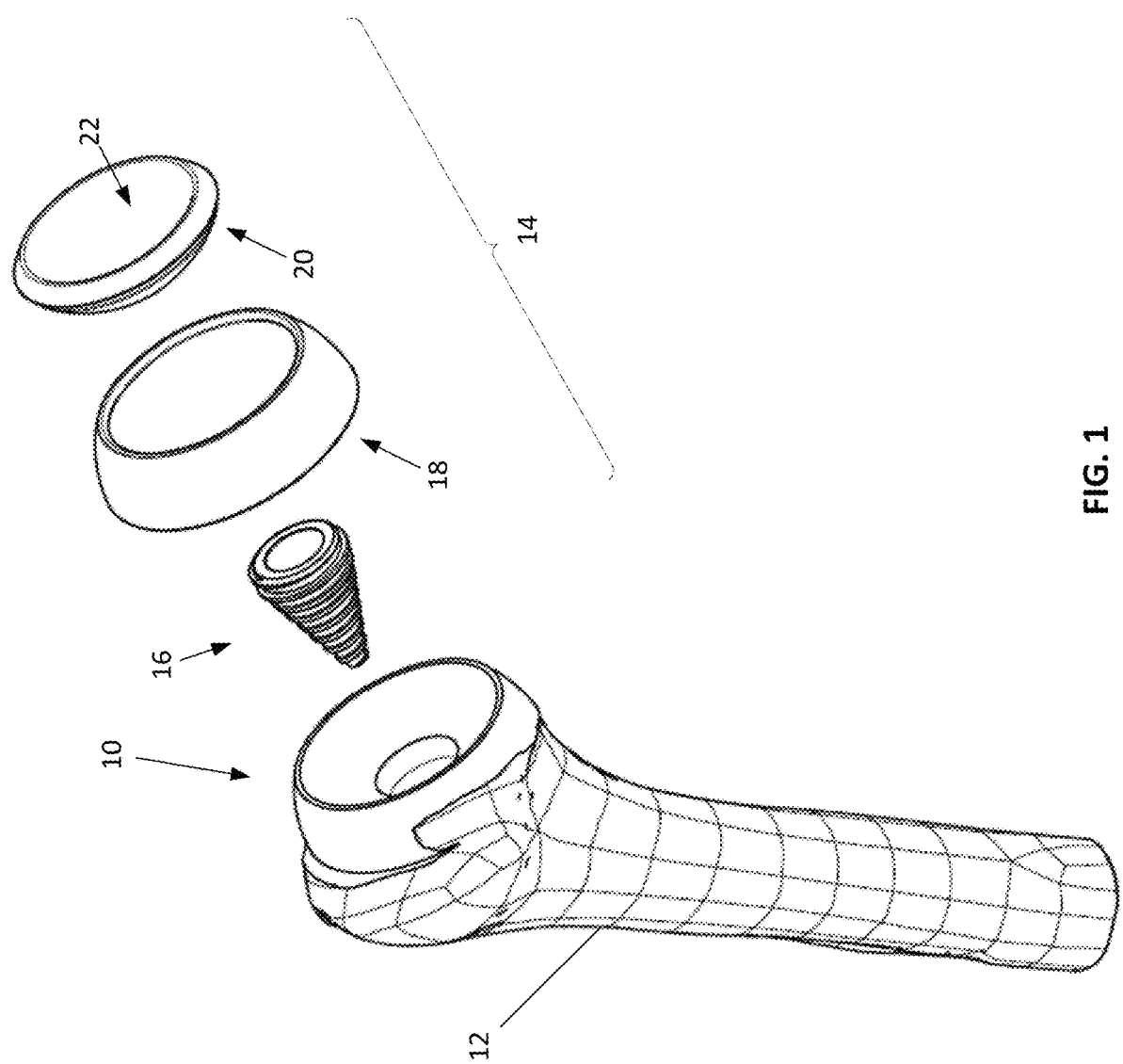
FIG. 1 generally illustrates one example of a first implant system and first excision site consistent with the present disclosure.

With reference to FIG. 1, a non-limiting example of a first implant site 10 formed in a first bone 12 and a first implant system 14 is generally illustrated. While aspects/embodiments of the first implant site 10 and the first implant system 14 may be described in the context of a humeral excision site formed in the humeral bone and a humeral implant system, it should be appreciated that the first implant site 10 may be formed in other bones (e.g., other than the humerus 12) and the first implant system 14 is not limited to a humeral implant system. As such, the systems and method described herein may be used to form a first implant site 10 on any bone 12 and the first implant system 14 may be used to repair/replace the articular surface of any bone 12.

The humeral implant site 10 may be formed in the humerus 12 in such a manner to aid in the positioning of the humeral implant system 14 and to reduce and/or prevent movement of the humeral implant system 14 relative to the humerus 12. At least a portion of the humeral implant site 10 may therefore be formed with a shape/contour/profile that inversely corresponds to the shape/contour/profile of at least a portion of the humeral implant system 14. As described herein, the humeral implant system 14 may include an anchor 16, an intermediate component or tray 18, and an implant or liner 20. The anchor 16 may be configured to be secured to the bone 12 within the humeral implant site 10, the tray 18 may be configured to be secured to the anchor 16, and the liner 20 may be configured to be secured to the tray 18. As shown, the liner 20 includes a load bearing surface 22 having a generally concaved surface contour (e.g., a reverse shoulder). While aspects/embodiments of the humeral implant system 14 may be described in the context of a reverse shoulder, it should be appreciated that the humeral implant system 14 is not limited to a reverse shoulder configuration. As such, the humeral implant system 14 may include a load bearing surface 22 having any shape/contour/profile such as, but no limited to, a shape/contour/profile that corresponds to the patient's original, native shape/contour/profile.

Figure 2:
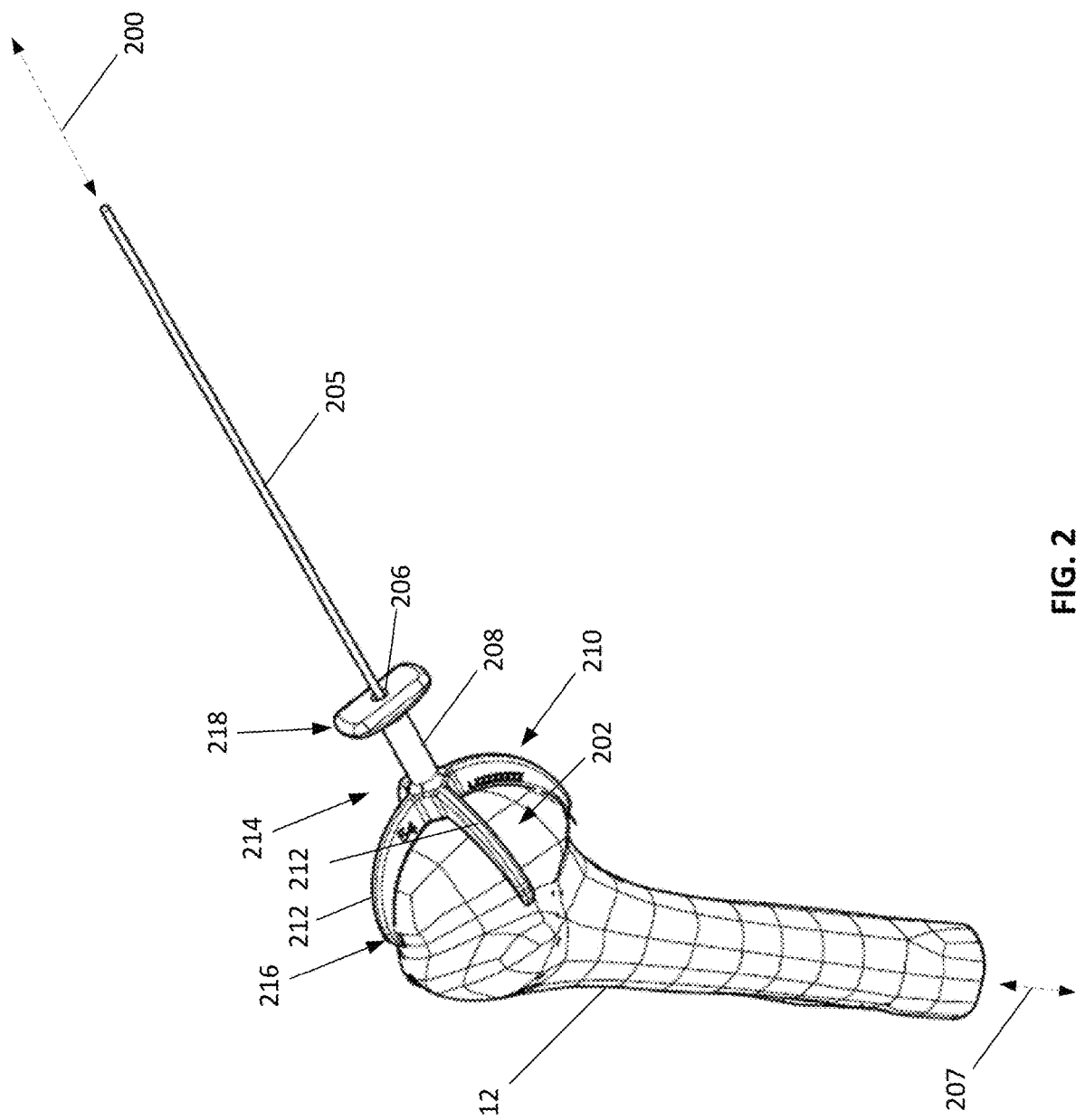
FIG. 2 generally illustrates one example of establishing a working axis consistent with the present disclosure.

Turning now to FIG. 2, a portion of one example of a system and method for forming the humeral implant site 10 in the humerus 12 to mate with the humeral implant system 14 is generally illustrated. In particular, a working axis 200 may be established. In the illustrated example, the working axis 200 extends at an angle normal to the crown or highest point on the patient's native articular surface 202; however, it should be appreciated that the working axis 200 may extend at any angle (which may be greater than or less than 90 degrees) and/or from any point along the patient's native articular surface 202. The crown or highest point on the patient's native articular surface 202 may be defined at the point on the patient's native articular surface 202 that is furthest away from the longitudinal axis 207 of the bone 12.

The working axis 200 may be established using a guide 204. The guide 204 may define a passageway 206 formed in a guide body 208 extending along the working axis 200. The passageway 206 may be configured to receive one or more pins 205 such that the pin 205 may be advanced through the passageway 206 and secured into the bone 12 along the working axis 200, for example, using a drill or the like (not shown for clarity). The passageway 206 may substantially correspond to the cross-section (e.g., diameter) of the outside of the pin 205 to align the pin 205 along the working axis 200. The depth that the pin 205 is secured into the bone 12 may be set using the guide 202. For example, the pin 205 and/or the guide 202 may include indicia (such as, but not limited to, laser markings, windows, shoulders, or the like) that may set the depth of the pin 205 into the bone 12.

The guide body 208 may include one or more locating features 210 such as, but not limited to, arms 212. The locating features 210 may be configured to contact native articular surface 202 and align/position the passageway 206 relative to the native articular surface 202. For example, the arms 212 may include tips 214 configured to engage and/or contact specific points of the humerus 12. The arms 212 may therefore have sizes and/or shapes based on the size and/or shape of the patient. The arms 212 may extend in one or more planes. For example, the arms 212 may extend in two mutually perpendicular planes. In one example, the arms 212 may be configured to substantially continuously contact against the native articular surface 202 along one or more planes; however, it should be appreciated that the arms 212 may only contact a plurality of discrete points (such as, but not limited to, the tips 216). The guide 202 may also optionally include a handle 218 configured to allow a surgeon to grasp and position the guide 202 relative to the native articular surface 202.

Figure 3:
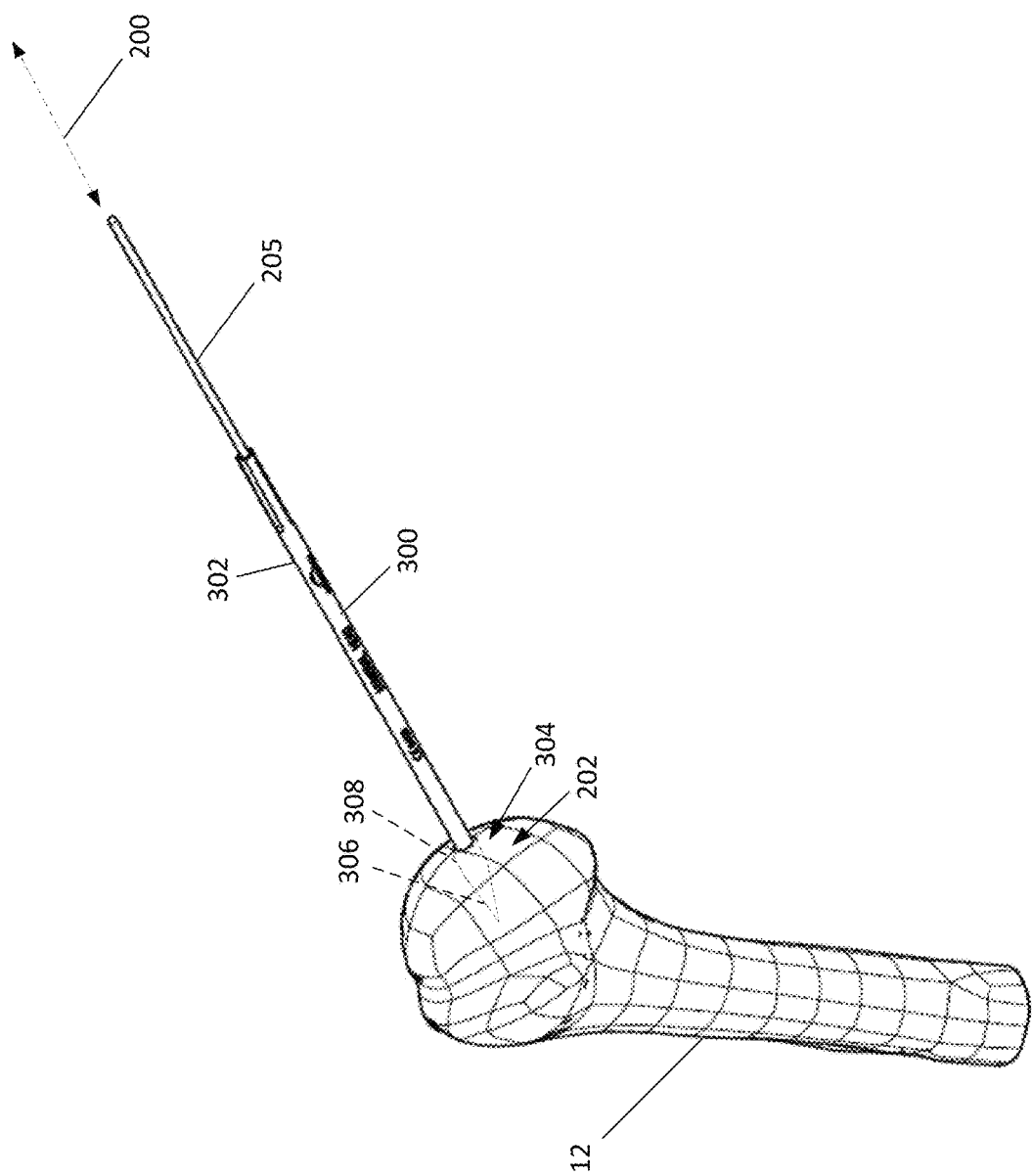
FIG. 3 generally illustrates one example of pin and a threaded instrument along the working axis consistent with the present disclosure.

Once the pin 205 is secured to the bone 12 along the working axis 200, the guide 202 may be removed. Next, a cannulated threaded instrument 300, FIG. 3, may be advanced over the pin 205 and secured into the bone 12. The cannulated threaded instrument 300 may include a cannulated shaft 302 and a distal end region 304 having a threaded tip 306 configured to be secured into the bone 12. The distal end region 304 may also include a shoulder 308. The shoulder 308 may extend radially outward beyond the cross-section (e.g., diameter) of the shaft 302. The cross-section (e.g., diameter) of the passageway 310 of the cannulated threaded instrument 300 may substantially correspond to the cross-section (e.g., diameter) of the outside of the pin 205. The depth that the cannulated threaded instrument 300 is secured into the bone 12, and thus the shoulder 308 relative to the native articular surface 202, may be set using the pin 205. For example, the cannulated threaded instrument 300 and/or the pin 205 may include indicate (such as, but not limited to, laser markings, windows, shoulders, or the like) that may set the depth of the cannulated threaded instrument 300 into the bone 12. In one example, the top of the shoulder 308 may be set to be substantially flush with the native articular surface 202 surrounding the cannulated threaded instrument 300.

Figure 4:
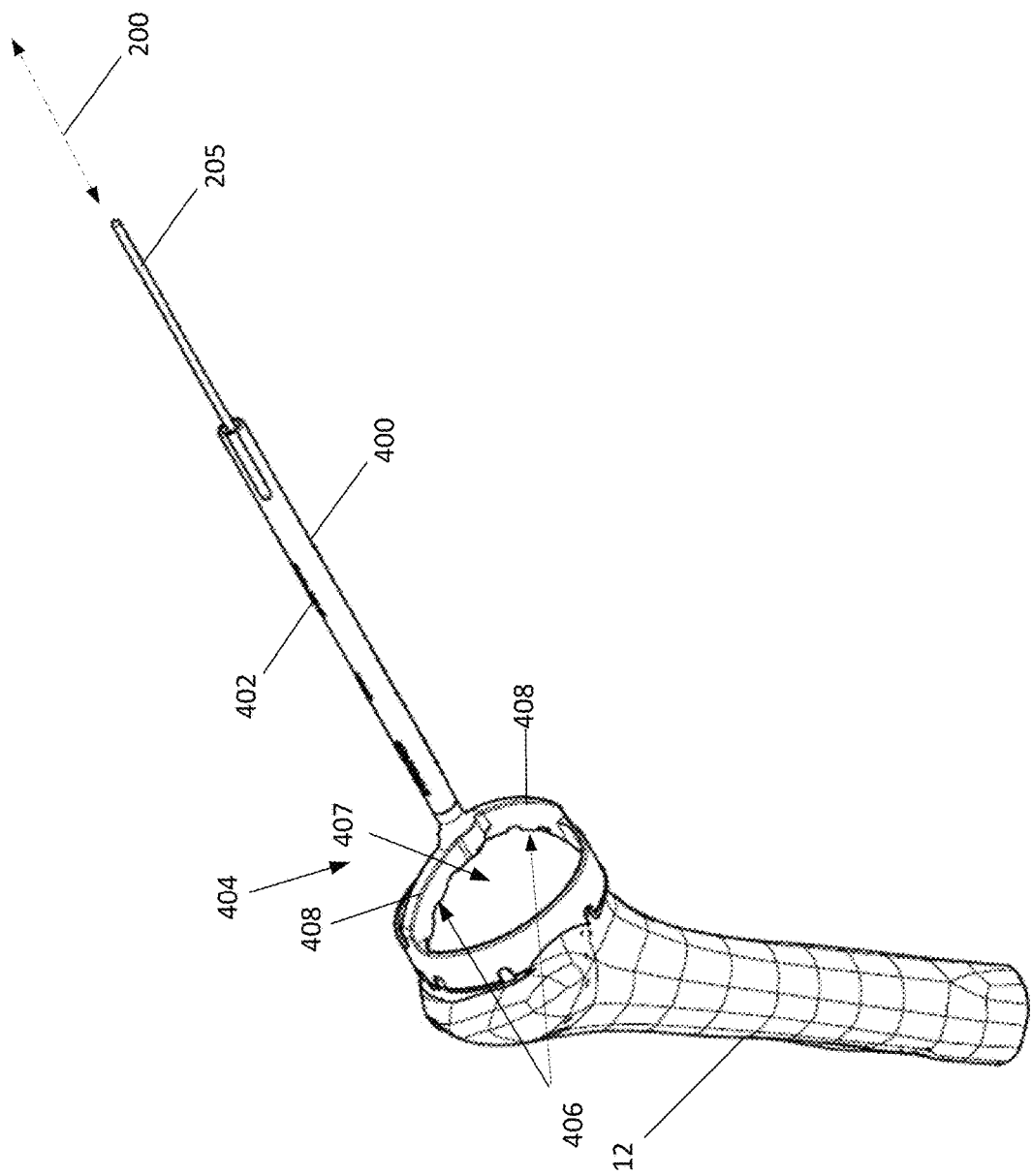
FIG. 4 generally illustrates one example of first reamer along the working axis consistent with the present disclosure.
Figure 5:
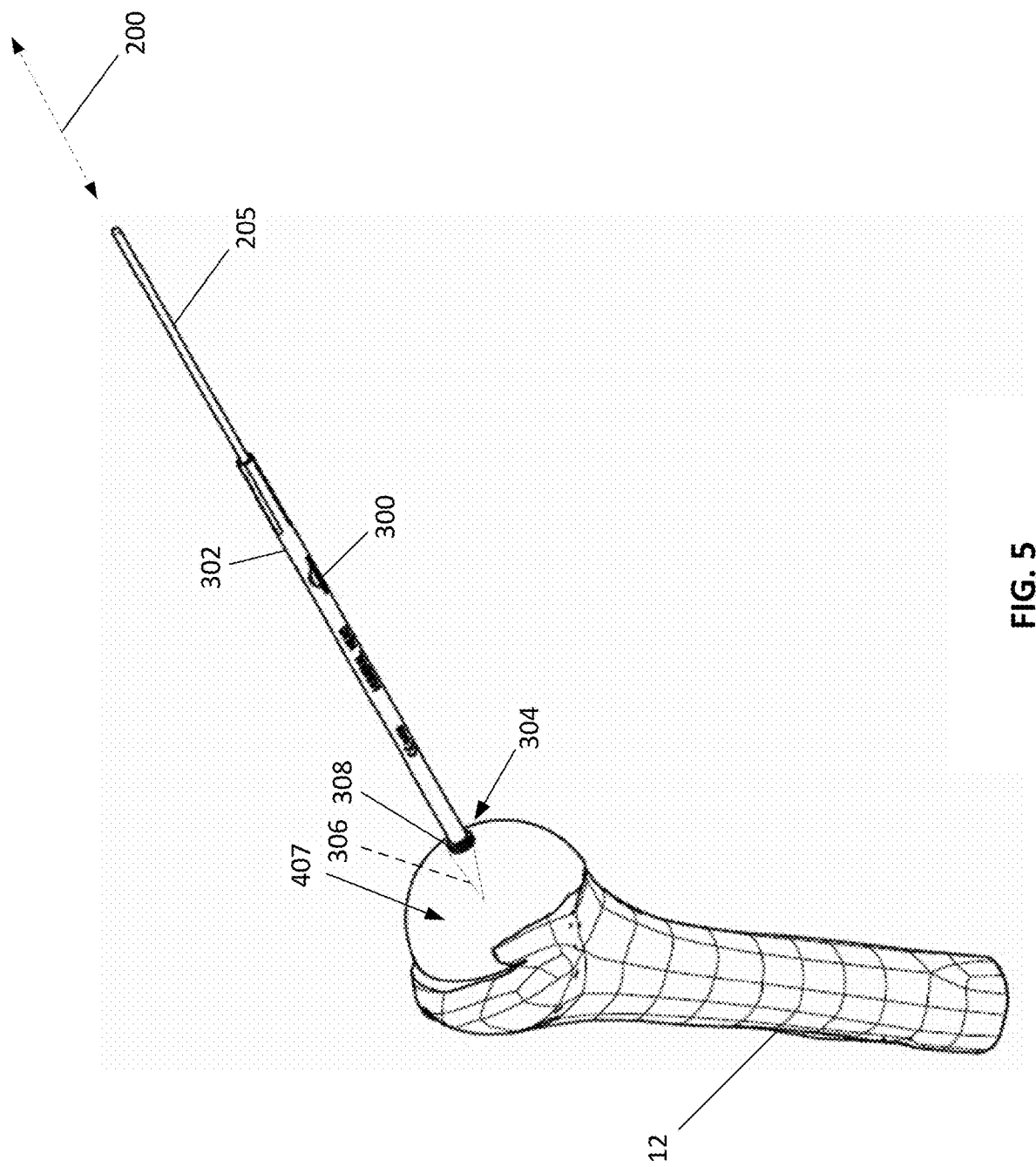
FIG. 5 generally illustrates one example of an arcuate surface formed on the first bone consistent with the present disclosure.

Turning now FIG. 4, optionally a first reamer 400 may be rotated and advanced along the working axis 200 to form at least a portion of the humeral implant site 10. In the illustrated example, the first reamer 400 may include a cannulated shaft 402 configured to be rotated and advanced over the pin 205 and/or the cannulated threaded instrument 300. A distal end region 404 of the first reamer 400 may include one or more cutting surfaces 406 configured to remove at least a portion of the native articular surface 202. For example, the first reamer 400 may include one or more cutting arms 408 extending radially outward from the shaft 402. The cutting arms 408 may include one or more cutting surfaces 406 having an arcuate shape. The arcuate shape of the cutting surfaces 406 may be configured to remove at least some of the native articular surface 202 and form an arcuate surface 407 (as shown in FIGS. 4-5) revolved around the working axis 200. For example, the cutting surfaces 406 may be configured to form a generally semi-spherical shape/surface (e.g., convex surface) on the bone 12. Alternatively (or in addition), the cutting surfaces 406 may be formed by two or more tangential curves and/or having one or more inflection points, for example, configured to form a semi-ellipsoidal shape. The first reamer 400 may be advanced along the working axis 200 until a portion of the first reamer 400 (e.g., a central portion) contacts/abuts against a portion of the shoulder 308 of the cannulated threaded instrument 300. Alternatively (or in addition), the depth of the first reamer 400 along the working axis 200 may be set/determined using indicia/markings on the pin 205 and/or the cannulated threaded instrument 300.

Figure 6:
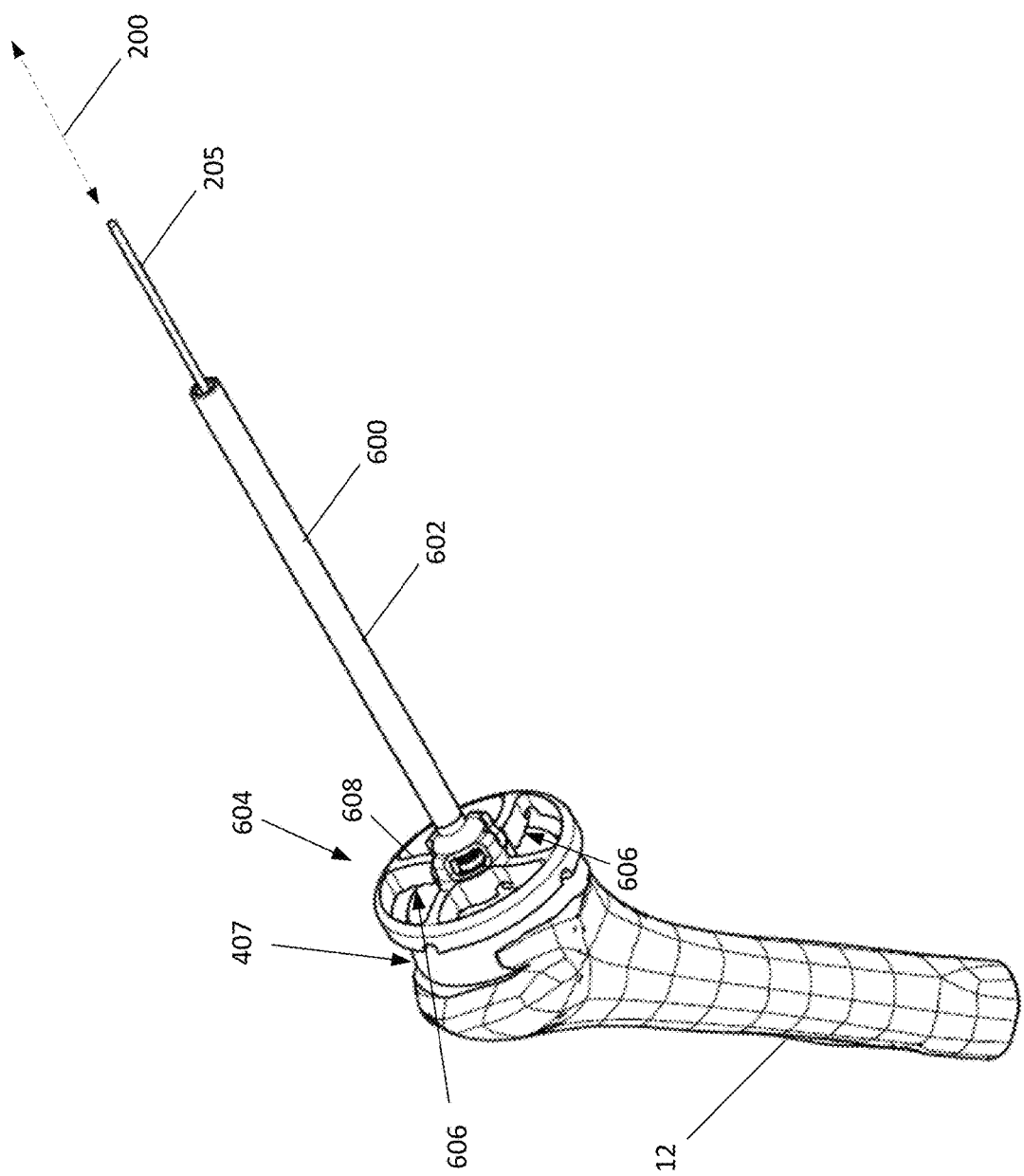
FIG. 6 generally illustrates one example of second reamer along the working axis consistent with the present disclosure.
Figure 7:
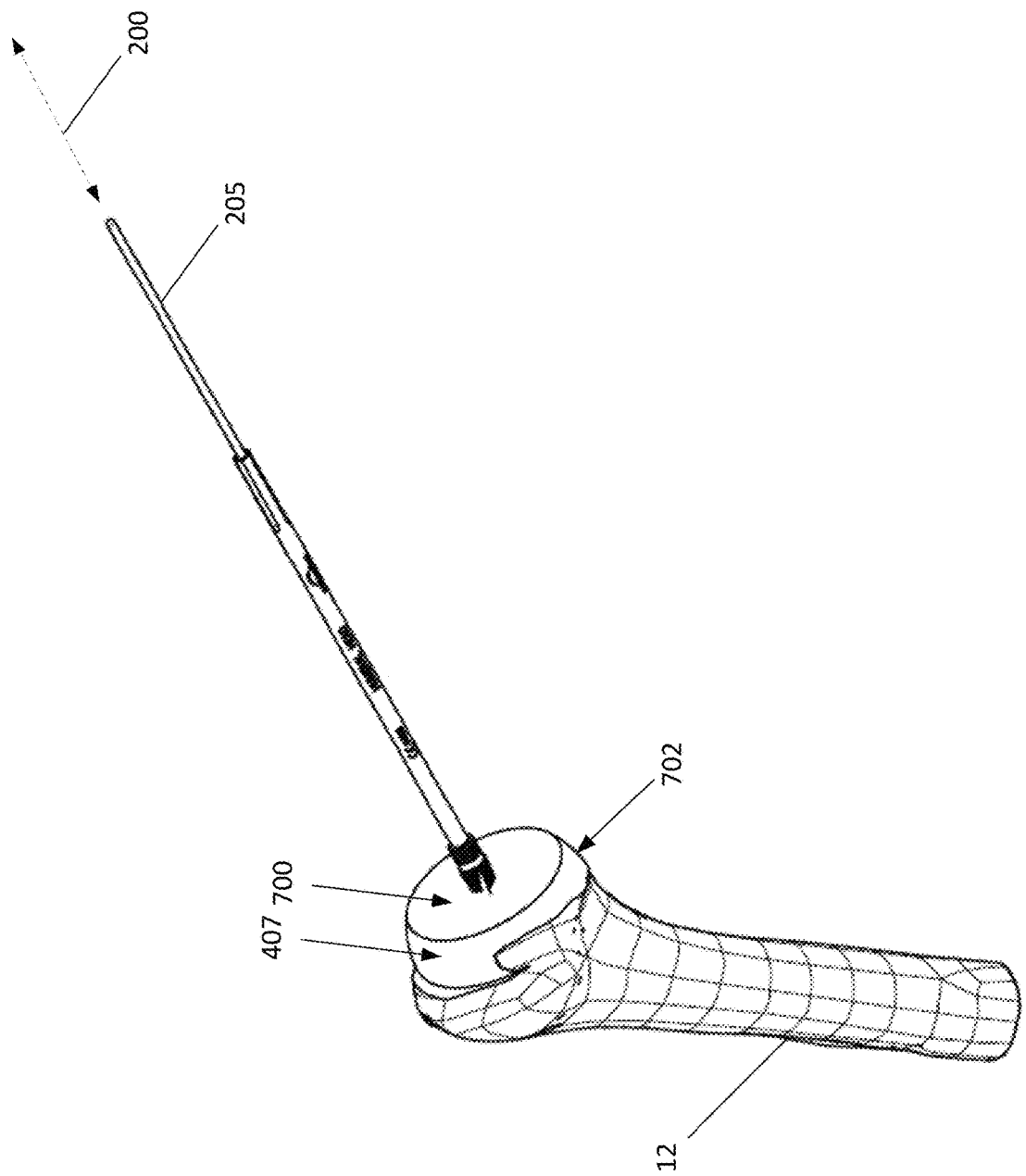
FIG. 7 generally illustrates one example of an intermediate central surface formed on the first bone consistent with the present disclosure.

Referring to FIG. 6, optionally a second (or additional) cut may be made using a second reamer 600. The second cut may be made to a portion of the arcuate surface 407 formed using the first reamer 400 (e.g., the semi-spherical surface). For example, the first reamer 400 may be removed from working axis 200, and the second reamer 600 may be rotated and advanced along the working axis 200 (e.g., to form at least a portion of the humeral implant site 10). In the illustrated example, the second reamer 600 may include a cannulated shaft 602 configured to be rotated and advanced over the pin 205 and/or the cannulated threaded instrument 300 and revolved around the working axis 200. A distal end region 604 of the second reamer 600 may include one or more cutting surfaces 606 configured to remove at least a portion of the arcuate surface 407. For example, the second reamer 600 may include one or more cutting arms 608 extending radially outward from the shaft 602. The cutting arms 608 may include one or more cutting surfaces 606, for example, having a generally flat, planar, and/or arcuate shape. The second reamer 600 may used to remove a central region 609 of the arcuate surface 407, for example, to form an intermediate central surface 700 (FIG. 7) revolved around the working axis 200.

The cutting surfaces 606 may be configured to remove at least some of the central region 609 of the intermediate central surface 700 revolved around the working axis 200, while leaving behind an arcuate (e.g., semi-spherical) outer ring 702 of the arcuate surface 407 centered around the working axis 200. As described herein, the arcuate outer ring 702 may inversely correspond to a portion of an inner surface of the tray 18 of the humeral implant system 14. As such, the at least a portion of the profile of the cutting surface 406 of the first reamer 400, when revolved around the working axis 200, may correspond to the portion of the inner surface of the tray 18 of the humeral implant system 14.

In at least one example, the cutting surfaces 606 of the second reamer 600 may be configured to form a generally planar shape/surface. Alternatively (or in addition), the cutting surfaces 606 may be formed by one curves, two or more tangential curves, and/or curves having one or more inflection points. The second reamer 600 may be advanced along the working axis 200 until a portion of the second reamer 600 (e.g., a central portion) contacts/abuts against a portion of the shoulder 308 of the cannulated threaded instrument 300. Alternatively (or in addition), the depth of the second reamer 600 along the working axis 200 may be set/determined using indicia/markings on the pin 205 and/or the cannulated threaded instrument 300. While the intermediate central surface 700 is shown having a generally planar surface and the central region 609 formed by the first reamer 400 is shown having a semi-spherical surface, it should be appreciated that the present disclosure is not limited to either of these configurations unless specifically claimed as such since these surfaces will ultimately be removed.

Figure 8:
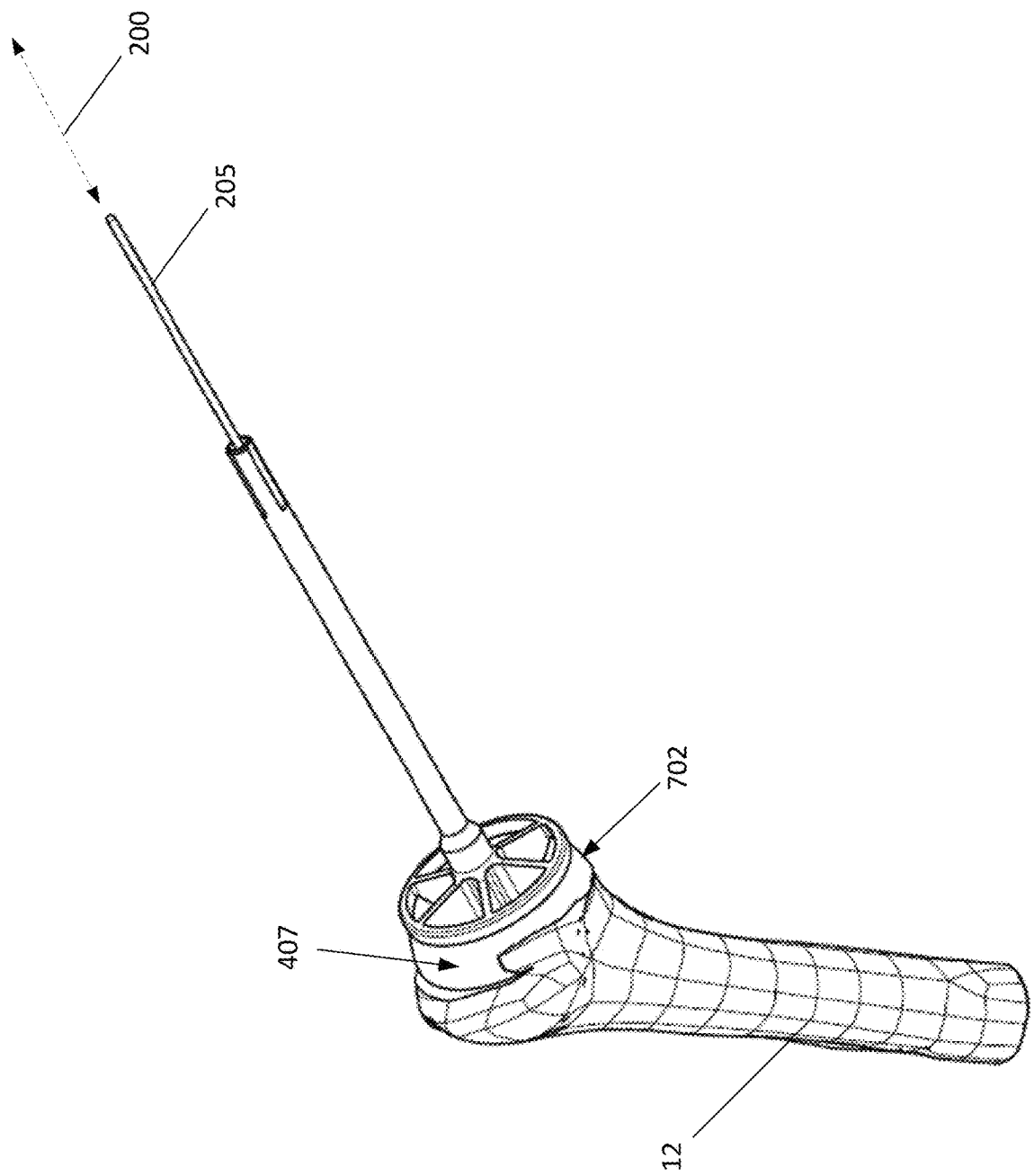
FIG. 8 generally illustrates one example of third reamer along the working axis consistent with the present disclosure.

Turning to FIG. 8, optionally a third (or additional) cut may be made using a third reamer 800. The third cut may be made to at least a portion of the intermediate central surface 700 formed using the second reamer 600. For example, the second reamer 600 may be removed from working axis 200, and the third reamer 800 may be rotated and advanced along the working axis 200 (e.g., to form at least a portion of the humeral implant site 10). In the illustrated example, the third reamer 800 may include a cannulated shaft 802 configured to be rotated and advanced over the pin 205 and/or the cannulated threaded instrument 300. A distal end region 804 of the third reamer 800 may include one or more cutting surfaces 806 configured to remove at least a portion of the intermediate central surface 700. For example, the third reamer 800 may include one or more cutting arms 808 extending radially outward from the shaft 802. The cutting arms 808 may include one or more cutting surfaces 806 configured to form a convex socket/surface 900 (FIG. 9) revolved around the working axis 200.

Figure 9:
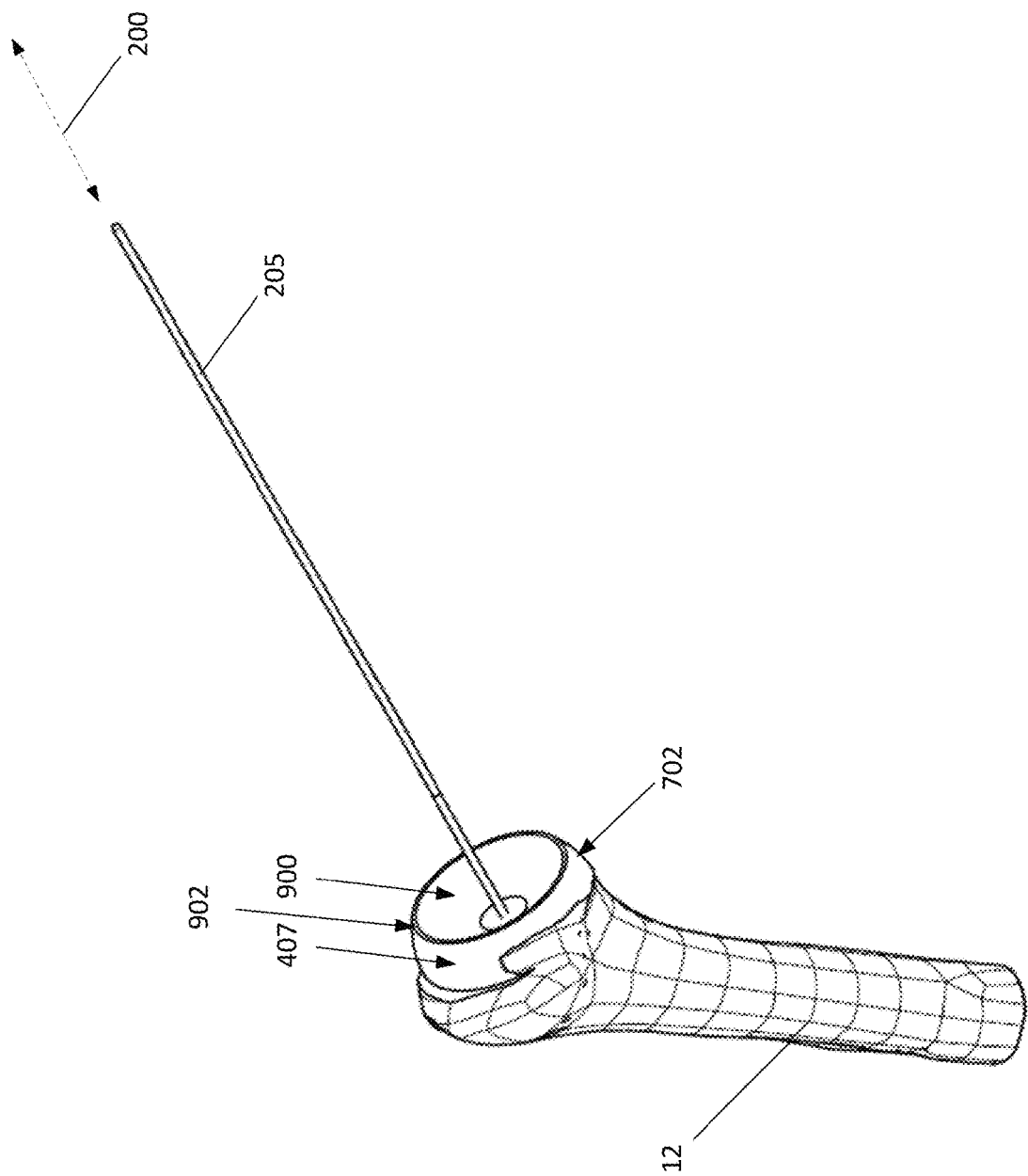
FIG. 9 generally illustrates one example of a socket formed on the first bone consistent with the present disclosure.

A peripheral rim 902 may be formed between the convex socket/surface 900. In at least one example, the peripheral rim 902 may be formed by a remaining portion of the intermediate central surface 700. As such, the third reamer 800 may remove only a portion of the intermediate central surface 700. Alternatively, peripheral rim 902 may be formed by the intersection of the arcuate outer ring 702 with the convex socket/surface 900. As such, the third reamer 800 may remove all of the intermediate central surface 700. As described herein, the convex surface/socket 900 and/or the peripheral rim 902 may inversely correspond to a portion of an inner surface of the tray 18. As such, the at least a portion of the profile of the cutting surface 806 of the third reamer 800, when revolved around the working axis 200, may correspond to the portion of the inner surface of the tray 18. Once the convex surface/socket 900 has been formed, the cannulated threaded instrument 300 may be removed as shown in FIG. 9.

Figure 10:
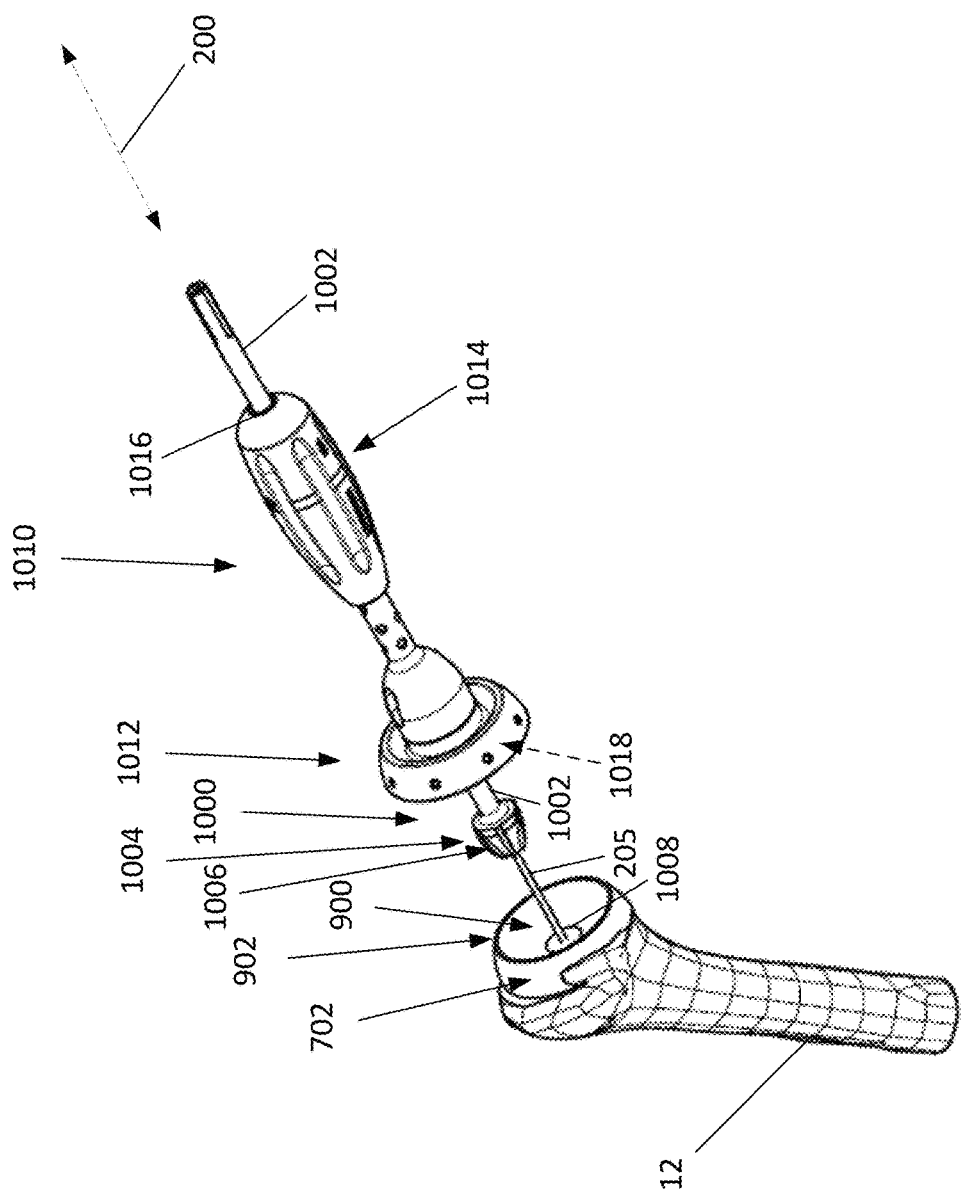
FIG. 10 generally illustrates one example of forming a pilot hole along the working axis consistent with the present disclosure.

With reference to FIG. 10, optionally a fourth (or additional) cut may be made using a fourth reamer 1000. The fourth cut may be made to at least a portion of the convex surface/socket 900 formed using the third reamer 800. For example, the third reamer 800 may be removed from working axis 200, and the fourth reamer 1000 may be rotated and advanced along the working axis 200 to form a pilot hole for the anchor 16 of the humeral implant system 14. In the illustrated example, the fourth reamer 1000 may include a cannulated shaft 1002 configured to be rotated and advanced over the pin 205. A distal end region 1004 of the fourth reamer 1000 may include one or more cutting surfaces 1006 configured to remove at least a portion of the socket 900 to form a pilot hole 1008.

Figure 11:
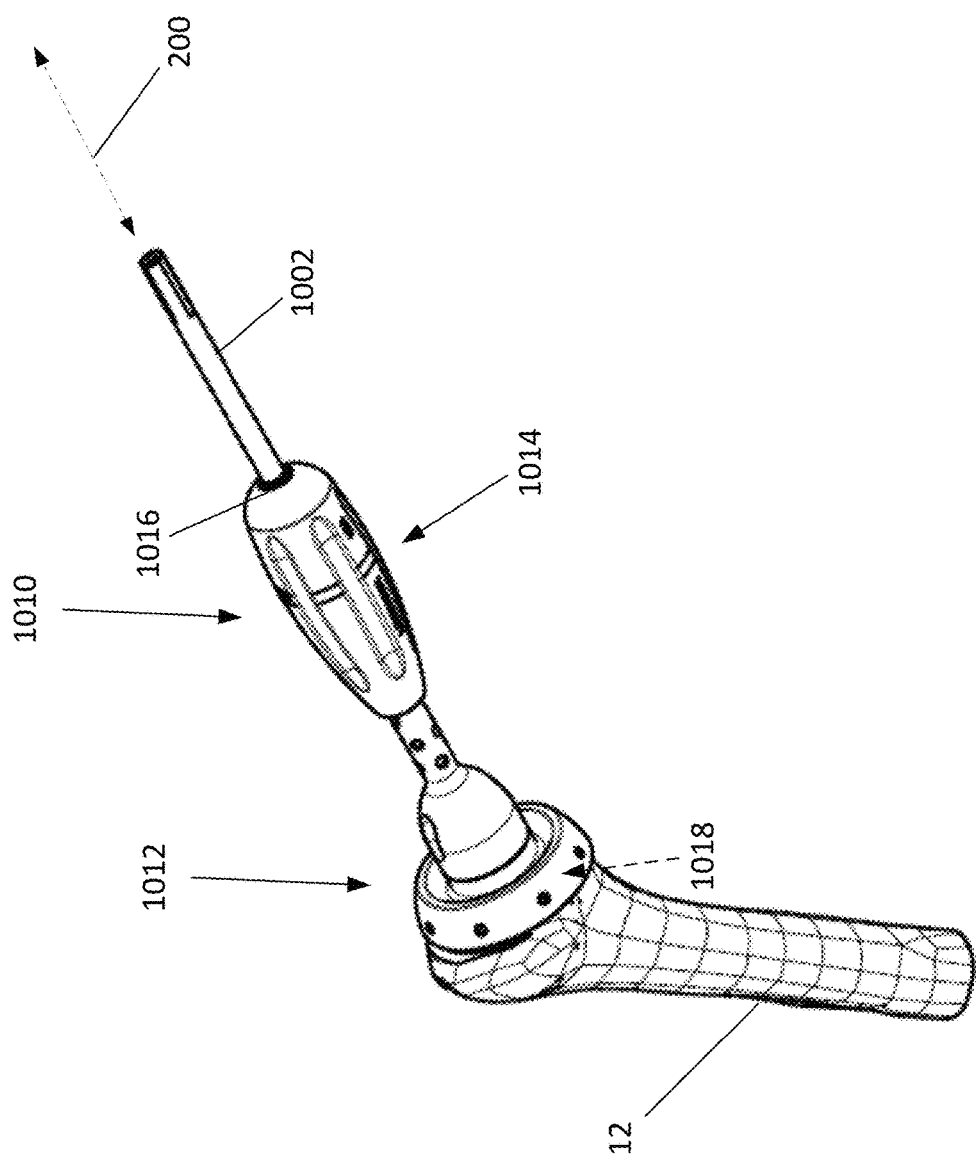
FIG. 11 generally illustrates one example of an implant trial consistent with the present disclosure.

Optionally, a trial implant 1010 may be used to set the depth of the fourth reamer 1000 (e.g., using indicate on the pin 205 and/or the trial implant 1010 such as, but not limited to, laser markings, windows, shoulders, or the like). Alternatively (or in addition), the trial implant 1010 may be used to verify the surface contour of the arcuate outer ring 702, the socket 900, and/or the peripheral rim 902. For example, the trial implant 1010 may include a trial 1012 coupled to a handle 1014. The trial 1012 and the handle 1014 may be cannulated and configured to be advanced along the working axis 200. In the illustrated example, the trial 1012 and the handle 1014 may include a passageway 1016 configured to receive the cannulated shaft 1002 of the fourth reamer 1000. The trial 1012 may have an inner surface 1018 which corresponds to the inner surface of the tray 18 of the humeral implant system 14. The trial 1012 may therefore be advanced along the working axis 200 and used to verify that the surface contour of the arcuate outer ring 702, the socket 900, and/or the peripheral rim 902 matches the profile of the tray 18. The trial 1012 (e.g., the inner surface 1018) may contact three portions of the arcuate outer ring 702, the socket 900, and/or the peripheral rim 902 and/or may contact the entire surface of the arcuate outer ring 702, the socket 900, and/or the peripheral rim 902 (e.g., as generally illustrated in FIG. 11).

Figure 12:
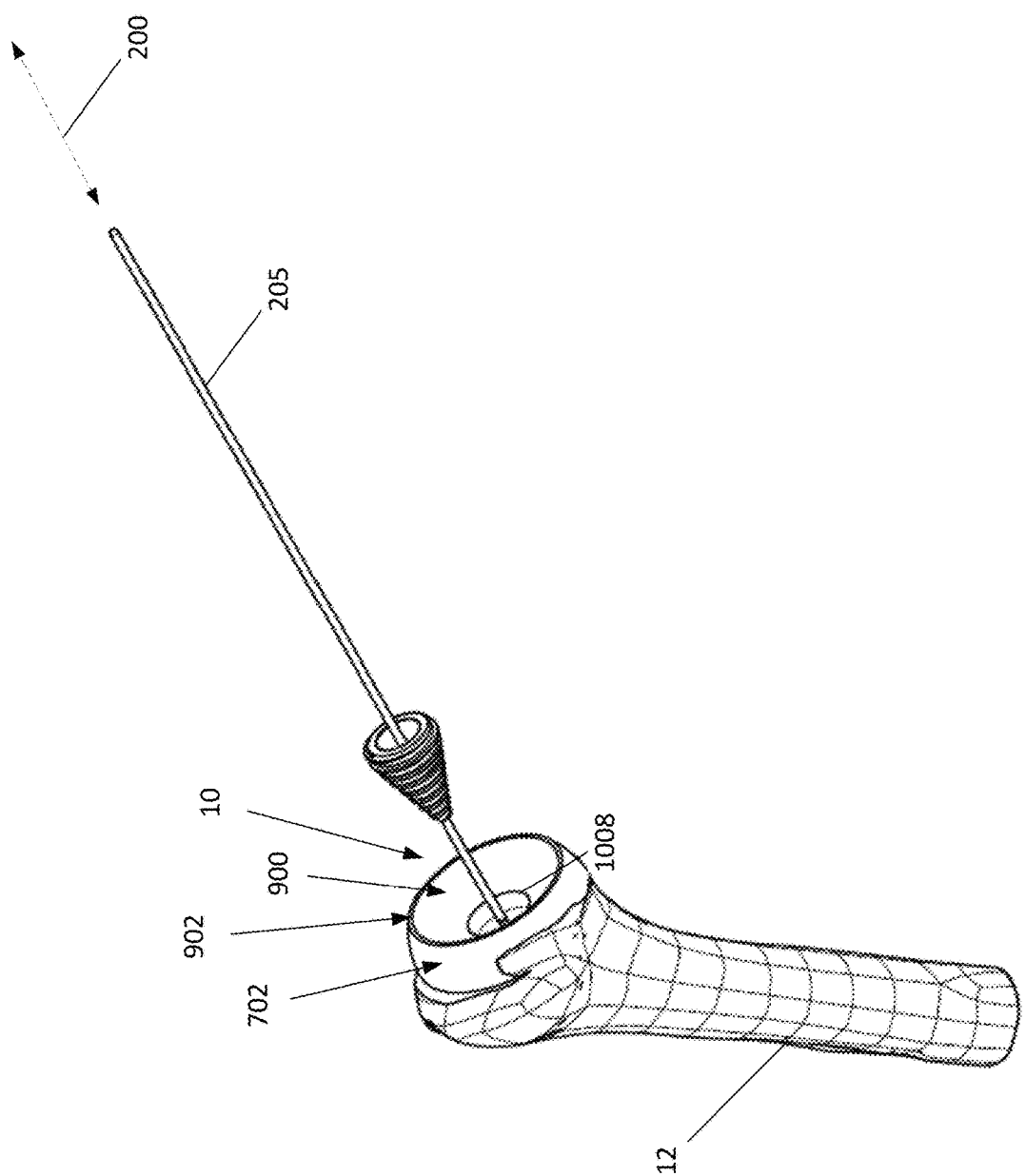
FIG. 12 generally illustrates one example of an anchor along the working axis consistent with the present disclosure.

The reamers 400, 600, 800, 1000 may therefore be used to form the humeral implant site 10 (e.g., as generally illustrated in FIG. 12). The humeral implant site 10 may be formed in the humerus 12 in such a manner to aid in the positioning of the humeral implant system 14 and to reduce and/or prevent movement of the humeral implant system 14 relative to the humerus 12. At least a portion of the humeral implant site 10 (e.g., the arcuate outer ring 702, the socket 900, and/or the peripheral rim 902) may therefore be formed with a shape/contour/profile that inversely corresponds to the shape/contour/profile of tray 18 of the humeral implant system 14. While the system and method for forming the humeral implant site 10 has been described using a plurality of reamers 400, 600, 800, 1000, it should be appreciated that two or more of the reamers 400, 600, 800, 1000 may be combined into a single reamer. A benefit of the use of multiple reamers 400, 600, 800, 1000 as described herein is that it minimizes the likelihood of damaging the bone 12, while also ensuring proper alignment and fit of the resulting humeral implant site 10. Moreover, while the system and method for forming the humeral implant site 10 has been described using a pin 205, it should be appreciated that the pin 205 may be eliminated. For example, the system and method for forming the humeral implant site 10 may be performed using a computer numerical control (CNC) machine such as, but not limited to, a robot controlled multiple axis CNC machine or the like.

Before and/or after the fit of the surface of the arcuate outer ring 702, the socket 900, and/or the peripheral rim 902 have been verified, the anchor 16 of the humeral implant system 14 may be advanced and secured into the bone 12 along the working axis 200, e.g., into the pilot hole 1008 as shown in FIG. 12. Turning now to FIGS. 13A-F, various views of one example of an anchor 16 consistent with the present disclosure are generally illustrated. The anchor 16 may include a body 1302, for example, having a tapered profile. The outside of the body 1302 may include one or more retaining elements (such as, but not limited to, threads, protrusions, ribs, barbs, recesses, or the like 1304) configured to engage the bone 12 and secure the anchor 16 to the bone 12. The anchor 16 may optionally be used with bone cement or the like. The outer surface of the anchor 16 may be configured to facilitate bone regrow. The body 1302 may include a cannulated passageway 1306, for example, configured to be advanced over the pin 205.

A proximal end 1308 of the anchor 16 may include a fixation element 1310 configured to be coupled to a corresponding fixation element of the tray 18 to secure the anchor 16 to the tray 18. For example, the fixation element 1310 includes a tapered interference fit (e.g., a Morse taper or the like). In the illustrated example, the fixation element 1310 is a female tapered recess configured to mate with a corresponding tapered male protrusion formed on the tray 18; however, it should be appreciated that this arrangement may be reversed. Alternatively (or in addition), the fixation element 1310 may include any other mechanism and/or fastener for either permanently or removably coupling the anchor 16 to the tray 18 such as, but not limited to, snap fit connections, threaded connections, adhesives, or the like.

The proximal end 1308 of the anchor 16 may optionally include a driving feature 1312. The driving feature 1312 may be configured to mate with a driver (such as a drill or the like) to secure the anchor 16 into the bone 12. For example, the driving feature 1312 may be configured to allow a drill to rotate the anchor 16 into the bone. In the non-limiting example, the driving feature 1312 is a hex recess.

Figure 14:
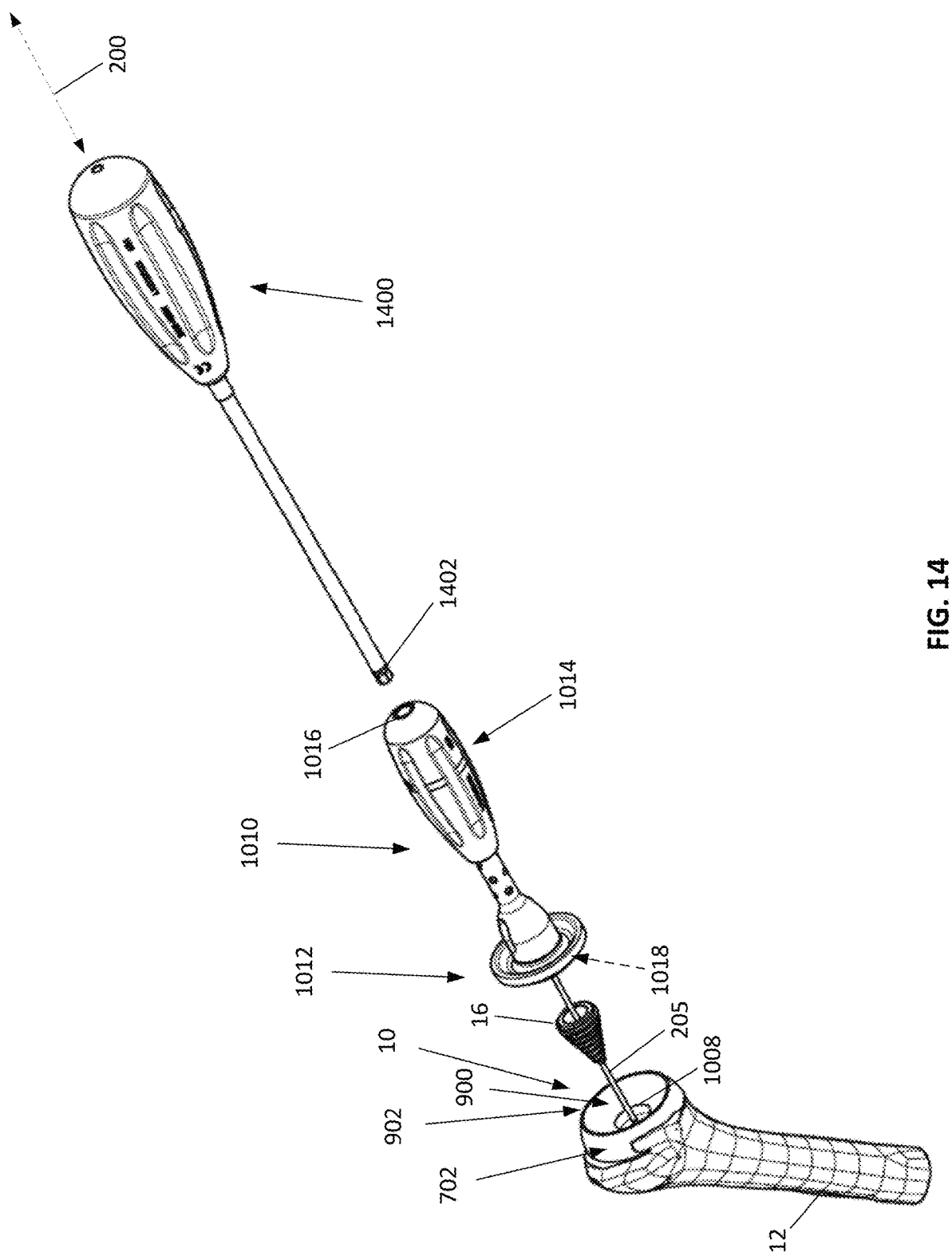
FIG. 14 generally illustrates one example of the anchor being advanced along the working axis consistent with the present disclosure.
Figure 15:
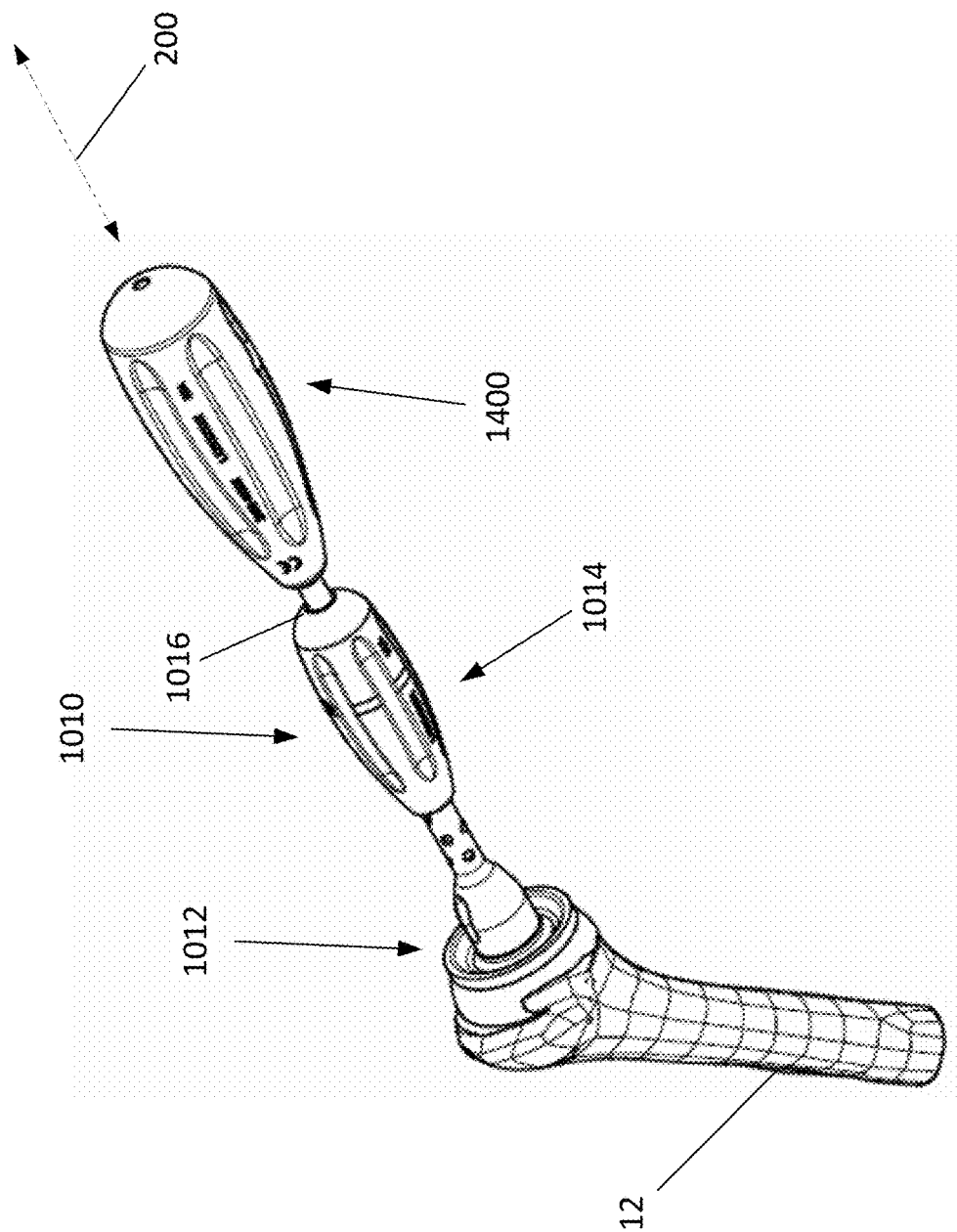
FIG. 15 generally illustrates one example of the anchor secured in the first bone consistent with the present disclosure.

Referring to FIG. 14, the anchor 16 may be advanced over the pin 205 using a driver 1400 (e.g., a hand drill or the like) having a corresponding driving feature 1402 (e.g., a hex head) configured to engage with the driving feature 1312 of the anchor 16. The driver 1400 may optionally be configured to be received through the trial implant 1010 along the working axis 200. For example, the anchor 16, trial implant 1010, and then the driver 1400 may be advanced over the pin 205. The driving feature 1402 of the driver 1400 may then be coupled to the driving feature 1312 of the anchor 16 to secure (e.g., rotate) the anchor 16 into the bone 12 within the pilot hole 1008. The depth of the anchor 16 within the bone 12 may be set using indicia on the driver 1400, pin 205, and/or trial implant 1010 (such as, but not limited to, laser markings, windows, shoulders, or the like) as generally illustrated in FIG. 15. For example, the trial implant 1010 may be advanced over the pin 205 such that the inner surface 1018 of the trial 1012 engages against the humeral implant site 10 (e.g., the arcuate outer ring 702, the socket 900, and/or the peripheral rim 902).

Figure 16:
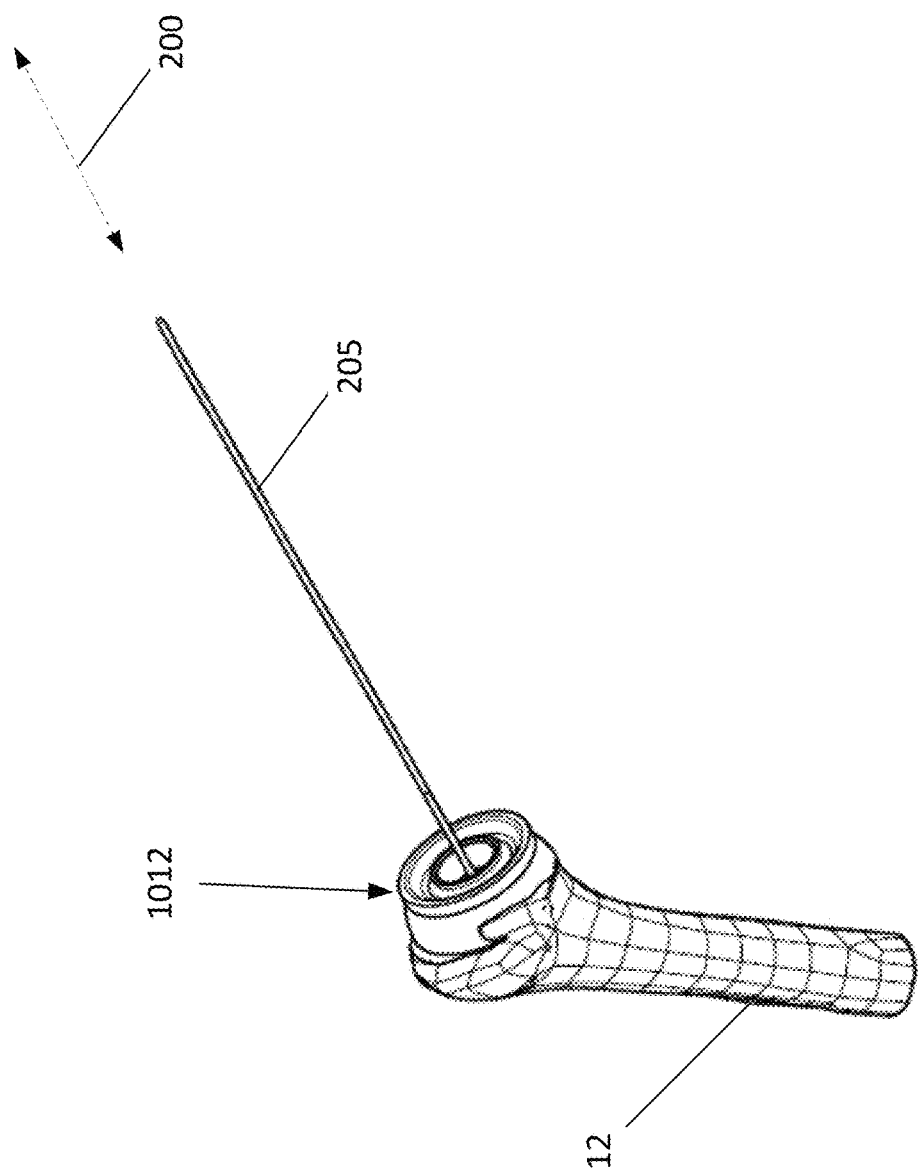
FIGS. 16-17 generally illustrate one example of a trial along the working axis consistent with the present disclosure.
Figure 17:
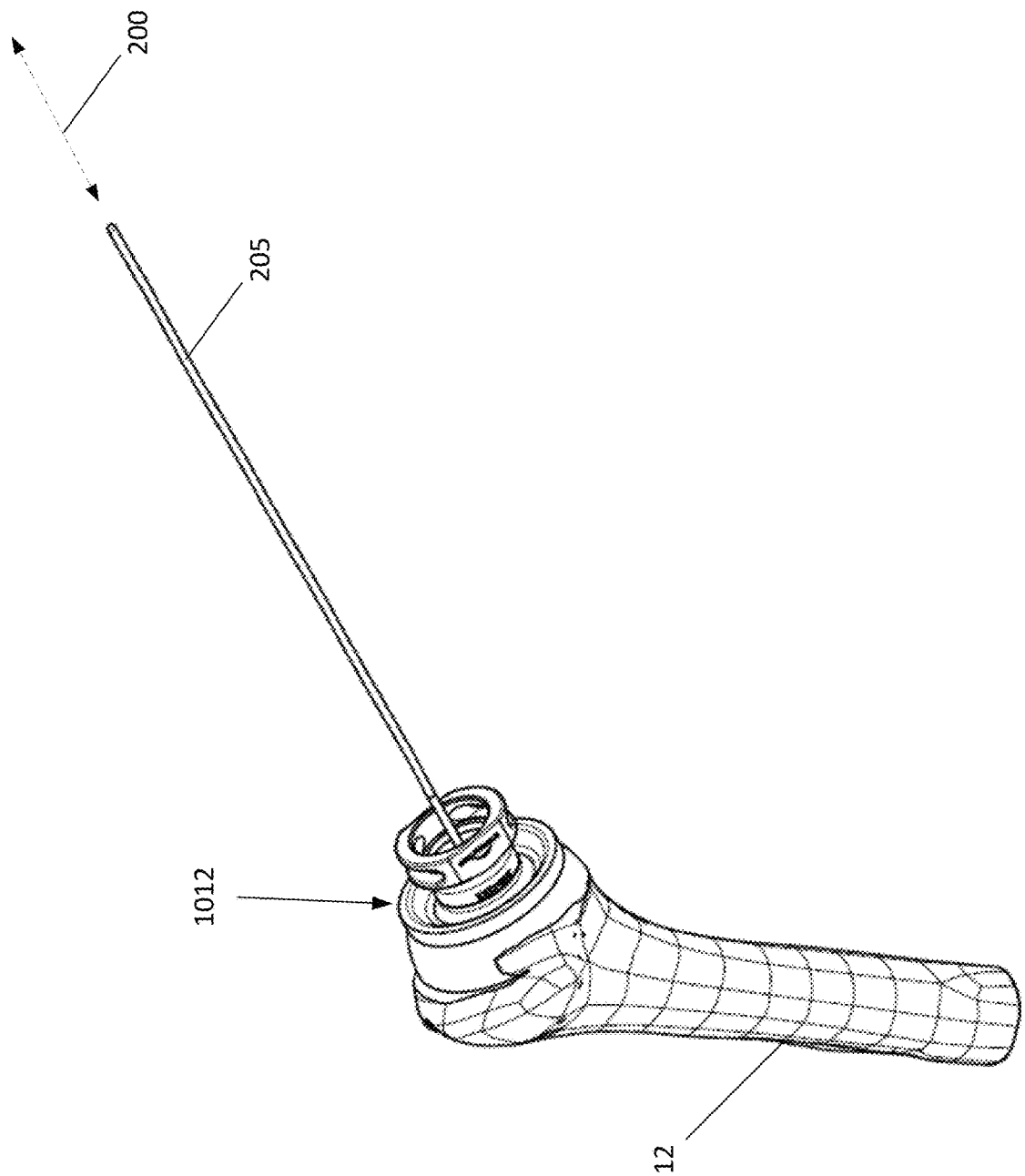
Figure 19E:
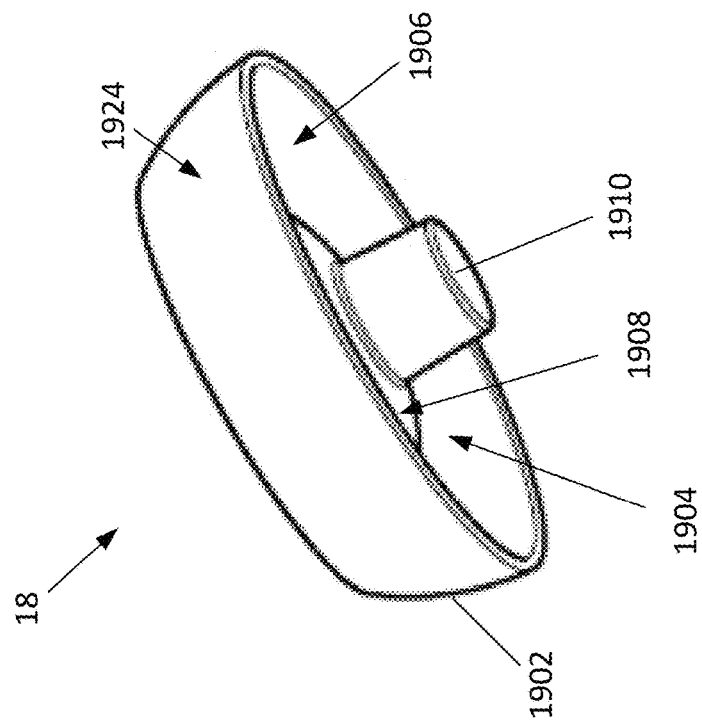
Figure 19D:
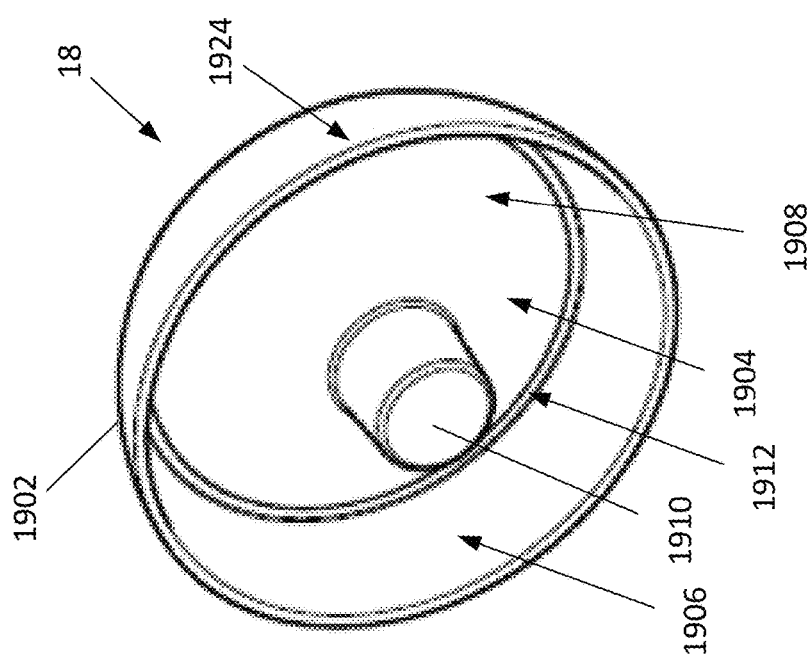
Figure 20C:
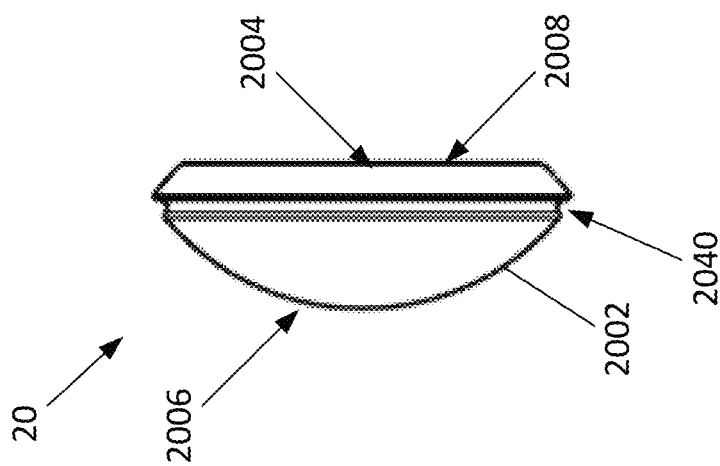
Figure 20B:
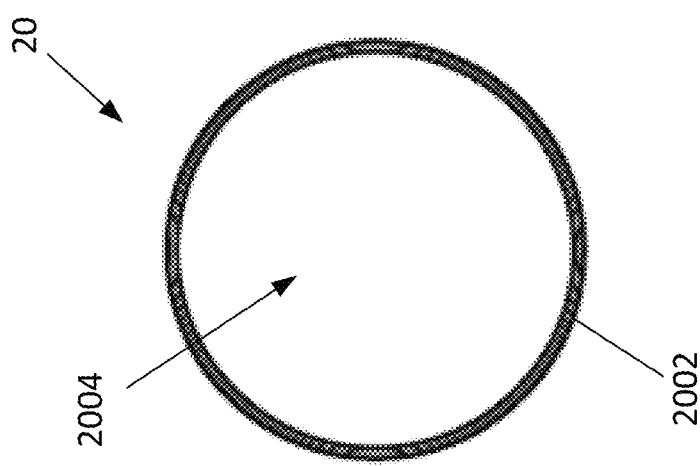
Figure 20A:
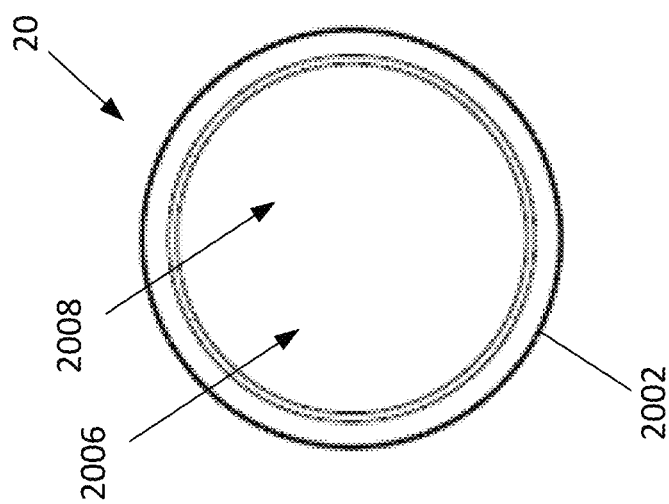

The trial 1012 may be removably coupled to the handle 1016. In the illustrated example, the handle 1016 and the driver may be once the anchor 16 is set within the bone 12, for example, as generally illustrated in FIG. 16. The trial 1012 may optionally include a fixation element corresponding to the fixation element 1310 of the anchor 16. As such, the trial 1012 may be urged into engagement with the anchor 16 to ensure proper alignment of the anchor 16 within the bone 12, for example, as generally illustrated in FIG. 17.

Once proper fit of the trial 1012 with the humeral implant site 10 has been confirmed, the pin 205 and the trial 1012 may be removed. Next, the tray 18 may be coupled to the anchor 16 that is secured in the bone 12, for example, as generally illustrated in FIG. 18, and the liner 20 may thereafter be coupled to the tray 18.

Turning now to FIGS. 19A-E, various views of one example of a tray 18 consistent with the present disclosure are generally illustrated. The tray 18 may include a body 1902 defining a bone facing recess 1904 and a liner recess 1906. The bone facing recess 1904 may include a ring surface 1906 and a convex surface 1908. In particular, the ring surface 1906 may have a profile substantially inversely corresponding to the profile of the arcuate outer ring 702 of the humeral excision site 10. Similarly, the convex surface 1908 may have a profile substantially inversely corresponding to the profile of the convex socket/surface 900 of the humeral excision site 10. The ring surface 1906 and/or the convex surface 1908 may therefore correspond to the cutting surface of the reamers revolved around the working axis 200. The bone facing recess 1904 may also optionally include a peripheral region 1912 corresponding to the peripheral rim 902 of the humeral excision site 10. The peripheral region 1912 may be disposed between the ring surface 1906 and the convex surface 1908.

The tray 18 may include a fixation element 1910 configured to be coupled to the corresponding fixation element 1310 of the anchor 16 to secure the tray 18 to the anchor 16. As discussed herein, the fixation elements 1310, 1910 includes a tapered interference fit (e.g., a Morse taper or the like). In the illustrated example, the fixation element 1910 is a male tapered protrusion extending outward from the bone facing recess 1904 configured to mate with a corresponding tapered female recess formed on the anchor 16; however, it should be appreciated that this arrangement may be reversed. Alternatively (or in addition), the fixation elements 1310, 1910 may include any other mechanism and/or fastener for either permanently or removably coupling the anchor 16 to the tray 18 such as, but not limited to, snap fit connections, threaded connections, adhesives, or the like. The fixation elements 1310, 1910 may be aligned along the working axis 200. Alternatively, the fixation elements 1310, 1910 may not be coaxial with the working axis 200.

The ring surface 1906, the convex surface 1908, and/or the peripheral region 1912 may optionally include one or more retaining elements (such as, but not limited to, threads, protrusions, ribs, barbs, recesses, or the like) configured to engage the bone 12 of the humeral excision site 10 and secure the tray 18 to the bone 12. The tray 18 may optionally be used with bone cement or the like. The bone facing recess 1904 of the tray 18 may be configured to facilitate bone regrow.

The liner recess 1906 of the tray 18 may be configured to be coupled to the implant 20. The liner recess 1906 may have a generally concave shape configured to receive at least a portion of the implant 20. For example, the liner recess 1906 may have a generally concave shape that generally inversely corresponds to a tray interface surface of the implant 20. According to one example, the tray 18 may include one or more fixation elements 1920 configured to be coupled to a corresponding fixation element of the implant/liner 20 to secure the implant/liner 20 to the tray 18. In the illustrated example, the fixation element 1920 may form a snap fit connection with the implant/liner 20. For example, the fixation element 1920 may include a tab or latch configured to deform when the implant 20 is urged into the liner recess 1906, and then resiliently snap back into a recess and/or groove on the implant 20. Of course, the fixation element 1920 may alternatively or additionally include any other mechanism and/or fastener for either permanently or removably coupling the implant 20 to the tray 18 such as, but not limited to, tapered interference connections (e.g., a Morse taper or the like), threaded connections, adhesives, or the like.

The tray 18 may have a thickness 1922 configured to position the implant 20 at the desired position relative to the bone 12. The outer surface 1924 of the body 1902 of the tray 18 may have a generally frusto-conical and/or frusto-spherical shape. The generally frusto-conical and/or frusto-spherical shape may be configured to allow the humerus 12 to move relative to the glenoid while minimizing the potential for the humerus 12 to contact the glenoid.

Turning now to FIGS. 20A-H, various views of one example of an implant/liner 20 consistent with the present disclosure are generally illustrated. The implant 20 may include a body 2002 defining a load bearing surface 2004 and a tray interface surface 2006. The load bearing surface 2004 may include a recessed and/or concaved surface 2008. The concaved surface 2008 may therefore be used in a reverse shoulder application in which the native arrangement of the ball and socket of the shoulder is reversed. For example, the concaved surface 2008 may include a semi-spherical shape and/or a semi-ellipsoidal shape. Alternatively, the load bearing surface may include convex surface. The convex surface (e.g., a generally spherical and/or semi-ellipsoid) may generally correspond native articular surface of the patient's humerus 12.

The tray interface surface 2006 is configured to be at least partially received in the liner recess 1906 of the tray 18 such that the implant 20 is coupled to the tray 18. The tray interface surface 2006 may have a generally convex shape that generally inversely corresponds to the liner recess 1906 of the tray 18. As discussed herein, the implant 20 may include one or more fixation elements 1940 configured to be coupled to a corresponding fixation element 1920 of the tray 18 to secure the implant 20 to the tray 18. In the illustrated example, the fixation elements 1920, 1940 may form a snap fit connection. For example, the fixation element 1940 may include a recess and/or groove configured to deform a tab or latch 1920 of the tray 18 when the implant 20 is urged into the liner recess 1906. Of course, the arrangement of the latch and groove may be reversed and the fixation elements 1920, 1940 may alternatively or additionally include any other mechanism and/or fastener for either permanently or removably coupling the implant 20 to the tray 18 such as, but not limited to, tapered interference connections (e.g., a Morse taper or the like), threaded connections, adhesives, or the like.

Figure 21:
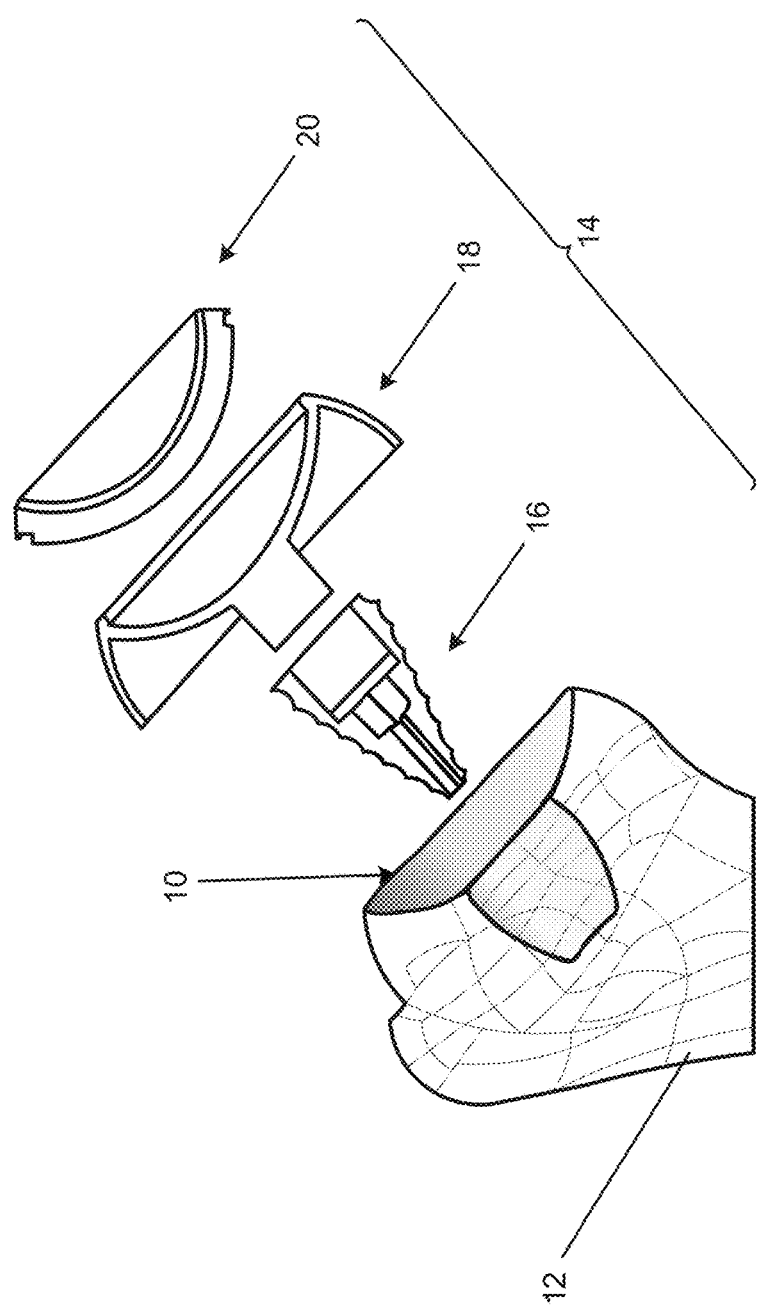
FIG. 21 generally illustrates an exploded view of one example of the first implant system and the first excision site consistent with the present disclosure.
Figure 22:
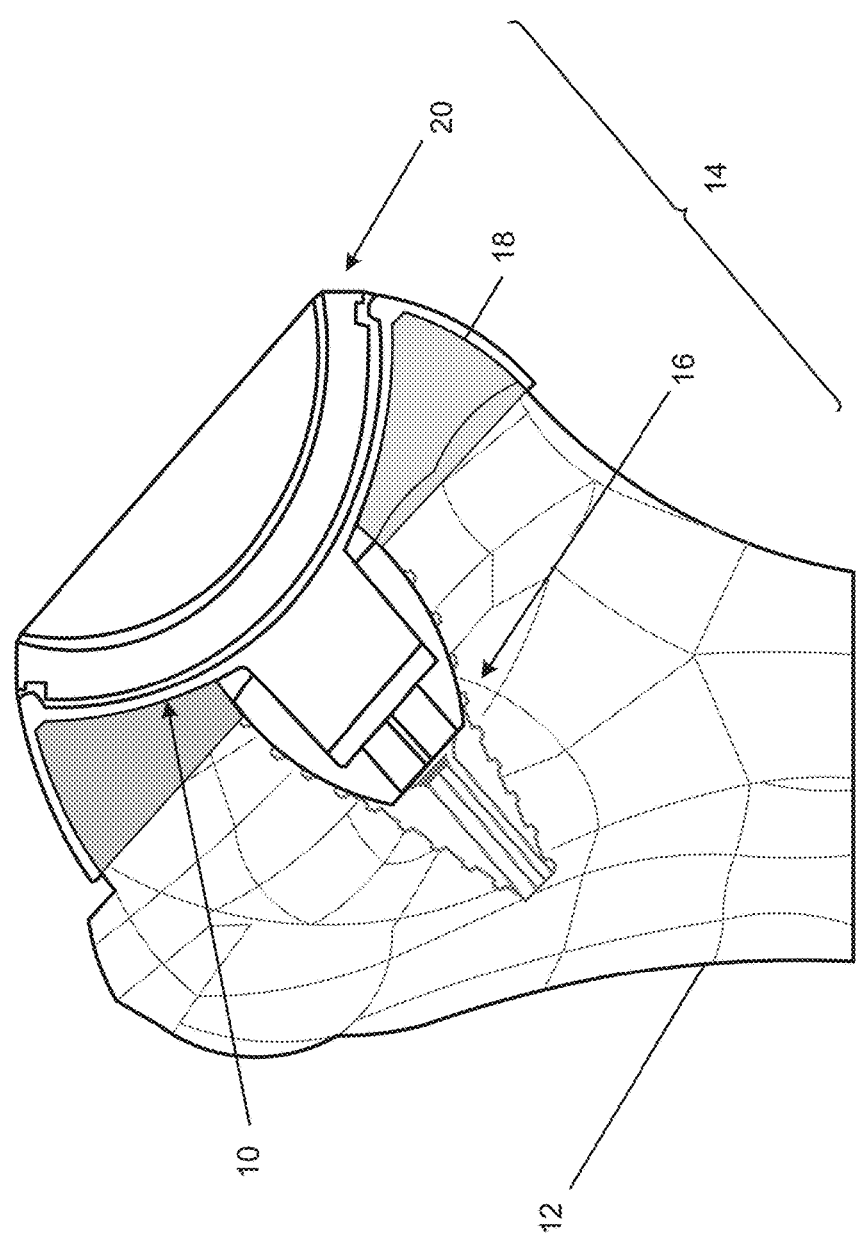
FIG. 22 generally illustrates an assemble view of one example of the first implant system and the first excision site consistent with the present disclosure.

With reference to FIG. 21, an exploded cross-sectional view of the humeral excision site 10 and the humeral implant system 14 is generally illustrated, while FIG. 22 generally illustrates an assembled cross-sectional view the humeral implant system 14 in the humeral excision site 10. The anchor 16, the tray 18, and/or the implant 20 may be made from metal such as, but not limited to, cobalt chromium, stainless steel, and/or titanium (and alloys thereof). The tray 18 and/or the implant 20 may optionally be made from biocompatible plastic such as, but not limited to, ultra-high-molecular-weight polyethylene (UHMWPE) or the like.

Figure 23:
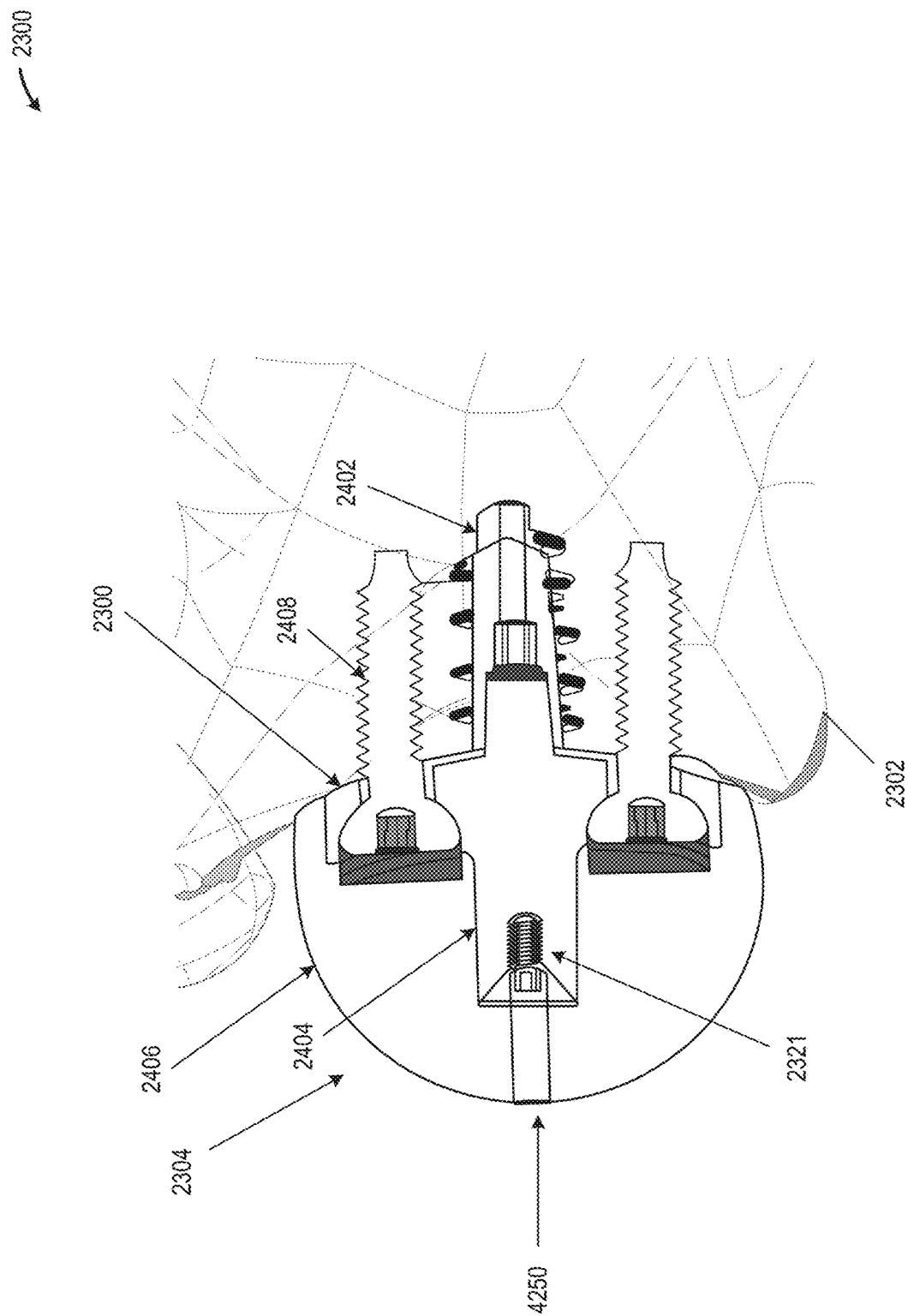
FIG. 23 generally illustrates an assembled view of one example of a second implant system and a second excision site consistent with the present disclosure.

With reference to FIG. 23, a non-limiting example of a second implant site 2300 formed in a second bone 2302 and a second implant system 2404 is generally illustrated. While aspects/embodiments of the second implant site 2300 and the second implant system 2404 may be described in the context of a glenoid excision site formed in the glenoid bone and a glenoid implant system, it should be appreciated that the second implant site 2300 may be formed in other bones (e.g., other than the glenoid 2302) and the second implant system 2404 is not limited to a glenoid implant system. As such, the systems and method described herein may be used to form a second implant site 2300 on any bone 2302 and the second implant system 2404 may be used to repair/replace the articular surface of any bone 2302.

Figure 24:
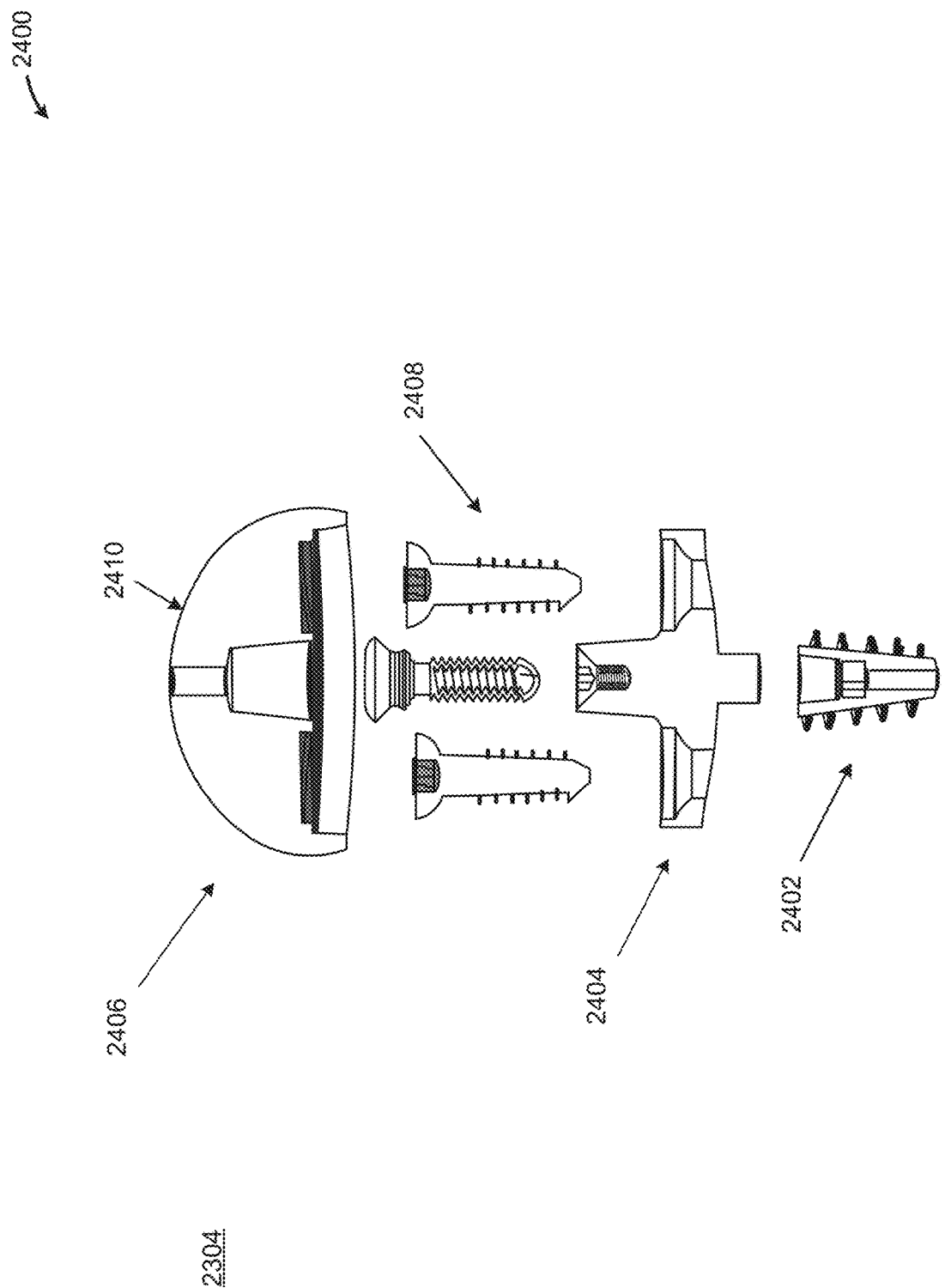
FIG. 24 generally illustrates an exploded view of one example of the second implant system and the second excision site consistent with the present disclosure.
Figure 25:
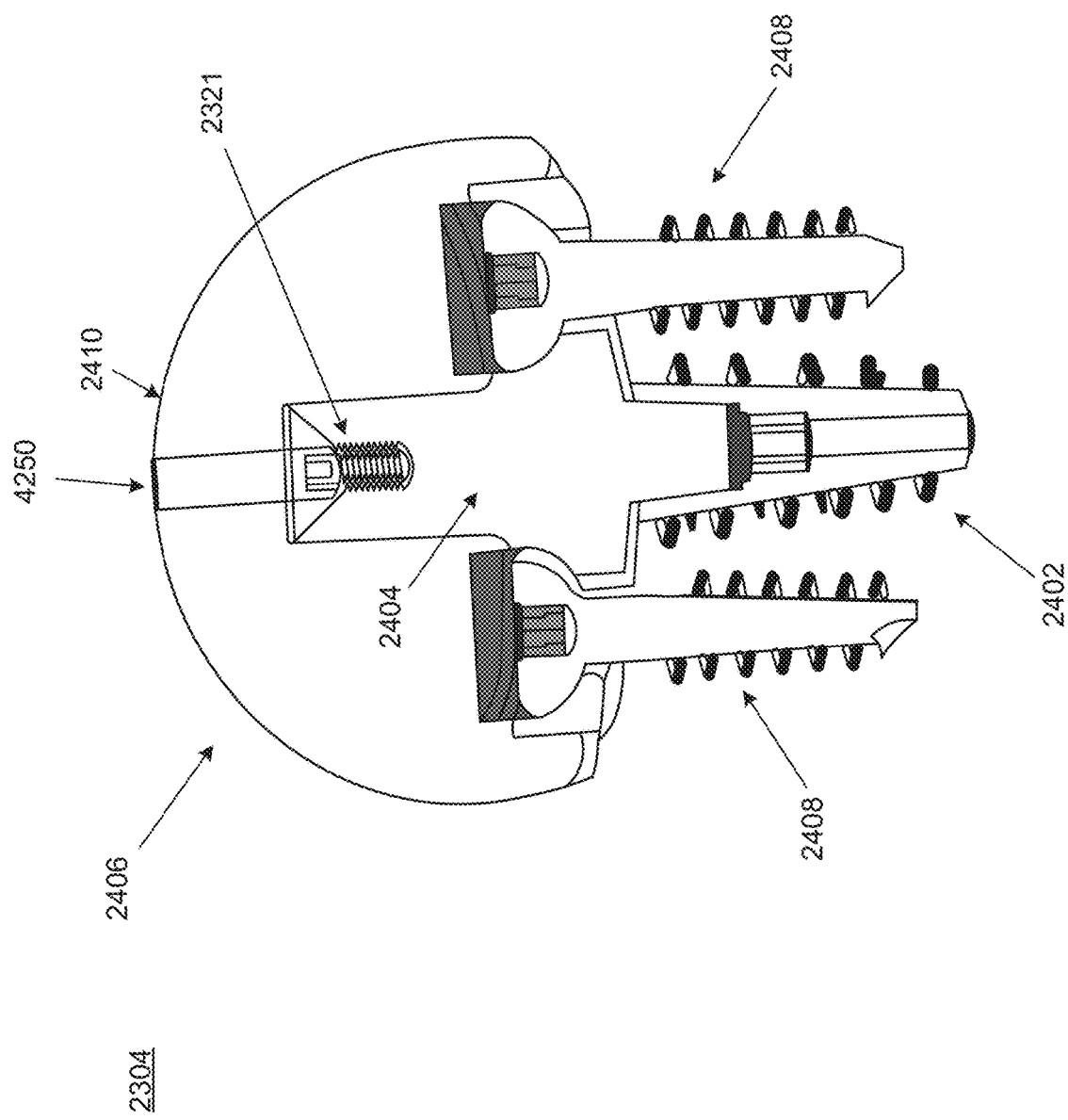
FIG. 25 generally illustrates an assembled view of one example of the second implant system and the second excision site consistent with the present disclosure.

The glenoid implant site 2300 may be formed in the glenoid 2302 in such a manner to aid in the positioning of the glenoid implant system 2404 and to reduce and/or prevent movement of the glenoid implant system 2404 relative to the glenoid 2302. At least a portion of the glenoid implant site 2300 may therefore be formed with a shape/contour/profile that inversely corresponds to the shape/contour/profile of at least a portion of the glenoid implant system 2404. As described herein, the glenoid implant system 2404, FIGS. 24-25, may include an anchor 2402, an intermediate component or base plate 2404, an implant 2406, an optionally one or more fasteners 2408 (such as, but not limited to, bone screws or the like). The anchor 2402 may be configured to be secured to the bone 2302 within the glenoid implant site 2300, the base plate 2404 may be configured to be secured to the anchor 2402 (and optionally to the bone 2302 using the fasteners 2408), and the implant 2406 may be configured to be secured to the base plate 2404. As shown, the implant 2406 includes a load bearing surface 2410 having a generally convex (e.g., semi-spherical and/or semi-ellipsoidal surface contour). While aspects/embodiments of the glenoid implant system 2304 may be described in the context of a reverse shoulder, it should be appreciated that the glenoid implant system 2304 is not limited to a reverse shoulder configuration. As such, the glenoid implant system 2304 may include a load bearing surface 2410 having any shape/contour/profile such as, but no limited to, a shape/contour/profile that corresponds to the patient's original, native shape/contour/profile.

Figure 26:
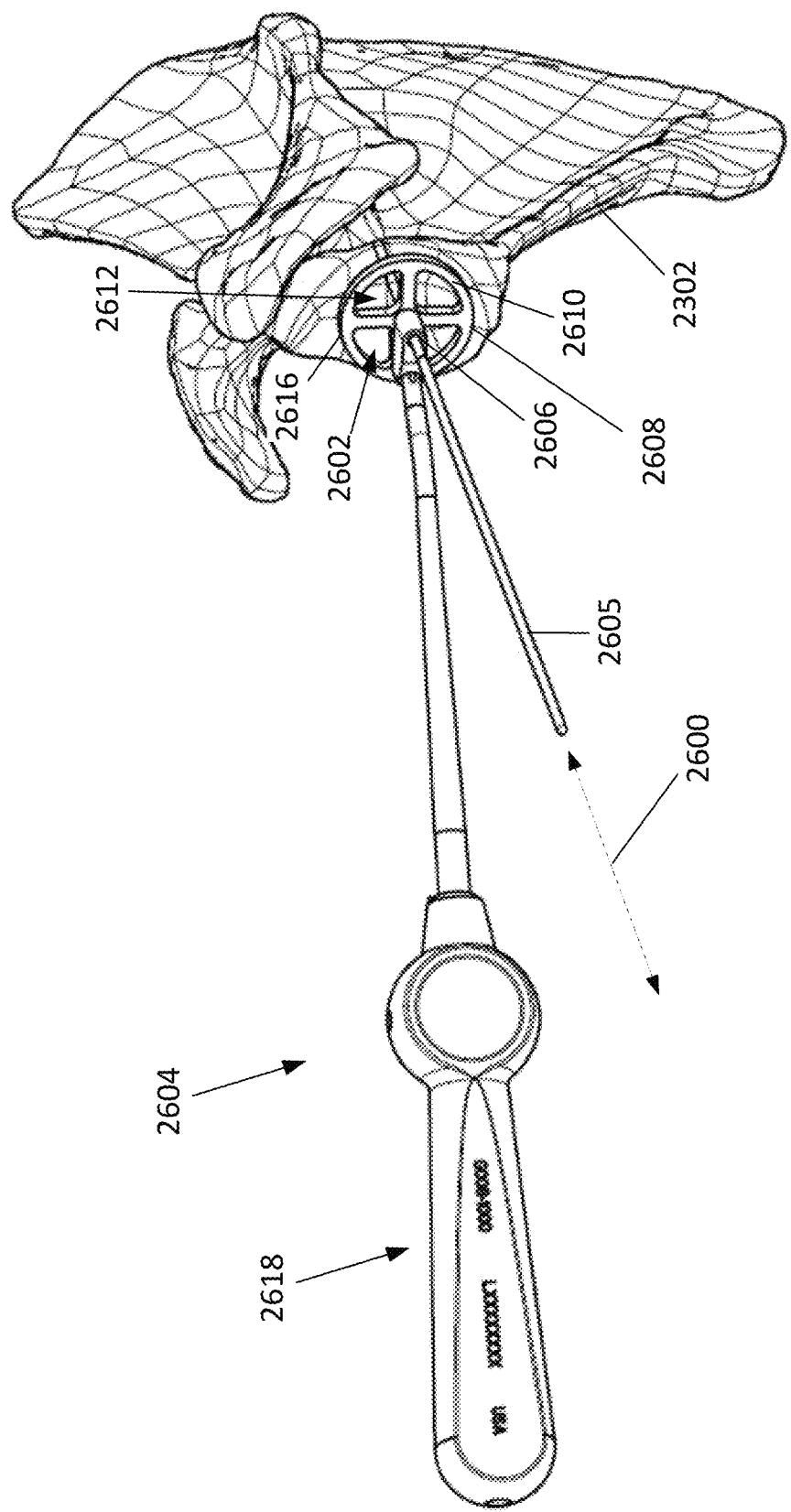
FIG. 26 generally illustrates one example of establishing a working axis consistent with the present disclosure.

Turning now to FIG. 26, a portion of one example of a system and method for forming the glenoid implant site 2300 in the glenoid 2302 to mate with glenoid implant system 2404 is generally illustrated. In particular, a working axis 2600 may be established. In the illustrated example, the working axis 2600 extends at an angle normal to lowest point on the patient's native articular surface 2602; however, it should be appreciated that the working axis 2600 may extend at any angle (which may be greater than or less than 90 degrees) and/or from any point along the patient's native articular surface 2602. The lowest point on the patient's native articular surface 2602 may be defined at the point on the patient's native articular surface 2602 that at the base of the glenoid socket.

The working axis 2600 may be established using a guide 2604. The guide 2604 may define a passageway 2606 formed in a guide body 2608 extending along the working axis 2600. The passageway 2606 may be configured to receive one or more pins 2605 such that the pin 2605 may be advanced through the passageway 2606 and secured into the bone 2302 along the working axis 2600, for example, using a drill or the like (not shown for clarity). The passageway 2606 may substantially correspond to the cross-section (e.g., diameter) of the outside of the pin 2605 to align the pin 2605 along the working axis 2600. The depth that the pin 2605 is secured into the bone 2302 may be set using the guide 2602. For example, the pin 2605 and/or the guide 2602 may include indicia (such as, but not limited to, laser markings, windows, shoulders, or the like) that may set the depth of the pin 2605 into the bone 2302.

The guide body 2608 may include one or more locating features 2610. The locating features 2610 may be sized and shaped to contact native articular surface 2602 and align/position the passageway 2606 relative to the native articular surface 2602. For example, the locating features 2610 may include a bottom surface having a contour that substantially matches and/or corresponds to the native contour of the patient's native articular surface 2602. As such, the locating features 2610 may be configured to engage and/or contact specific points of the glenoid 2300. The locating features 2610 may therefore have sizes and/or shapes based on the size and/or shape of the patient. The locating features 2610 may extend in one or more planes. For example, portions of the locating features 2610 may extend in two mutually perpendicular planes and/or portions of the locating features 2610 may extend along one or more arcs and/or circles. The guide body 2608 may include one or more windows 2612 configured to allow a surgeon to see portions of the native articular surface 2602. In one example, the locating features 2610 may be configured to substantially continuously contact against the native articular surface 2602 along one or more planes; however, it should be appreciated that the locating features 2610 may only contact a plurality of discrete points (such as, but not limited to, the outer periphery 2616). The guide 2602 may also optionally include a handle 2618 configured to allow a surgeon to grasp and position the guide 2602 relative to the native articular surface 2602.

Figure 27:
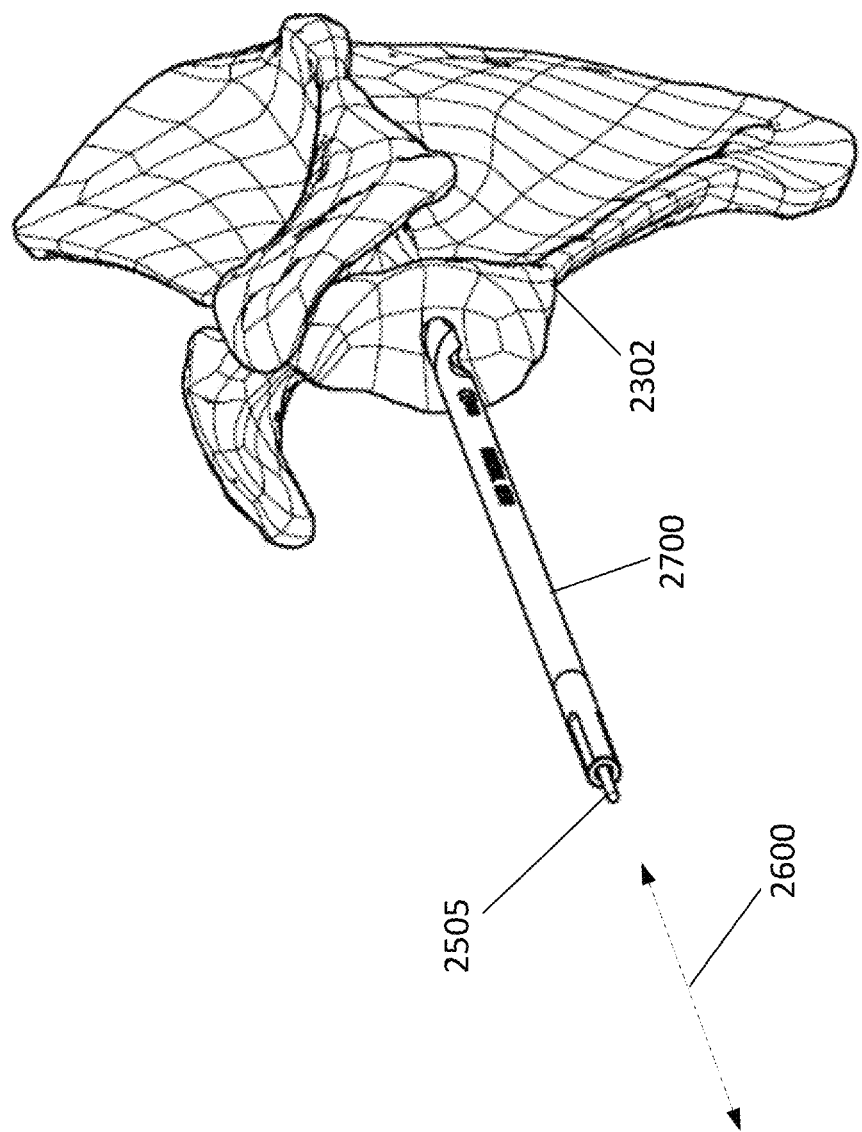
FIG. 27 generally illustrates one example of pin and a pilot bit along the working axis consistent with the present disclosure.
Figure 28:
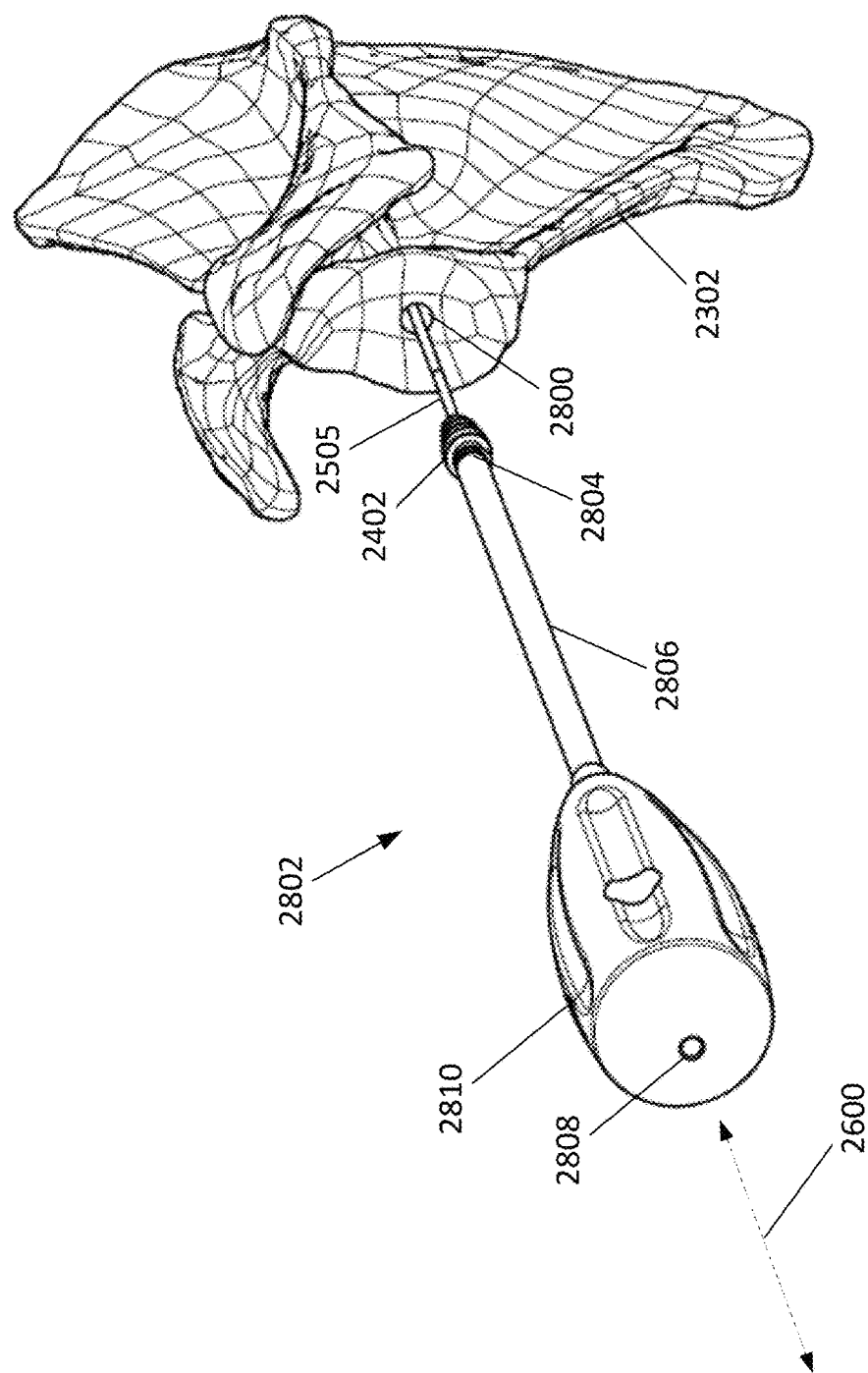
FIG. 28 generally illustrates one example of an anchor along the working axis consistent with the present disclosure.
Figure 29:
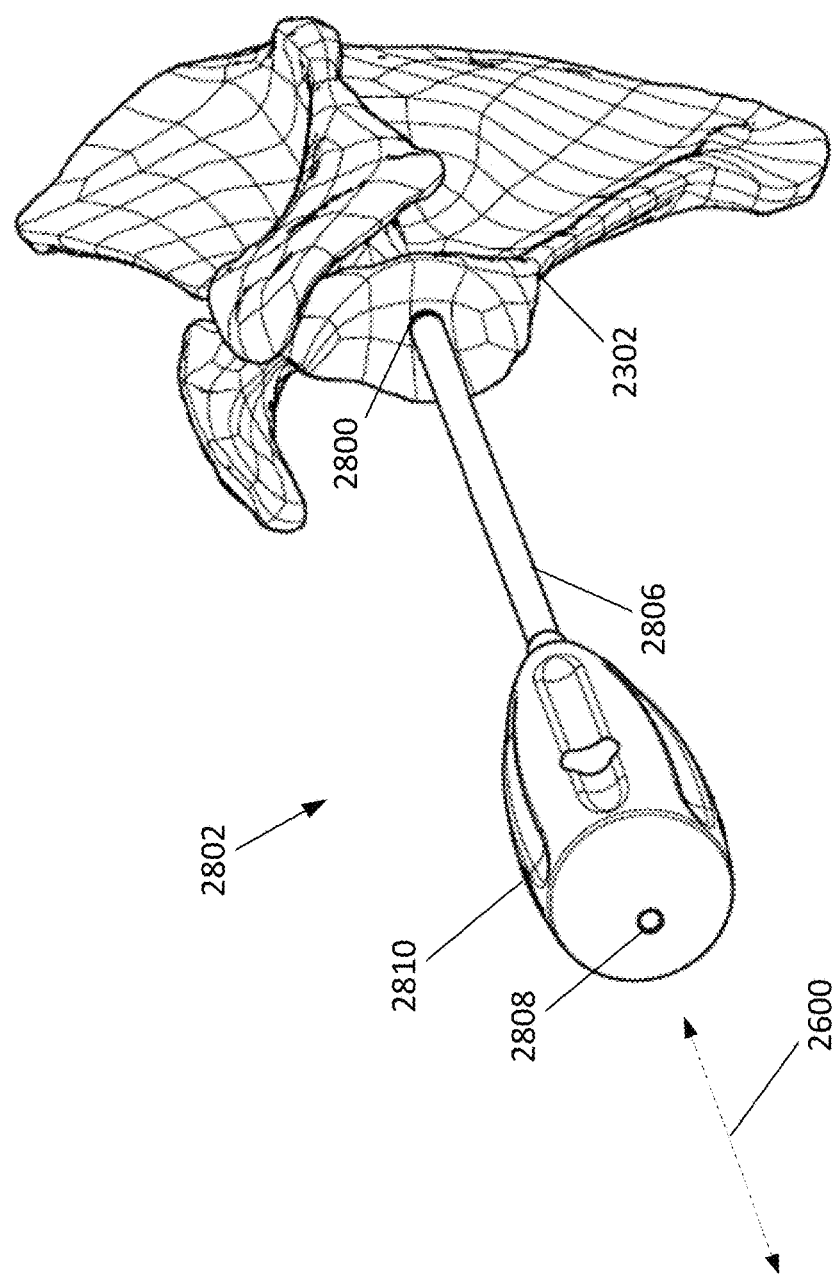
FIG. 29 generally illustrates one example of an anchor secured in the second bone along the working axis consistent with the present disclosure.

Once the pin 2605 is secured to the bone 2302 along the working axis 2300, the guide 2602 may be removed. Next, a cannulated drill 2700, FIG. 27, may be advanced over the pin 2605 to form a pilot hole 2800 in the bone 2302 centered around the pin 2605 as generally illustrated in FIG. 28. Once the pilot hole 2800 has been formed, an anchor 2402 of the glenoid implant system 2304 may be advanced and secured into the bone 2302 along the working axis 2600, e.g., into the pilot hole 2800 as shown in FIG. 29.

Turning now to FIGS. 30A-F, various views of one example of an anchor 2402 consistent with the present disclosure are generally illustrated. The anchor 2402 may include a body 3002, for example, having a tapered profile. The outside of the body 3002 may include one or more retaining elements (such as, but not limited to, threads, protrusions, ribs, barbs, recesses, or the like 3004) configured to engage the bone 2302 and secure the anchor 2402 to the bone 2302. The anchor 2402 may optionally be used with bone cement or the like. The outer surface of the anchor 2402 may be configured to facilitate bone regrow. The body 3002 may include a cannulated passageway 3006, for example, configured to be advanced over the pin 2605.

A proximal end 3008 of the anchor 2402 may include a fixation element 3010 configured to be coupled to a corresponding fixation element of the baseplate 2404 to secure the anchor 2402 to the baseplate 2404. For example, the fixation element 3010 may include a tapered interference fit (e.g., a Morse taper or the like). In the illustrated example, the fixation element 3010 is a female tapered recess configured to mate with a corresponding tapered male protrusion formed on the baseplate 2404; however, it should be appreciated that this arrangement may be reversed. Alternatively (or in addition), the fixation element 3010 may include any other mechanism and/or fastener for either permanently or removably coupling the anchor 2402 to the baseplate 2404 such as, but not limited to, snap fit connections, threaded connections, adhesives, or the like.

The proximal end 3008 of the anchor 2402 may optionally include a driving feature 3012. The driving feature 3012 may be configured to mate with a driver (such as a drill or the like) to secure the anchor 2402 into the bone 2302. For example, the driving feature 3012 may be configured to allow a drill to rotate the anchor 2402 into the bone 2302. In the non-limiting example, the driving feature 3012 is a hex recess.

Referring back to FIGS. 28-29, the anchor 2402 may be advanced over the pin 2605 using a driver 2802 (e.g., a hand drill or the like) having a corresponding driving feature 2804 (e.g., a hex head) configured to engage with the driving feature 3012 of the anchor 2402. The driver 2802 may include a cannulated shaft 2806 (defining a passageway 2808) with the driving feature 2804 at one end, and a handle 2810 proximate the other end. The anchor 2402 and the driver 2802 may be advanced over the pin 2505 along the working axis 2600. The driving feature driving feature 2804 of the driver 2802 may then be coupled to the driving feature 3012 of the anchor 2402 to secure (e.g., rotate) the anchor 2402 around the working axis 2600 into the bone 2302 within the pilot hole 2800. The depth of the anchor 2402 within the bone 2302 may be set using indicia on the driver 2802 and/or pin 2505 (such as, but not limited to, laser markings, windows, shoulders, or the like) as generally illustrated in FIG. 29.

Figure 31:
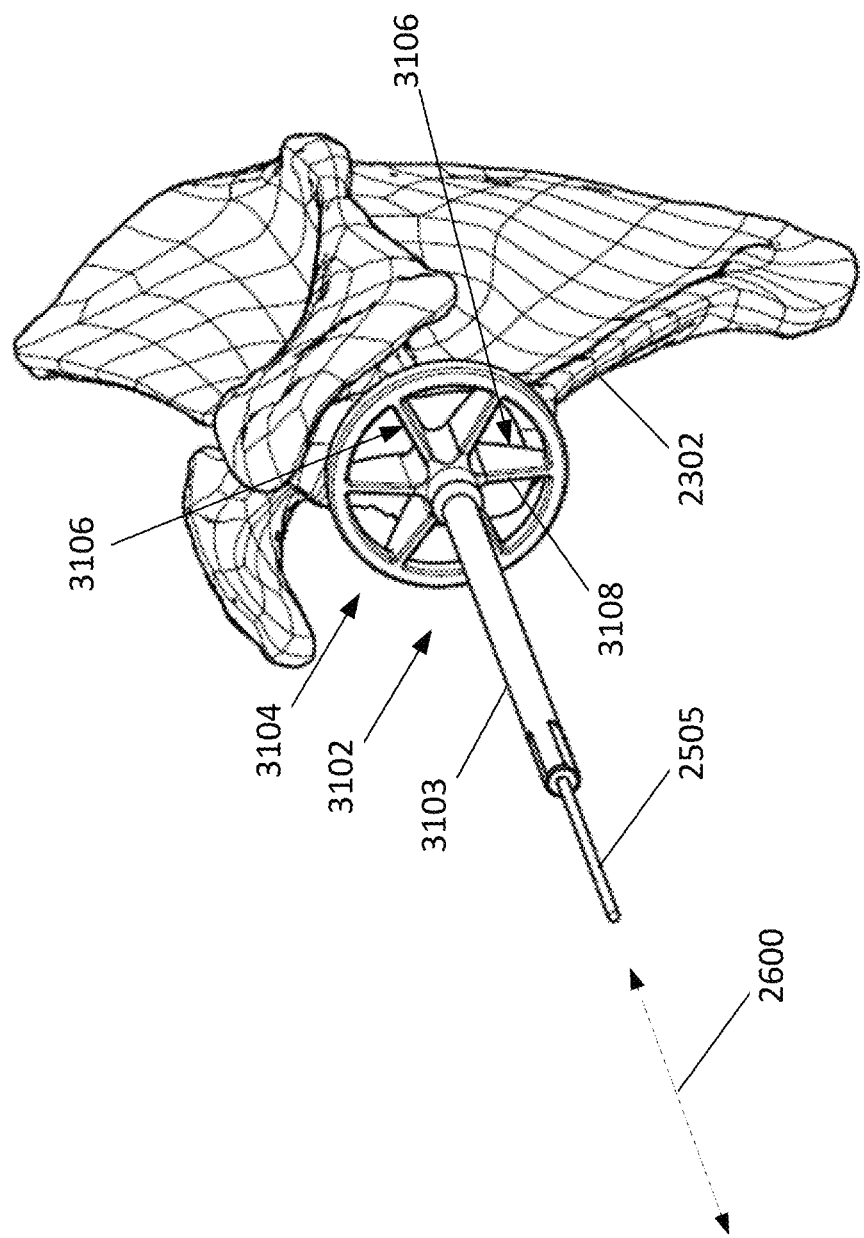
FIG. 31 generally illustrates one example of a reamer for forming the second excision site along the working axis consistent with the present disclosure.
Figure 32:
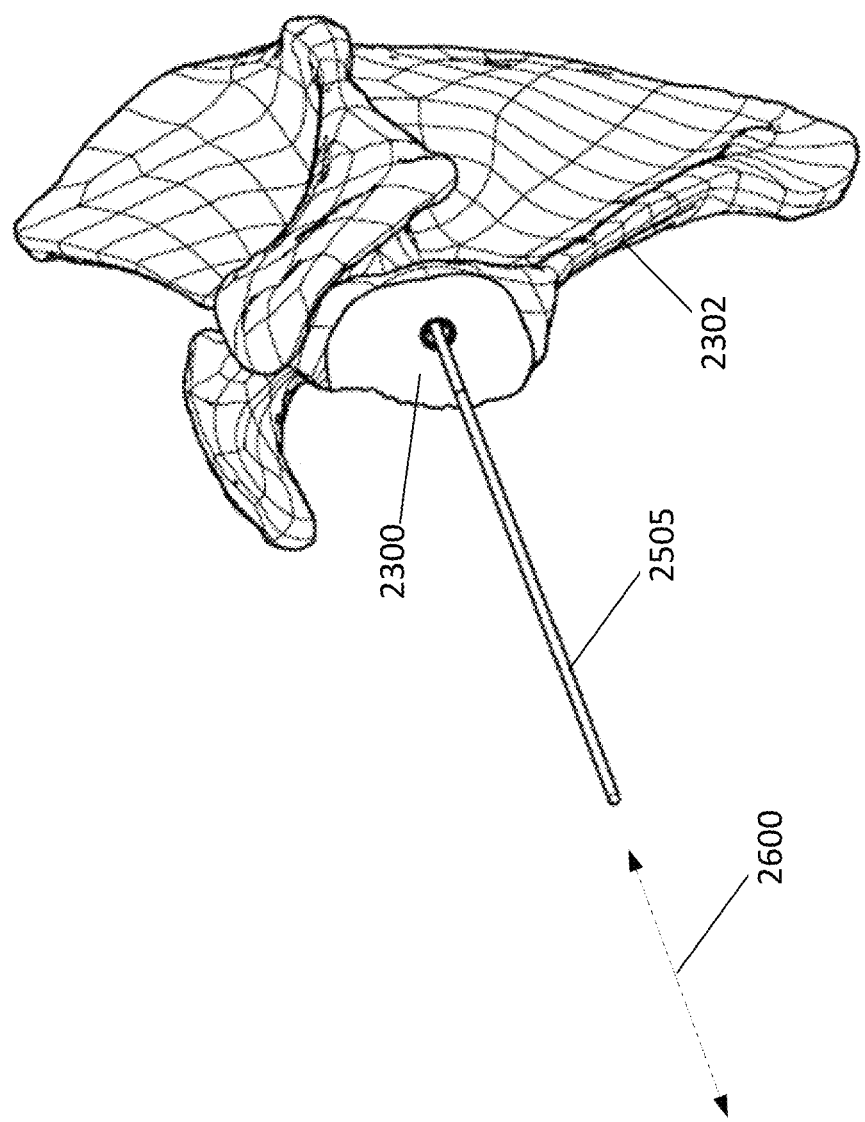
FIG. 32 generally illustrates one example of the second excision site in the second bone consistent with the present disclosure.

Turning now to FIG. 31, once the anchor 2402 has been set in place in the bone 2302, the driver 2802 may be removed. Optionally, an initial cut (e.g., a scrim cut) may be performed on the native articular surface 2602 to true-up and create a uniform surface, which may at least partially form the glenoid implant site 2300 (FIG. 32). For example, a truing reamer 3102 (FIG. 31) may be rotated and advanced along the working axis 2600 (e.g., to form at least a portion of the glenoid implant site 2300). In the illustrated example, the truing reamer 3102 may include a cannulated shaft 3103 configured to be rotated and advanced over the pin 2505 and revolved around the working axis 2600. A distal end region 3104 of the truing reamer 3102 may include one or more cutting surfaces 3106 configured to remove at least a portion of the native articular surface 2602. For example, the truing reamer 3102 may include one or more cutting arms 3108 extending radially outward from the shaft 3102. The cutting arms 3108 may include one or more cutting surfaces 3106, for example, having a generally flat, planar, and/or arcuate shape. The truing reamer 3102 may be used to form at least a portion of the glenoid implant site 2300 (FIG. 32) which is revolved around the working axis 2600. The cutting surfaces 3106, when revolved around the working axis 2600, may inversely correspond to (e.g., define) the contours of the bone facing surface of the baseplate 2404 as described herein.

In at least one example, the cutting surfaces 3106 of the truing reamer 3102 may be configured to form a generally planar shape/surface. Alternatively (or in addition), the cutting surfaces 3106 may be formed by one curves, two or more tangential curves, and/or curves having one or more inflection points. The truing reamer 3102 may be advanced along the working axis 2600 until a portion of the truing reamer 3102 (e.g., a central portion) contacts/abuts against a portion of the anchor 2402. Alternatively (or in addition), the depth of the truing reamer 3102 along the working axis 2600 may be set/determined using indicia/markings on the pin 2505 and/or the truing reamer 3102. While the glenoid implant site 2300 (FIG. 32) is shown having a generally concaved surface formed by the truing reamer 3102, it should be appreciated that the glenoid implant site 2300 may alternatively (or in addition) have a generally planar and/or convex shape. As such, the glenoid implant site 2300 is not limited to the illustrated shape unless specifically claimed as such.

Figure 33:
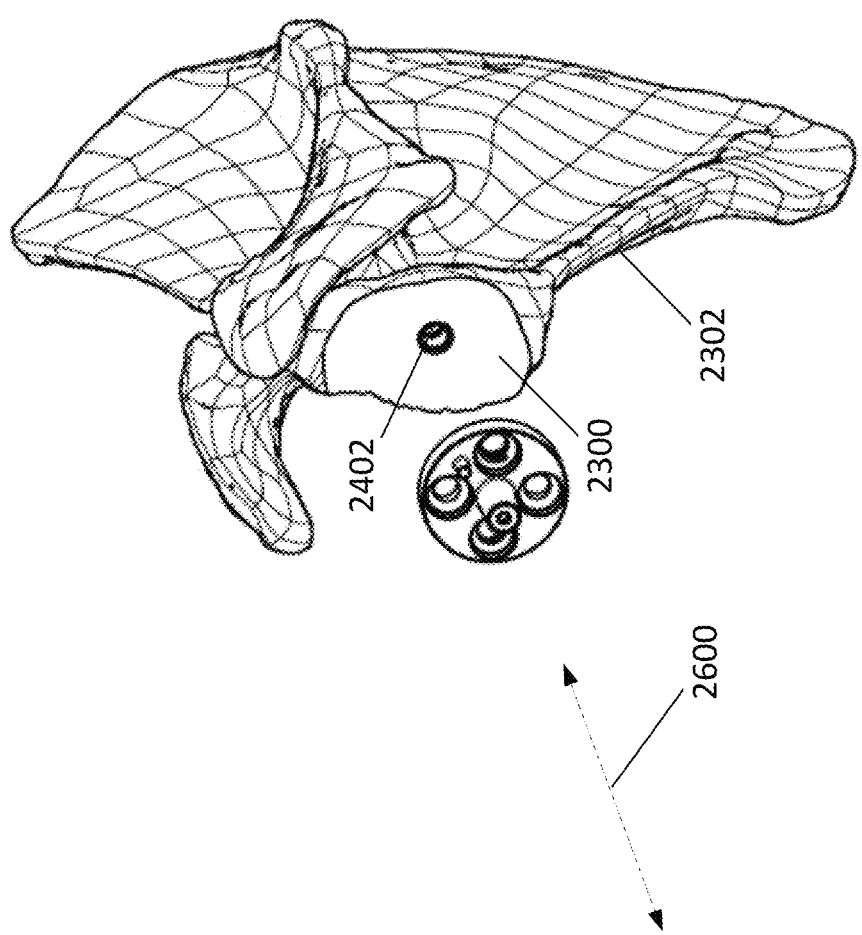
FIG. 33 generally illustrate one example of a baseplate being and the second excision site consistent with the present disclosure.
Figure 34G:
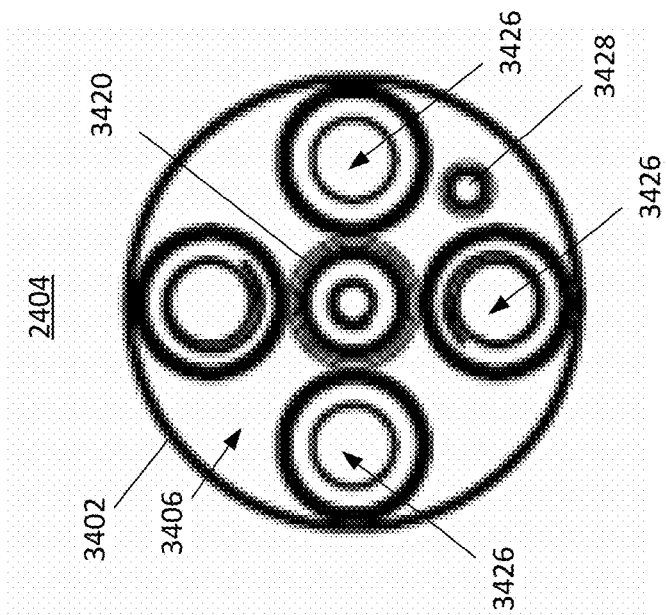
Figure 34E:
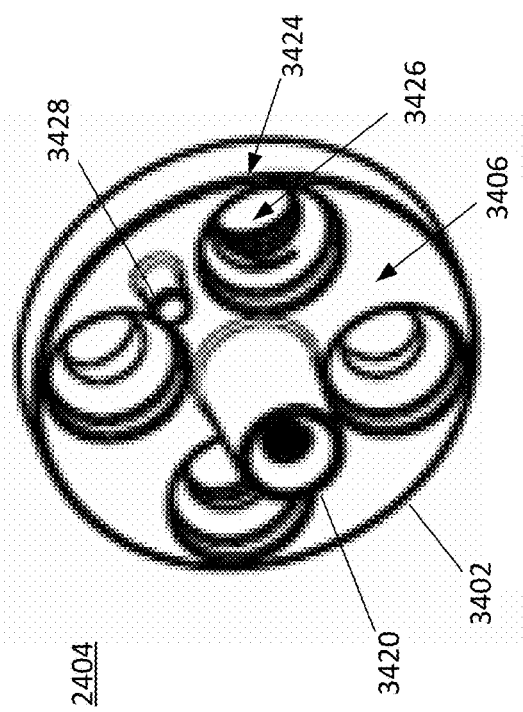
Figure 34F:
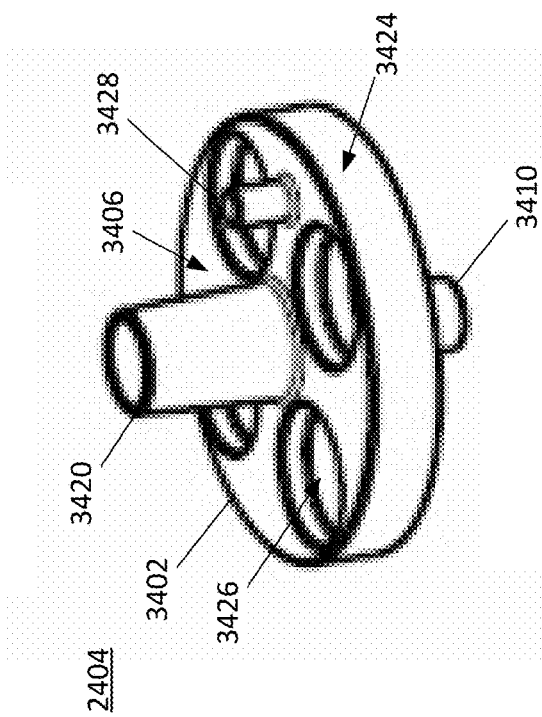

Turning now to FIG. 33, the pin 2505 may optionally be removed and the baseplate 2404 may be secured to the anchor 2402. FIGS. 34A-E generally illustrates various views of one example of a baseplate 2404 consistent with the present disclosure. The baseplate 2404 may include a body 3402 defining a bone facing surface 3404 and an implant facing surface 3406. The bone facing surface 3604 may have a profile substantially inversely corresponding to the profile of the glenoid implant site 2300 (e.g., a profile substantially inversely corresponding to the profile of the cutting surfaces 3106 of the truing reamer 3102 when revolved around the working axis 2600). For example, the bone facing surface 3604 may have generally convex surface corresponding to the concaved surface of the glenoid implant site 2300. The bone facing surface 3604 may therefore have a cross-section (e.g., a diameter) that corresponds to the cross-section (e.g., diameter) of the cutting surfaces 3106 of the truing reamer 3102 when revolved around the working axis 2600.

The baseplate 2404 may include an anchor fixation element 3410 configured to be coupled to the corresponding fixation element 3010 of the anchor 2402 to secure the baseplate 2404 to the anchor 2402. As discussed herein, the fixation elements 3010, 3410 may include a tapered interference fit (e.g., a Morse taper or the like). In the illustrated example, the anchor fixation element 3410 is a male tapered protrusion extending outward from the bone facing surface 3404 configured to mate with a corresponding tapered female recess formed on the anchor 2402; however, it should be appreciated that this arrangement may be reversed. Alternatively (or in addition), the fixation elements 3010, 3410 may include any other mechanism and/or fastener for either permanently or removably coupling the anchor 2402 to the baseplate 2404 such as, but not limited to, snap fit connections, threaded connections, adhesives, or the like. The fixation elements 3010, 3410 may be aligned along the working axis 2600. Alternatively, the fixation elements 3010, 3410 may not be coaxial with the working axis 2600.

The bone facing surface 3604 may optionally include one or more retaining elements (such as, but not limited to, threads, protrusions, ribs, barbs, recesses, or the like) configured to engage the bone 2302 of the glenoid excision site 2300 and secure the baseplate 2404 to the bone 2302. The baseplate 2404 may optionally be used with bone cement or the like. The bone facing surface 3404 of the baseplate 2404 may be configured to facilitate bone regrow.

The implant facing surface 3406 of the baseplate 2404 may be configured to be coupled to the implant 2406. The implant facing surface 3406 may have a generally planar, concave, and/or convex shape configured to receive at least a portion of the implant 2406. For example, the implant facing surface 3406 may have a generally planar shape that generally corresponds to a baseplate interface surface of the implant 2304. According to one example, the baseplate 2404 may include one or more implant fixation elements 3420 configured to be coupled to a corresponding fixation element of the implant 2304 to secure the implant 2304 to the baseplate 2404. In at least one example, the implant may include a tapered interference connection (e.g., a Morse taper or the like). For example, implant fixation element 3420 may include a male tapered protrusion extending outward from the implant facing surface 3406 configured to mate with a corresponding tapered female recess formed on the implant 2406; however, it should be appreciated that this arrangement may be reversed. Alternatively (or in addition), the fixation elements 3420 may include any other mechanism and/or fastener for either permanently or removably coupling the baseplate 2404 to the implant 2306 such as, but not limited to, snap fit connections, threaded connections, adhesives, or the like. The implant fixation element 3420 may be aligned along the working axis 2600. Alternatively, the implant fixation element 3420 may not be coaxial with the working axis 2600.

The baseplate 2404 may have a thickness 3422 configured to position the implant 2306 at the desired position relative to the bone 2302. The outer surface 3424 of the body 3402 of the baseplate 2404 may have a generally frusto-conical, frusto-spherical shape, and/or generally cylindrical shape.

The baseplate 2404 may optionally include one or more apertures 3426 configured to receive one or more fasteners (e.g., a bone screw or the like). The apertures 3426 may extend through the body 3402 (e.g., between the bone facing surface 3404 and the implant facing surface 3406). The fasteners may aid in retaining the baseplate 2404 to the bone 2302 and/or prevent movement (e.g., rotation) of the baseplate 2404 relative to the bone 2302.

The baseplate 2404 (e.g., the implant facing surface 3406) may optionally include one or more implant alignment elements or features 3428. The implant alignment features 3428 may be configured to generally align the implant 2406 relative to the baseplate 2404 and/or prevent movement (e.g., rotation) of the implant 2406 relative to the baseplate 2404. In the illustrated embodiment, the implant alignment features 3428 includes a post extending outward from the implant facing surface 3406 that is configured to be received in a corresponding recess formed in the implant 2406. The post may optionally be tapered (e.g., to form a Morse taper or the like). Of course, the implant alignment features 3428 are not limited to this configuration. For example, the arrangement of the post and the recess may be reversed.

Figure 35:
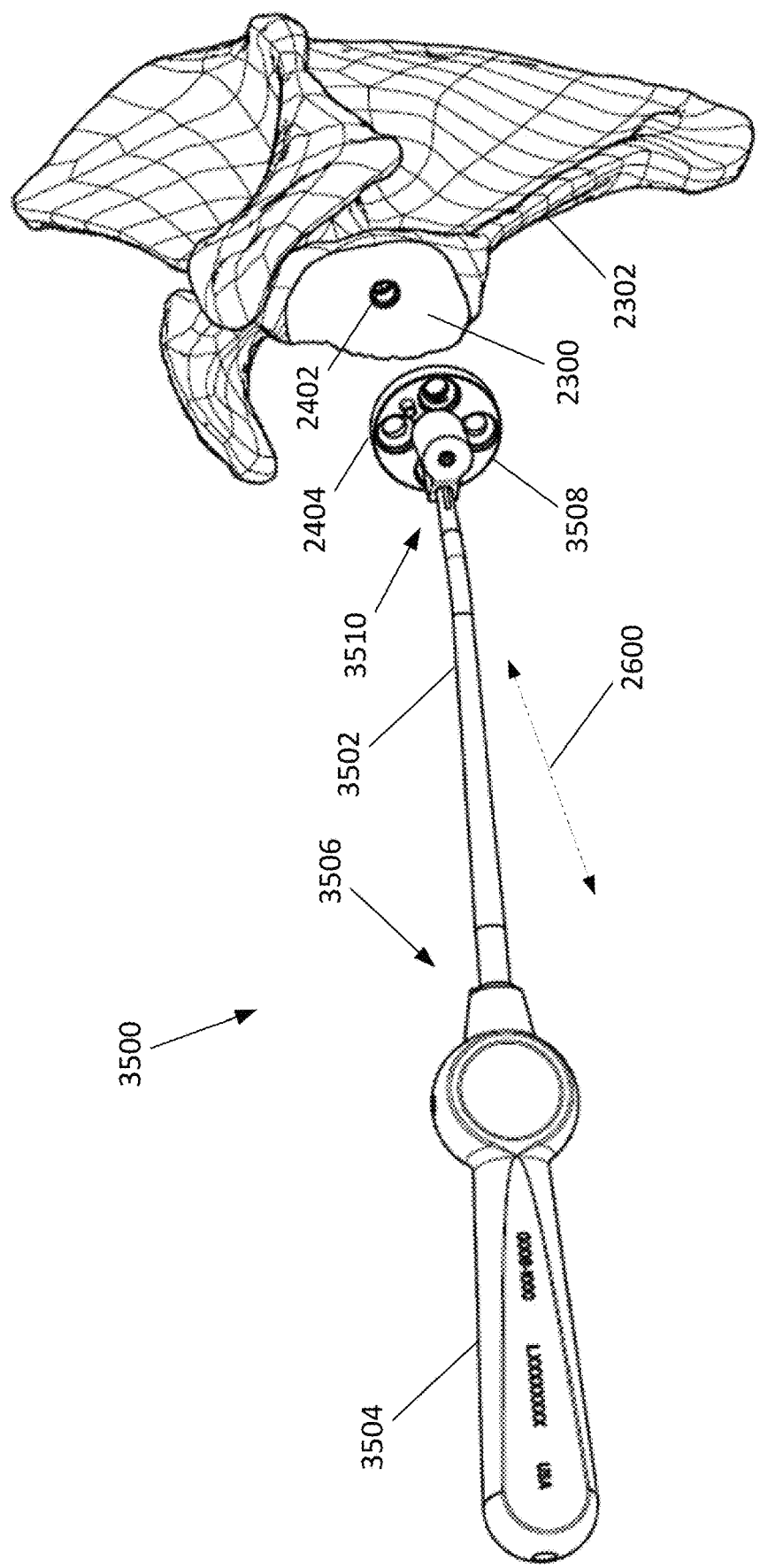
FIG. 35 generally illustrate one example of a baseplate being advanced to the second excision site consistent with the present disclosure.
Figure 36:
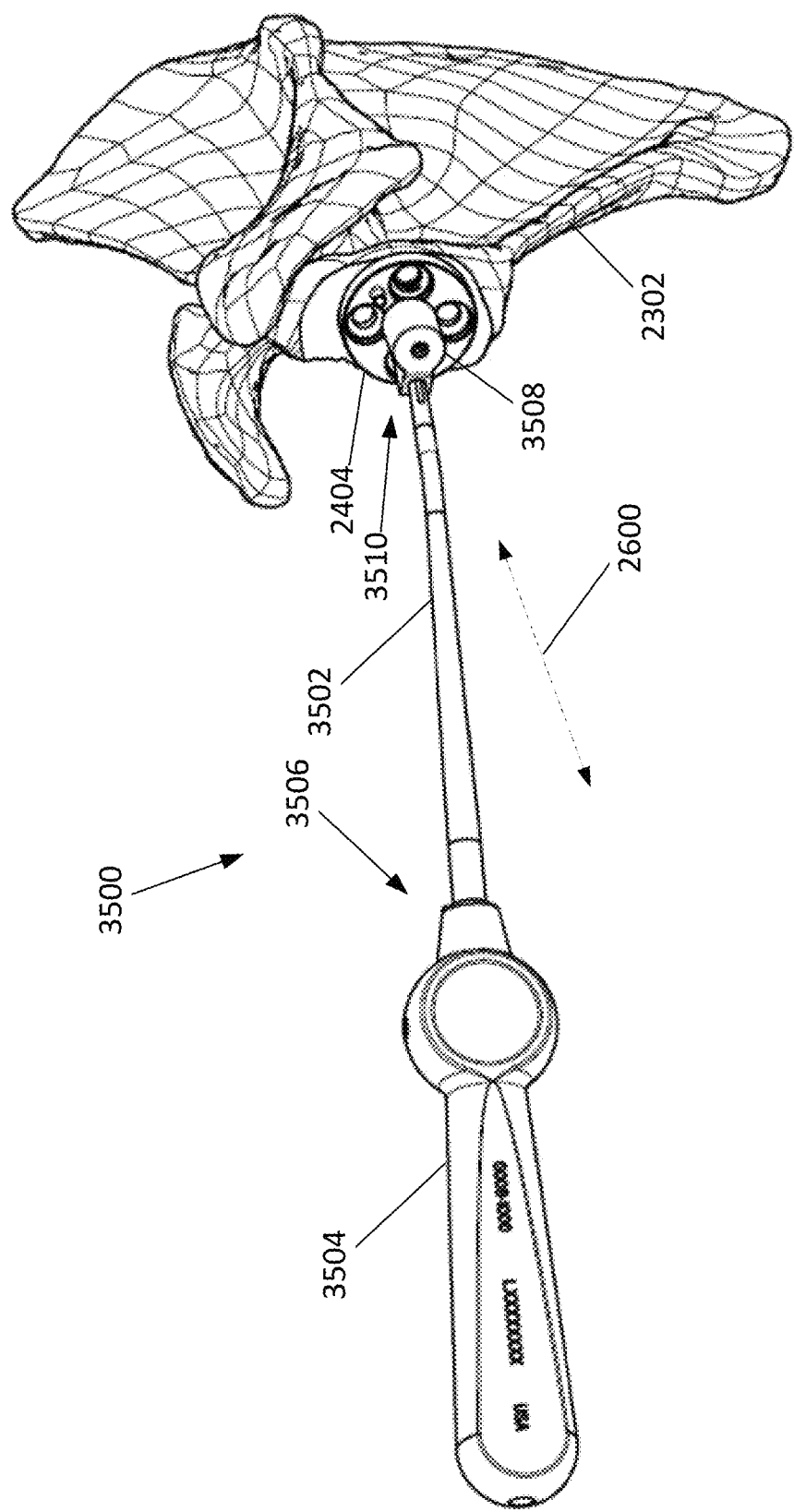
FIGS. 36-37 generally illustrate one example of a baseplate being on the second excision site consistent with the present disclosure.

With reference to FIGS. 35-36, the baseplate 2404 may be located on the glenoid implant site 2300 using a holder 3500. The holder 3500 may include a shaft 3502, a handle 3504 at one end region 3506 of the shaft 3502, and a coupler 3508 at the other end region 3510 of the shaft 3502. In the illustrated example, the coupler 3508 may be configured to be secured to the implant fixation element 3420 of the baseplate 2404 (e.g., using a Morse taper connection or the like); however, it should be appreciated that this is only one example and that the coupler 3508 may be configured to be secured to the baseplate 2404 in any manner known to those skilled in the art.

Figure 37:
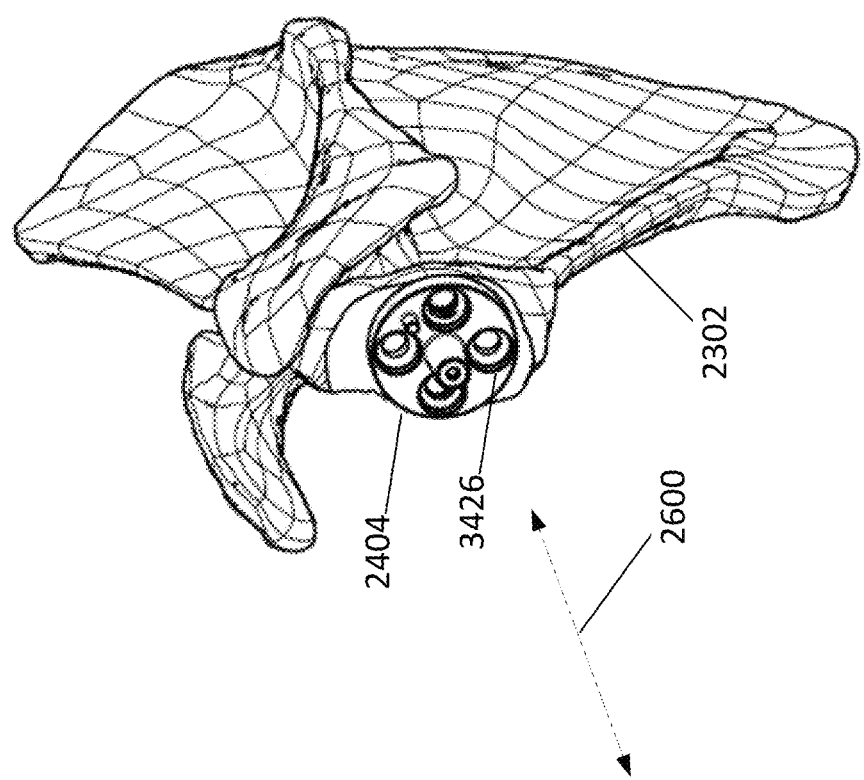
Figure 38:
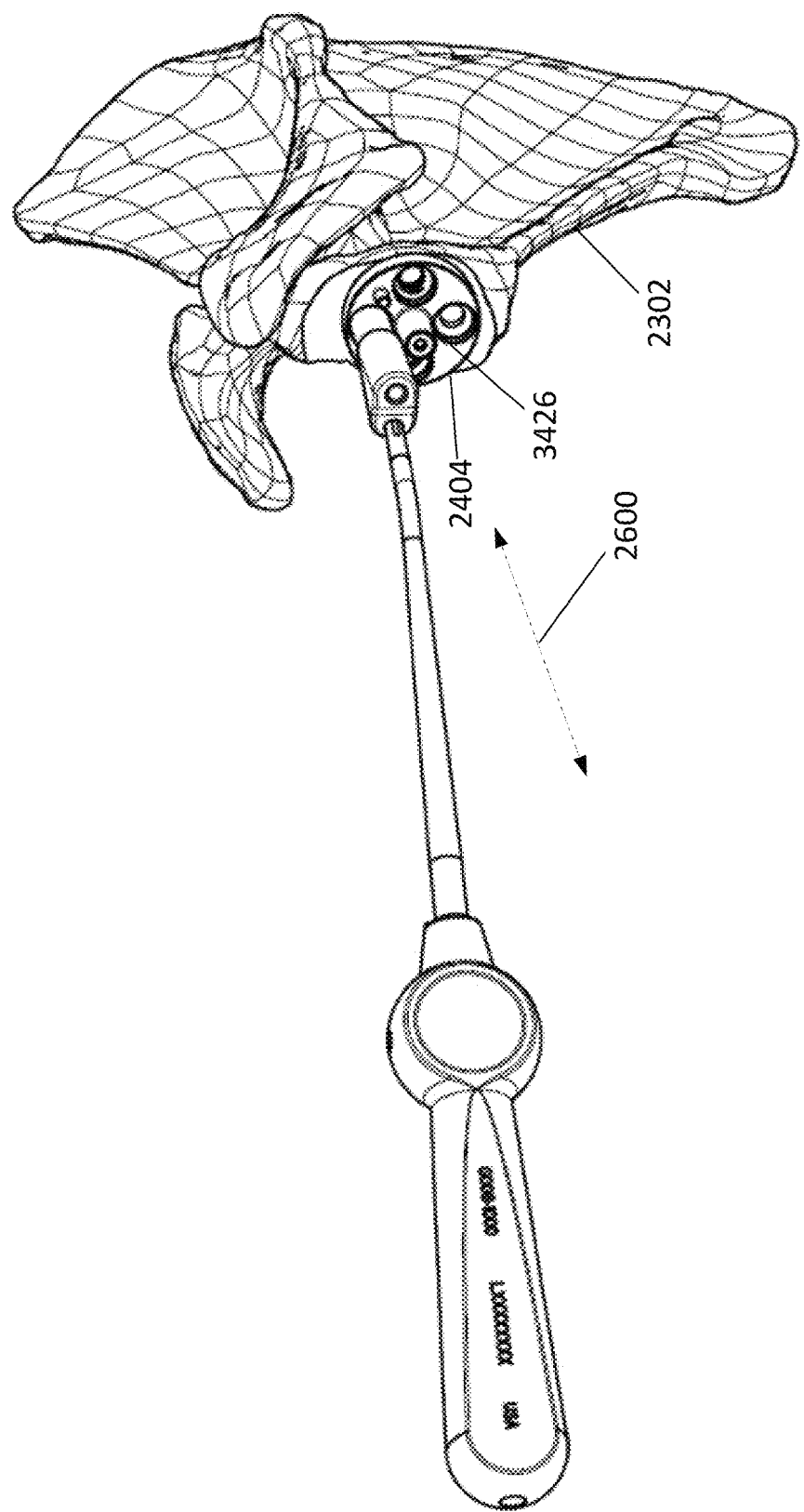
FIG. 38 generally illustrate one example of a pilot holes being formed in the second excision site consistent with the present disclosure.
Figure 39:
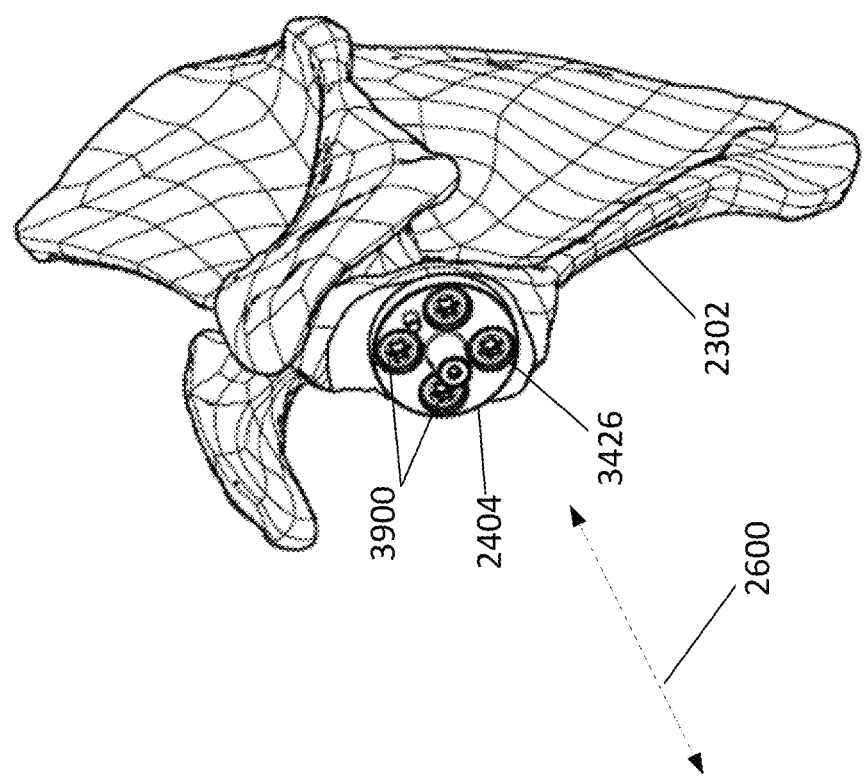
FIG. 39 generally illustrate one example of a baseplate being secured to the second excision site consistent with the present disclosure.

Once the baseplate 2404 has been set in place relative to the glenoid implant site 2300, the baseplate 2404 may be secured to the anchor 2402 as generally illustrated in FIG. 37. For example, the anchor fixation element 3410 configured to be coupled to the corresponding fixation element 3010 of the anchor 2402 to secure the baseplate 2404 to the anchor 2402. Optionally, the baseplate 2404 may be secured to the bone 2302 using one or more fasteners (e.g., bone screws) disposed through the apertures 3426 in the body 3402 baseplate 2404. In the illustrated example, pilot holes may be formed that are aligned with the apertures 3426. For example, a pilot hole drill guide 3800, FIG. 38, may be used to create pilot holes in the bone 2302 within the glenoid implant site 2300 that are aligned with the apertures 3426. The pilot hole drill guide 3800 may include a bushing 3802 or the like configured to be received in a portion of the aperture 3426 (or a cavity configured to receive a portion of the baseplate 2404) that aligns a passageway 3804 of the bushing 3802 with the aperture 3426. Next, a drill bit may be advanced through the passageway 3804 of the bushing 3802 and into the bone 2302 to form the pilot holes. The bushing 3802 may be aligned with (e.g., coupled to) all of the apertures 3426 to form the desired pilot holes. After the pilot holes are formed, one or more fasteners 3900, FIG. 39, may be advanced through the apertures 3426 to secure the baseplate 2404 to the bone 2302. The fasteners 3900 may include any fastener known to those skilled in the art such as, but not limited to, bone screws, posts, pins, or the like.

Figure 40:
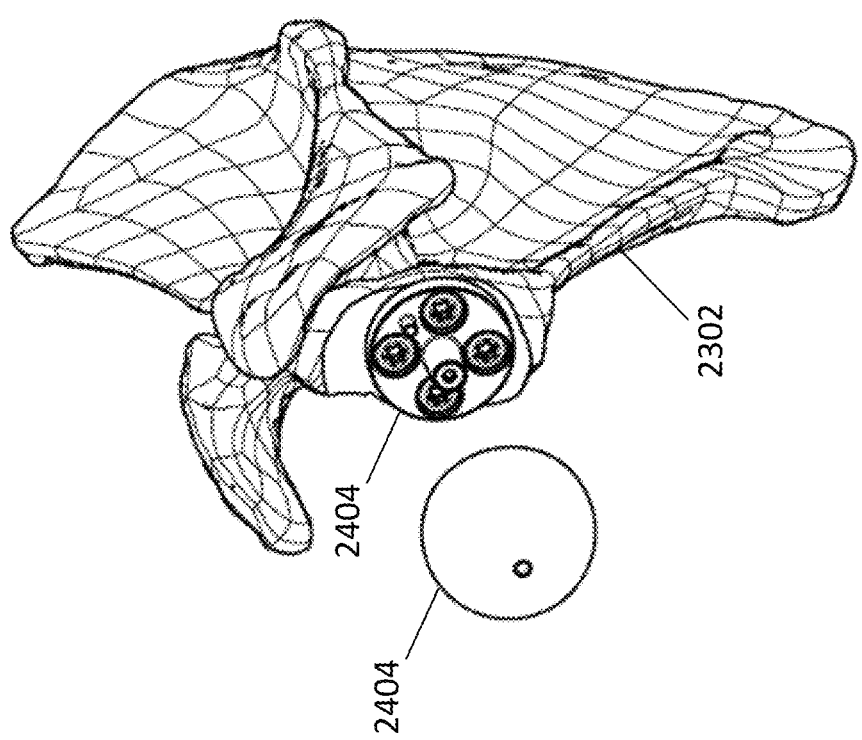
FIG. 40 generally illustrate one example of an implant and a baseplate consistent with the present disclosure.
Figure 41:
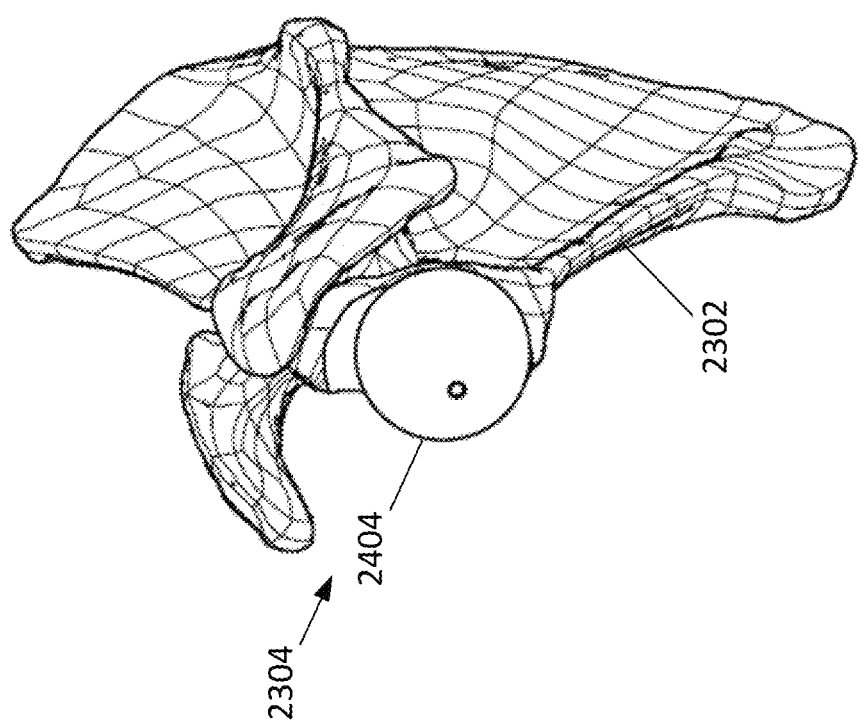
FIG. 41 generally illustrate one example of an implant secured to a baseplate consistent with the present disclosure.
Figure 42D:
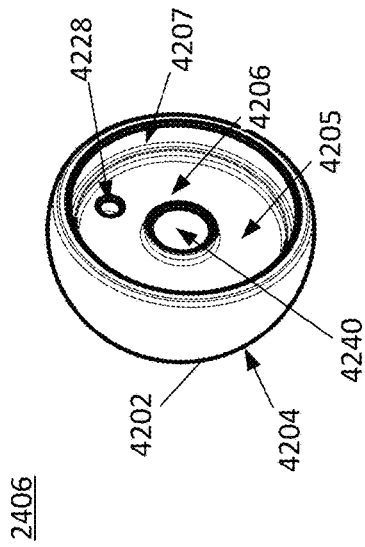
FIGS. 42A-E generally illustrate various views of one example of the implant consistent with the present disclosure.
Figure 42E:
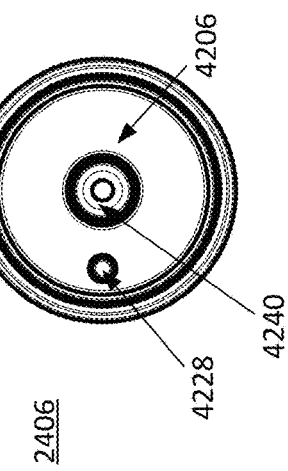
Figure 42A:
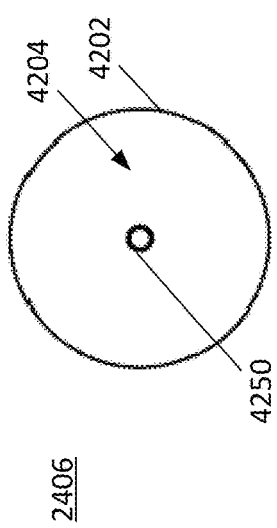
Figure 42B:
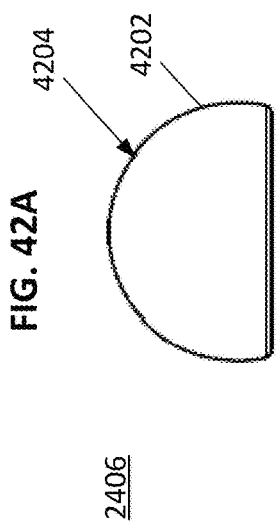
Figure 42C:
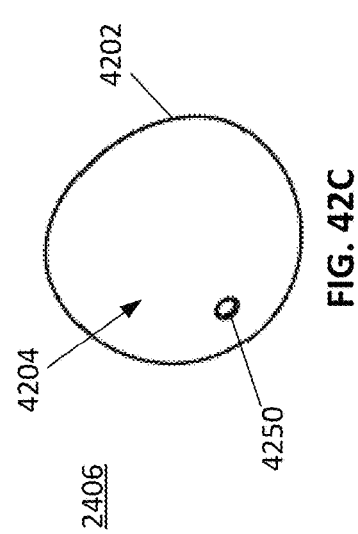
Figure 43:
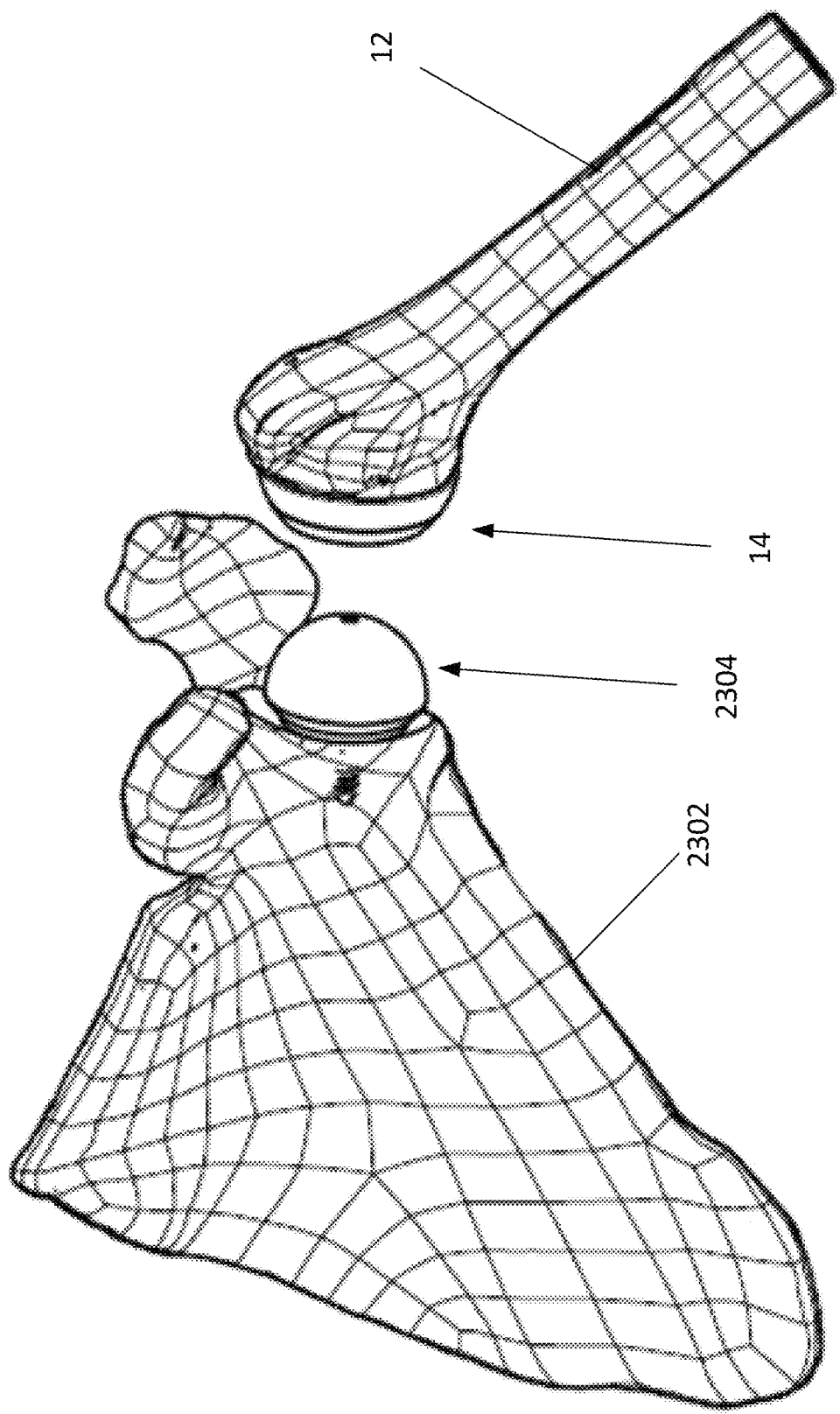
Figure 44:
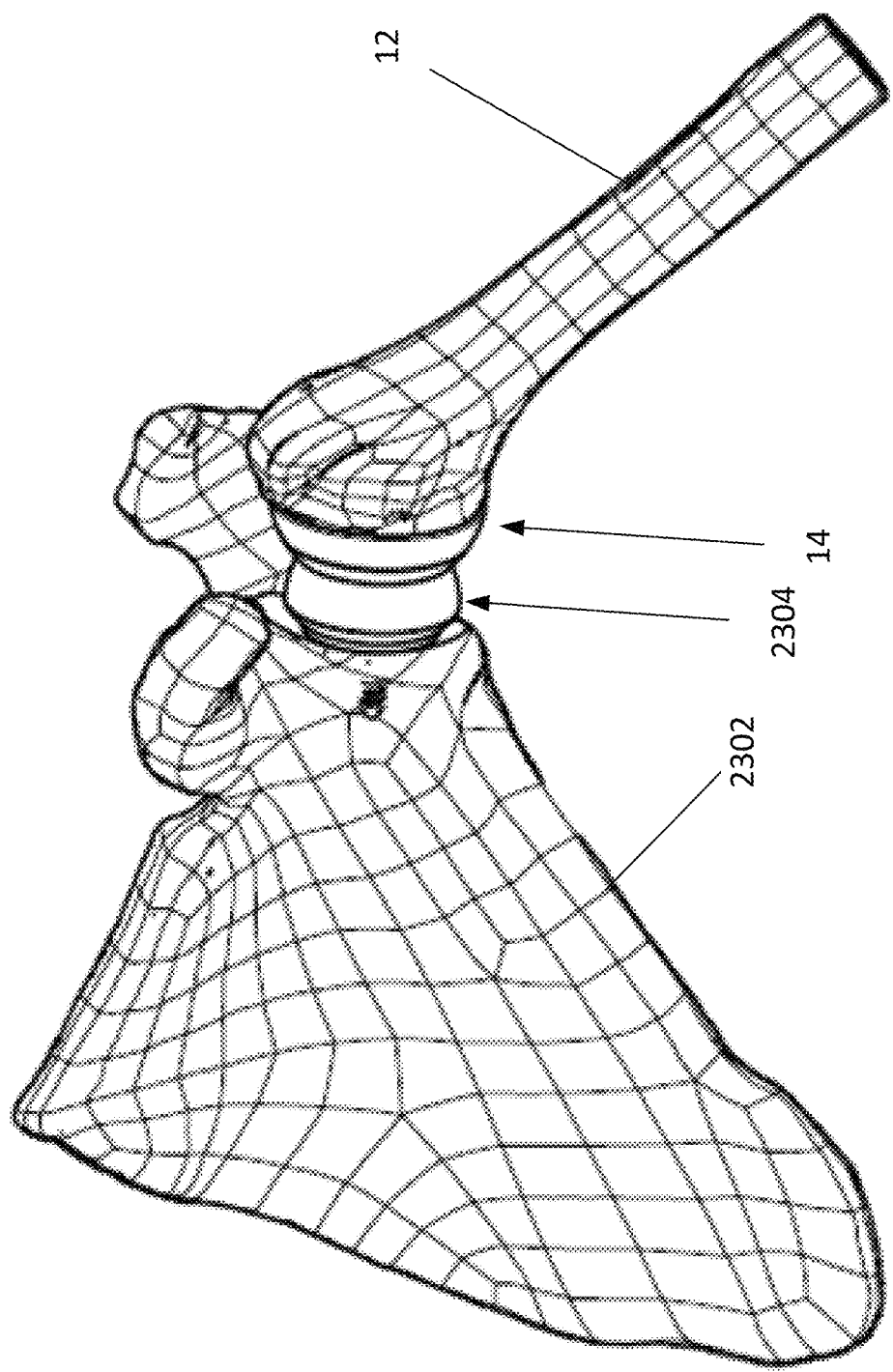
Figure 45:
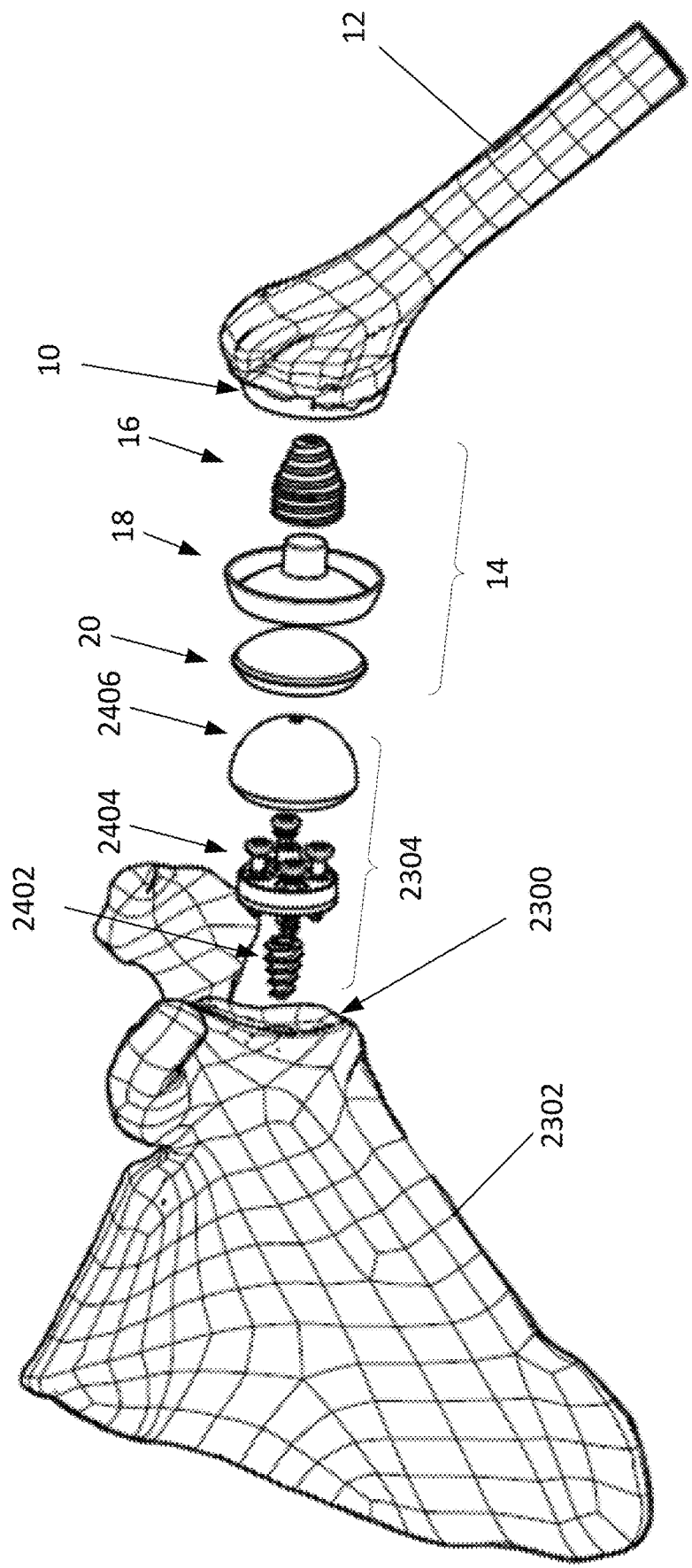
Figure 46:
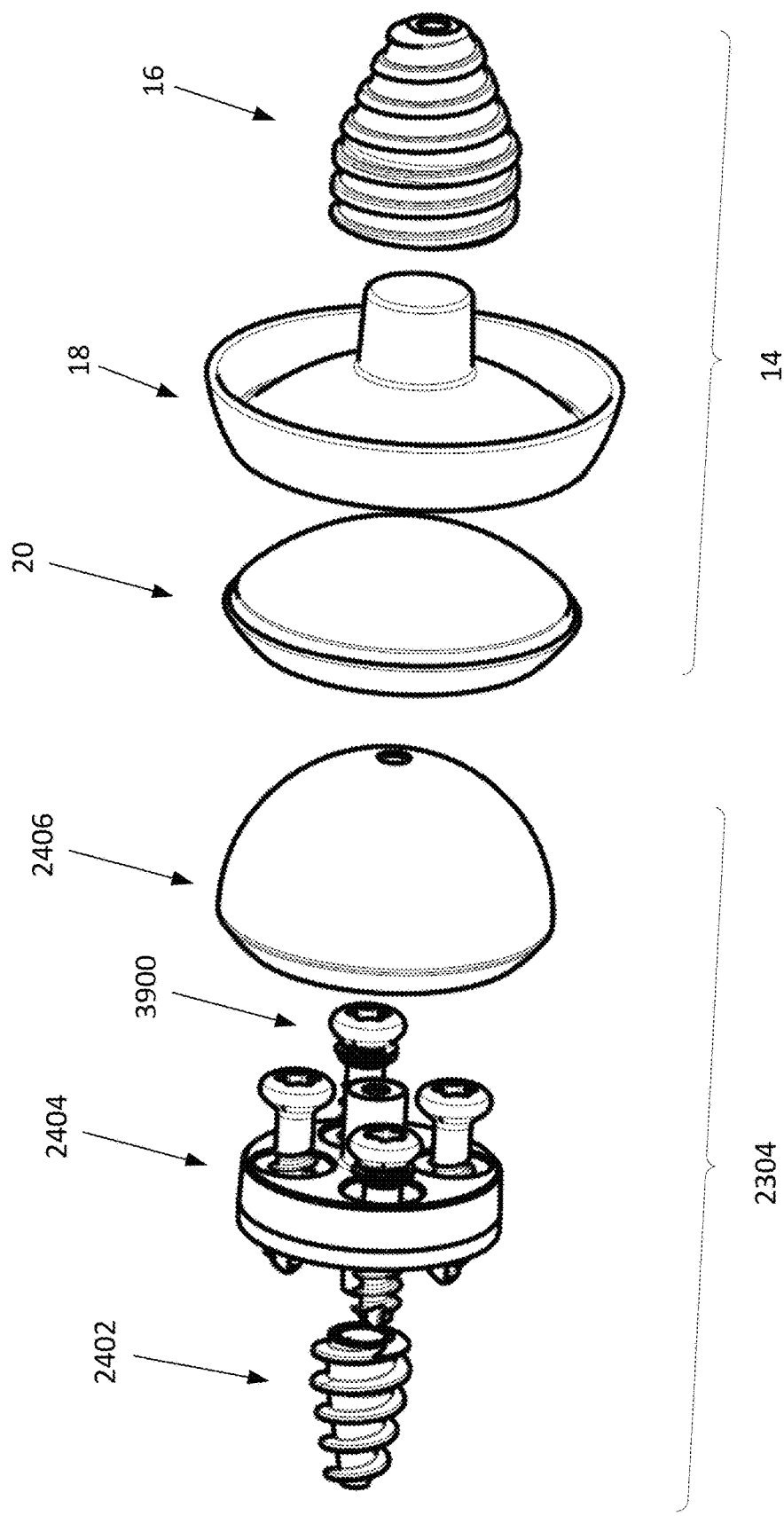
Figure 48:
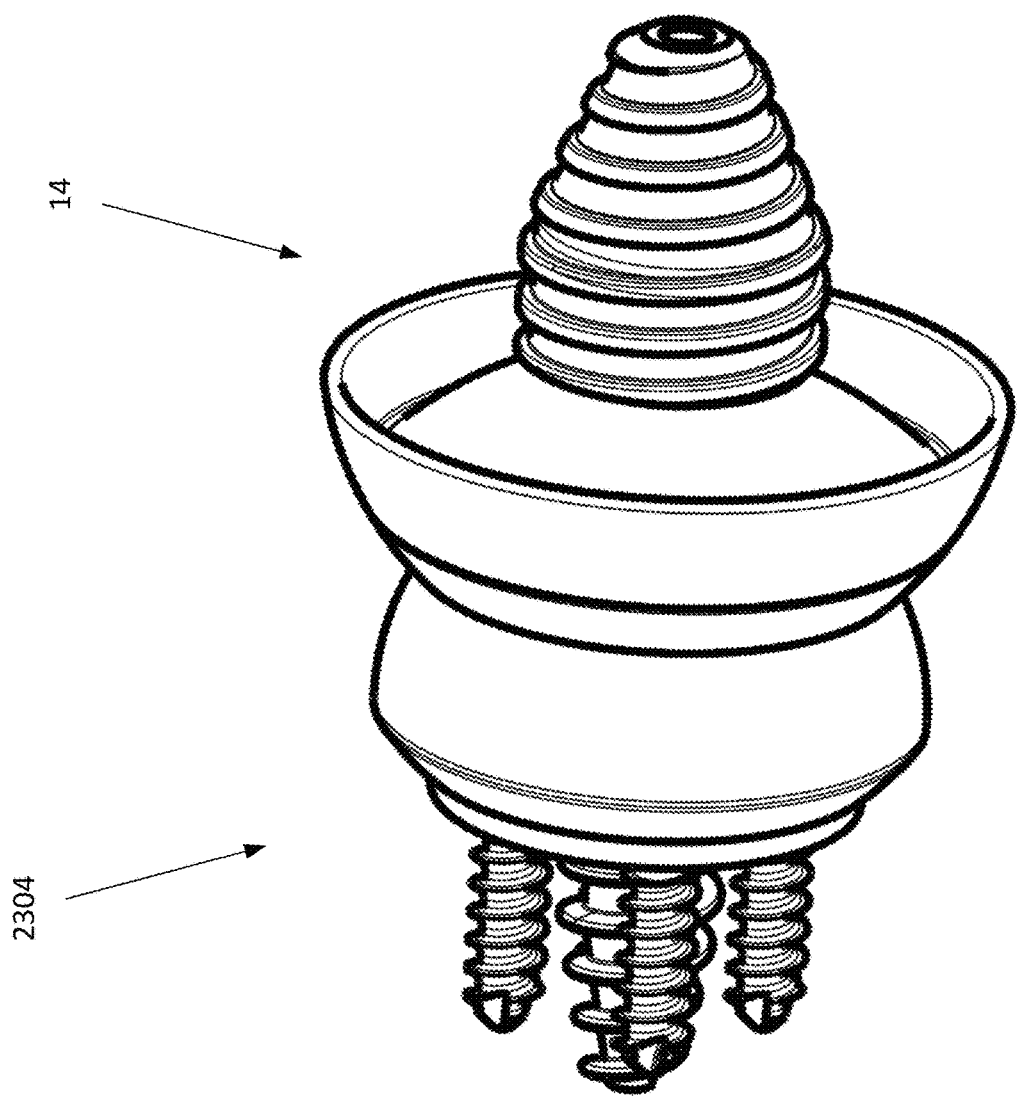
Figure 49:
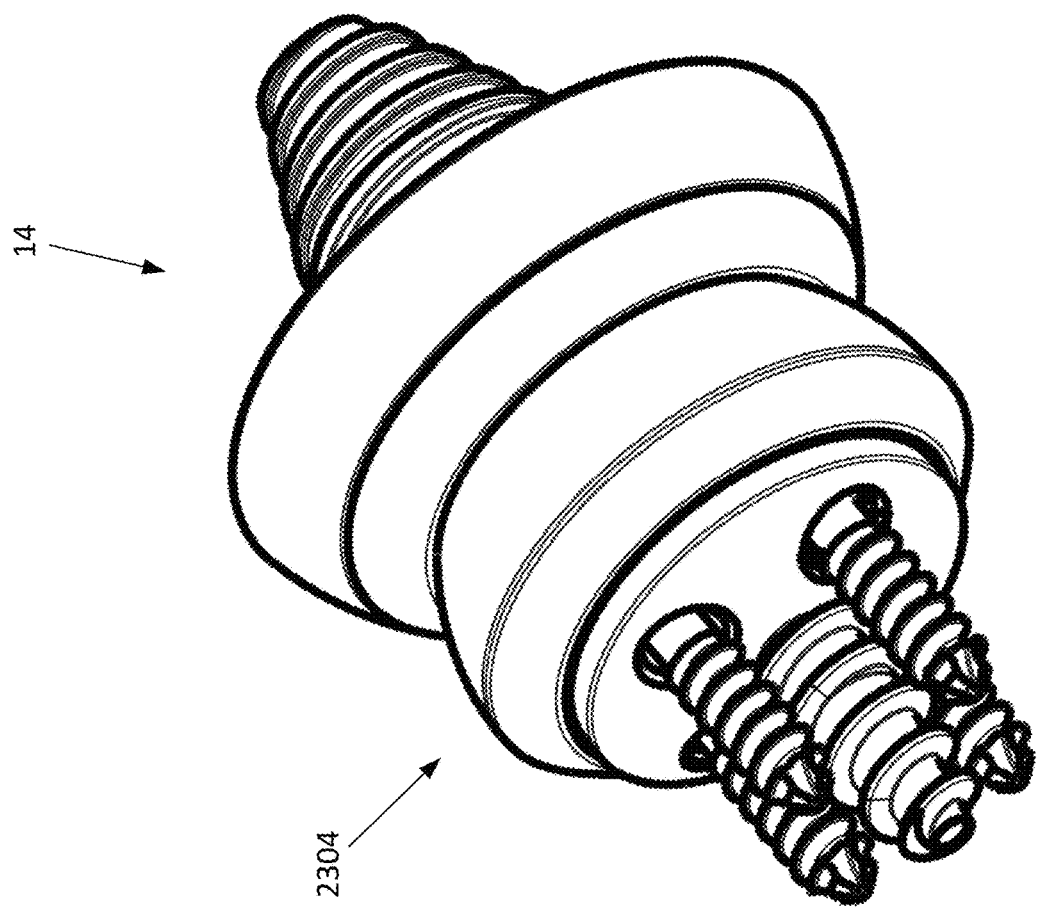

Once the baseplate 2404 has been secured to the anchor 2402, the implant 2406 may be secured to the baseplate 2404 as generally illustrated in FIGS. 40-41. Turning now to FIGS. 42A-E, various views of one example of an implant 2406 consistent with the present disclosure are generally illustrated. The implant 2406 (also generally referred to as a glenosphere) may include a body 4202, defining a load bearing surface 2410 and a baseplate interface surface 4206. The load bearing surface 2410 may include a convex surface 4208. The convex surface 4208 may therefore be used in a reverse shoulder application in which the native arrangement of the ball and socket of the shoulder is reversed. For example, the convex surface 4208 may include a semi-spherical shape and/or a semi-ellipsoidal shape. Alternatively, the load bearing surface may include concaved surface. The concaved surface (e.g., a generally spherical and/or semi-ellipsoid) may generally correspond native articular surface of the patient's glenoid 2302.

The baseplate interface surface 4206 is configured to at least partially receive the implant facing surface 3406 and/or the outer surface 3424 of the body 3402 of the baseplate 2404 such that the implant 2406 is coupled to the baseplate 2404. A portion 4205 of the baseplate interface surface 4206 may have a generally concaved shape that generally inversely corresponds to the implant facing surface 3406 of the baseplate 2404. Alternatively (or in addition), a portion 4207 of the baseplate interface surface 4206 may have a generally cylindrical shape that generally inversely corresponds to the outer surface 3424 of the body 3402 of the baseplate 2404 (optionally to form a tapered connection).

As discussed herein, the implant 2406 may include one or more baseplate fixation elements 4240 configured to be coupled to a corresponding implant fixation element 3420 of the baseplate 2404 to secure the implant 2406 to the baseplate 2404. In the illustrated example, the fixation elements 3420, 4240 may form Morse taper connection or the like. For example, the baseplate fixation element 4240 may include a tapered configured to receive the tapered male protrusion 3420 of the baseplate 2404. Of course, the arrangement of the male and female portions of the fixation elements 3420, 4240 may be reversed and the fixation elements 3420, 4240 may alternatively or additionally include any other mechanism and/or fastener for either permanently or removably coupling the implant 2406 to the baseplate 2404 such as, but not limited to, snap fit connections, threaded connections, adhesives, or the like.

The implant 2406 may also optionally include one or more implant alignment features 4228 configured to generally align the implant 2406 relative to the baseplate 2404 and/or prevent movement (e.g., rotation) of the implant 2406 relative to the baseplate 2404. In the illustrated embodiment, the implant alignment features 4228 includes a recess configured to receive at least a portion of a post 3428 extending outward from the implant facing surface 3406 of the baseplate 2404. The post and recess 3428, 4228 may optionally be tapered (e.g., to form a Morse taper or the like). Of course, the implant alignment features 3428, 4228 are not limited to this configuration. For example, the arrangement of the post and the recess may be reversed.

Optionally, a set-screw or the like may be advanced through an implant passageway 4250. The implant passageway 4250 may extend through the body 4202 (e.g., from the load bearing surface 2410 and a baseplate interface surface 4206). The implant passageway 4250 may be configured to receive a fastener (e.g. a threaded fastener) to aid in coupling the implant 2406 to the baseplate 2404 and/or the anchor 2402.

Alternatively (or in addition), a fastener or the like may be coupled directly to the baseplate 2404 and/or the anchor 2402 and may be used to remove (e.g., uncouple) the implant 2406 from the baseplate 2404 and/or the anchor 2402. For example, fastener 2321 (FIG. 23) may be threaded to the baseplate 2404 and/or the anchor 2402. To uncouple the implant 2406 from the baseplate 2404 and/or the anchor 2402, the user may advance a tool (e.g., a driver or the like) through the implant passageway 4250 and rotate the fastener. Rotation of the fastener may cause the fastener to advance out of the baseplate 2404 and/or the anchor 2402 and engage against the implant 2406, thereby urging the implant 2406 away from the baseplate 2404 and/or the anchor 2402 and uncoupling the implant 2406 from the baseplate 2404 and/or the anchor 2402. This arrangement may be particularly useful if a subsequent revision to the implant system 2304 is desired.

The anchor 2402, baseplate 2404, and/or the implant 2406 may be made from metal such as, but not limited to, cobalt chromium, stainless steel, and/or titanium (and alloys thereof). The baseplate 2404 and/or the implant 2406 may optionally be made from biocompatible plastic such as, but not limited to, ultra-high-molecular-weight polyethylene (UHMWPE) or the like.

Turning now to FIGS. 43-49, various examples of the first implant system 14 and the second implant system 2304 are shown. In the illustrated examples, the first implant system 14 and the second implant system 2304 are a humeral implant system and a glenoid implant system, respectively, through it should be appreciated that the first implant system 14 and the second implant system 2304 may be used in other joints. The humeral implant system 14 and glenoid implant system 2304 as illustrated form a reverse shoulder system in which the ball and socket arrangement has been switch from the native anatomical configuration; however, it should be appreciated that humeral implant system 14 and glenoid implant system 2304 consistent with the present disclosure may also be used to form a traditional, anatomical should replacement (either a partial or total shoulder replacement).

As used herein, "substantially corresponds" or "generally corresponds" means that the contour/profile of the articulating surface is within 15% of the contour/profile of the patient's native articular surface being replaced and/or within engineering and/or anatomical tolerance. In some instances, the contour/profile of the articulating surface may not correspond to the contour/profile of the patient's native articular surface being replaced.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims.

What is claimed is:

1. A humeral implant comprising:
    a tray including a body defining a bone facing recess and a liner recess, said bone facing recess including a ring surface and a convex surface, wherein the ring surface has a profile substantially corresponding to a profile of an outer ring of bone in an excision site of a patient; and wherein said convex surface has a profile substantially corresponding to a profile of a concave socket formed in the excision site;
    a liner including a body defining a load bearing surface and a tray interface surface, said tray interface surface being configured to be at least partially received in said liner recess of said tray such that said liner is coupled to said tray; and
    an anchor configured to be secured to bone within the excision site, said anchor including a first fixation element; wherein the tray further comprises a second fixation element configured to be coupled to said first fixation element to secure said tray to said anchor and wherein the first fixation element of the anchor includes a female tapered recess and the second fixation element includes a male taper post to engage the female taper recess.

2. The humeral implant of claim 1, wherein the anchor has a body portion having a tapered profile.

3. The humeral implant of claim 1, wherein the anchor has a body portion including one or more retaining elements disposed on an outer portion of the body portion to engage the patient's humeral bone within the excision site; wherein the one or more retaining elements is selected from the group of threads, protrusions, ribs, barbs, and/or recesses.

4. The humeral implant of claim 1, wherein an internal side of the ring surface is configured to receive the outer ring of bone such that the outer ring of bone is bound by the ring surface.

5. The humeral implant of claim 1, wherein the tray further includes a peripheral region between the ring surface and the convex surface, the peripheral region is configured to receive a rim portion of the outer ring of bone in the excision site of the patient.

6. An implant system comprising:
    a humeral implant comprising:
        a tray including a body defining a bone facing recess and a liner recess, said bone facing recess including a ring surface and a convex surface, wherein the ring surface has a profile substantially corresponding to a profile of an outer ring of bone in an excision site of a patient; and wherein said convex surface has a profile substantially corresponding to a profile of a concave socket formed in the excision site;
        a liner including a body defining a humeral load bearing surface and a tray interface surface, said tray interface surface being configured to be at least partially received in said liner recess of said tray such that said liner is coupled to said tray; and
        an anchor configured to be secured to bone within the excision site, said anchor including a first fixation element; wherein the tray further comprises a second fixation element configured to be coupled to said first fixation element to secure said tray to said anchor and wherein the first fixation element of the anchor includes a female tapered recess and the second fixation element includes a male taper post to engage the female taper recess; and
    a glenoid implant comprising:
        a baseplate including a body defining a bone facing surface and an implant facing surface; the bone facing surface having a profile substantially inversely corresponding to a profile of a glenoid implant site; and
        an implant having a glenoid load bearing surface and a baseplate interface surface;
        the glenoid load bearing surface having a shape to cooperate with the humeral load bearing surface of the liner.

7. The implant system of claim 6, wherein the anchor has a body portion having a tapered profile.

8. The implant system of claim 6, wherein the anchor has a body portion including one or more retaining elements disposed on an outer portion of the body portion to engage the patient's humeral bone within the excision site; wherein the one or more retaining elements is selected from the group of threads, protrusions, ribs, barbs, and/or recesses.

9. The implant system of claim 6, wherein an internal side of the ring surface is configured to receive the outer ring of bone such that the outer ring of bone is bound by the ring surface.

10. The implant system of claim 6, wherein the tray further includes a peripheral region between the ring surface and the convex surface, the peripheral region is configured to receive a rim portion of the outer ring of bone in the excision site of the patient.

11. The implant system of claim 6, wherein the humeral load bearing surface of the liner is a concave surface and the glenoid load bearing surface of the implant is a convex surface.

12. The implant system of claim 6, wherein the baseplate further comprises an alignment element protrusion on the implant facing surface.

13. The implant system of claim 12, wherein the implant further comprises a recess formed in the baseplate interface surface; wherein the recess is dimensioned to receive the alignment element protrusion to secure the implant to the baseplate.

14. The implant system of claim 6, wherein the implant and baseplate are configured to be coupled together using a friction fit.

* * * * *